(12) United States Patent
Houghten et al.

(10) Patent No.: US 6,197,529 B1
(45) Date of Patent: Mar. 6, 2001

(54) LINEAR SUBSTITUTED OLIGOALKYLENEIMINE LIBRARIES

(75) Inventors: Richard A. Houghten, Solana Beach; Julio Hernan Cuervo, La Jolla; Fred F. Weitl, San Diego, all of CA (US)

(73) Assignee: Torrey Pines Institute for Molecular Studies, San Diego, CA (US)

( * ) Notice: Subject to any disclaimer, the term of this patent is extended or adjusted under 35 U.S.C. 154(b) by 0 days.

(21) Appl. No.: 08/063,279

(22) Filed: May 18, 1993

Related U.S. Application Data

(63) Continuation-in-part of application No. 07/943,709, filed on Sep. 11, 1992, now Pat. No. 5,556,762, which is a continuation-in-part of application No. 07/797,551, filed on Nov. 19, 1991, now abandoned, which is a continuation-in-part of application No. 07/701,658, filed on May 16, 1991, now abandoned, which is a continuation-in-part of application No. 07/617,023, filed on Nov. 21, 1990, now abandoned.

(51) Int. Cl.[7] .......................... G01N 33/567; C12Q 1/00; H01R 13/60; A61K 38/00

(52) U.S. Cl. .......................... 435/7.21; 435/7.1; 435/7.2; 435/7.4; 435/DIG. 34; 435/DIG. 39; 436/501; 436/536; 530/333; 530/334; 530/345

(58) Field of Search .......................... 435/7.1, 7.2, 7.21; 436/501, 536; 530/333, 334, 345

(56) References Cited

U.S. PATENT DOCUMENTS

| | | | |
|---|---|---|---|
| 4,631,211 | 12/1986 | Houghten | 428/35 |
| 4,708,872 | 11/1987 | Geysen | 424/88 |
| 4,833,092 | 5/1989 | Geysen | 436/501 |
| 5,010,175 | 4/1991 | Rutter et al. | 530/334 |
| 5,093,320 | * 3/1992 | Nyeki et al. | 514/18 |
| 5,182,366 | 1/1993 | Huebner et al. | 530/334 |
| 5,194,392 | 3/1993 | Geysen | 436/518 |
| 5,202,418 | 4/1993 | Lebl et al. | 530/334 |

FOREIGN PATENT DOCUMENTS

| | | |
|---|---|---|
| 84/03506 | 9/1984 | (WO). |
| 84/03564 | 9/1984 | (WO). |
| 86/00991 | 2/1986 | (WO). |
| 9200091 | * 1/1992 | (WO). |
| 92/09300 | 6/1992 | (WO). |

OTHER PUBLICATIONS

Plattner et al., *Drug Discovery Technologies,* Clark et al., eds., Ellis Harwood Ltd., pp. 92–126 (1990).
Coy et al Tetrahedron 44 #3 pp 835–841 (1988) "Solid Phone Reductive Alkylation in Analogue Peptide Bond and Side–Chain Modification".*
Neuge bauer "A Guide to the Properties and Uses of Detergents in Biology or Biochemistry" (1988) Cal Biochem Corporation.*
Merrifield et al., *J. Amer. Chem. Soc.,* 85:2149–2154 (1963).
Houghten, *Proc. Natl. Acad. Sci.,* 82:5131–5135 (1985).
Houghten et al., *Biotechniques,* 4(6), 522–528 (1986).
Geysen et al., *Proc. Natl. Acad. Sci. U.S.A.,* 81:3998–4002 (1984).
Geysen et al., *Proc. Natl. Acad. Sci. U.S.A.,* 82:178–182 (1985).
Geysen et al., in *Synthetic Peptides as Antigens,* 130–149 (1986).
Geysen et al., *J. Immunol.,* 102:259–274 (1987).
Schoofs et al., *J. Immunol.,* 140:611–616 (1988).
Furka et al., (1988, 14th International Congress of Biochemistry, vol. 5, Abstract FR:013).
Furka et al., *Int. J. Peptide Protein Res.,* 37:487–493 (1991).
Devlin et al., *Science,* 249:404–405 (1990).
Scott et al., *Science,* 249:386–390 (1990).
Fodor et al., *Science,* 251:767–773 (1991).
Lam et al., *Letters to Nature,* 354:82–84 (1991).
Houghten et al., *Nature,* 354:84 (1991).
Krchnák et al., *Coll Czech. Chem. Commun.,* 53:2542 (1988).
Raucher et al., *Tetrahedron Lett.,* 21:4061–4064 (1980).
Furka et al., Xth International Symposium on Medicinal Chemistry, Budapest, Abstract 288, p. 68 (1988).
Houghten et al., *Peptides,* Smith and Rivier, eds., Proceedings of the Twelfth American Peptide Symposium, ESCOM, Leiden, pp. 560–561 (1992).
Houghten et al., *Innovation and Perspectives in Solid Synthesis: Peptides, Polypeptides and Oligoonucleodies,* R. Epton, ed., Intercept. Ltd., Andover pp. 237–239 (1992).
Pinilla et al., *BioTechniques,* 13:901–905 (1992).
Houghten, et al., *BioTechniques,* 13:412–421 (1992).
Pinilla et al., *Vaccines 92,* Synthetic Peptide Combinatorial Libraries: The Screening of Tens of Millions of Peptides for Basic Research and Drug Discovery, pp. 25–28 (1992).
Appel et al., *Immunomethods,* 1:17–23 (1992).

* cited by examiner

*Primary Examiner*—Jyothsna Venkat
*Assistant Examiner*—Joseph W. Ricigliano
(74) *Attorney, Agent, or Firm*—Welsh & Katz, Ltd.

(57) ABSTRACT

Linear substituted oligoalkyleneimine molecules and libraries of molecules are disclosed, as are their methods of synthesis and use in acceptor binding assays. Each molecule or chain of a library contains the same number of 2 to about 10 substituted alkyleneimine repeating units, whose substituents are reduced amino acid side chains bonded to the repeating units at a position alpha to the nitrogen atom, and the member chains of a library are present in equimolar amounts. The chains of a library contain one or more predetermined reduced amino acid side chain-substituted repeating units at one or more predetermined positions of the substituted oligoalkyleneimine chain. The library contains equimolar amounts of at least six different reduced amino acid side chain-substituted repeating units at one or more of the same predetermined positions of the substituted oligoalkyleneimine chain. Particularly preferred linear substituted oligoalkyleneimine molecules and libraries are linear substituted oligoethyleneimines.

16 Claims, 2 Drawing Sheets

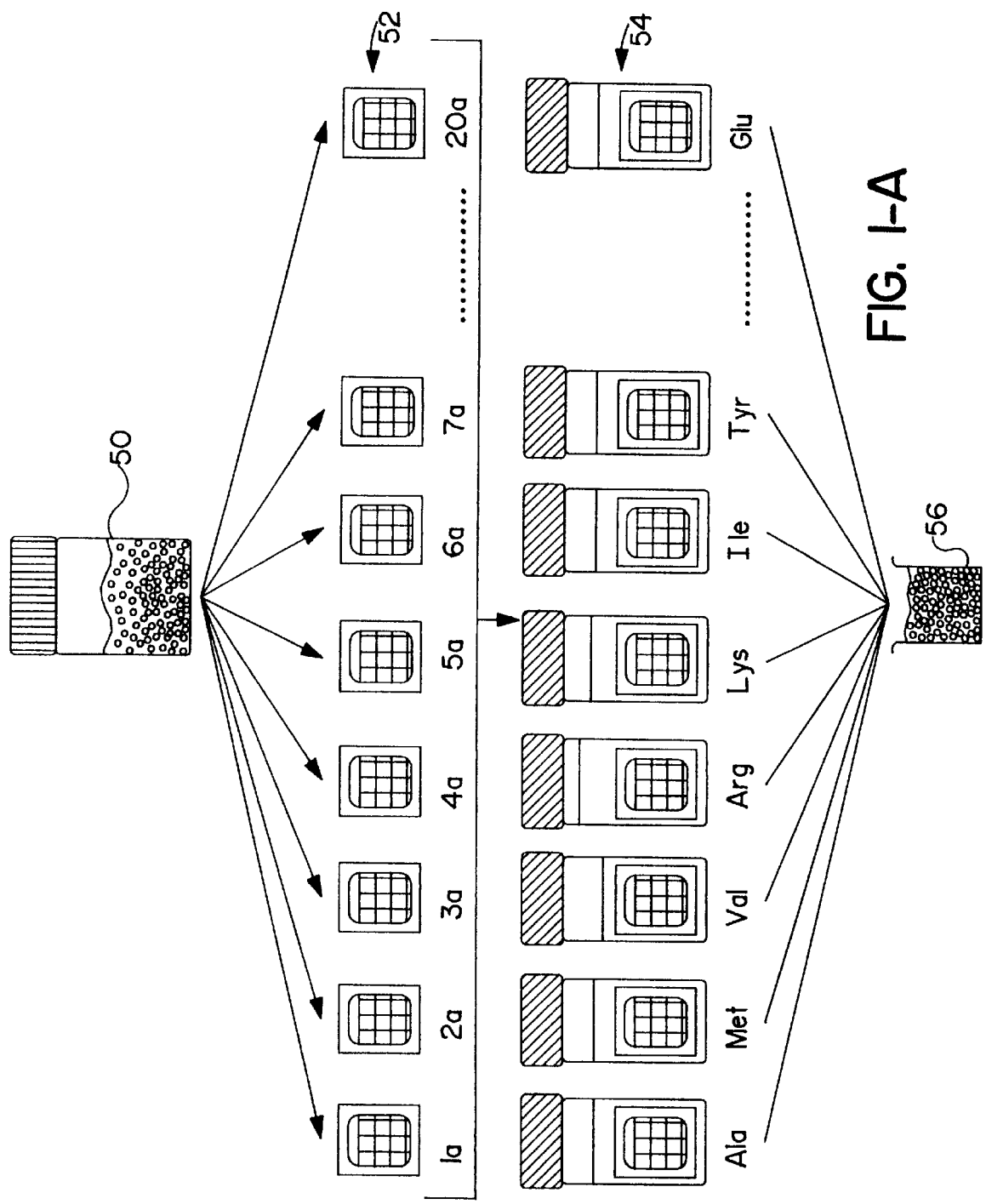
FIG. I-A

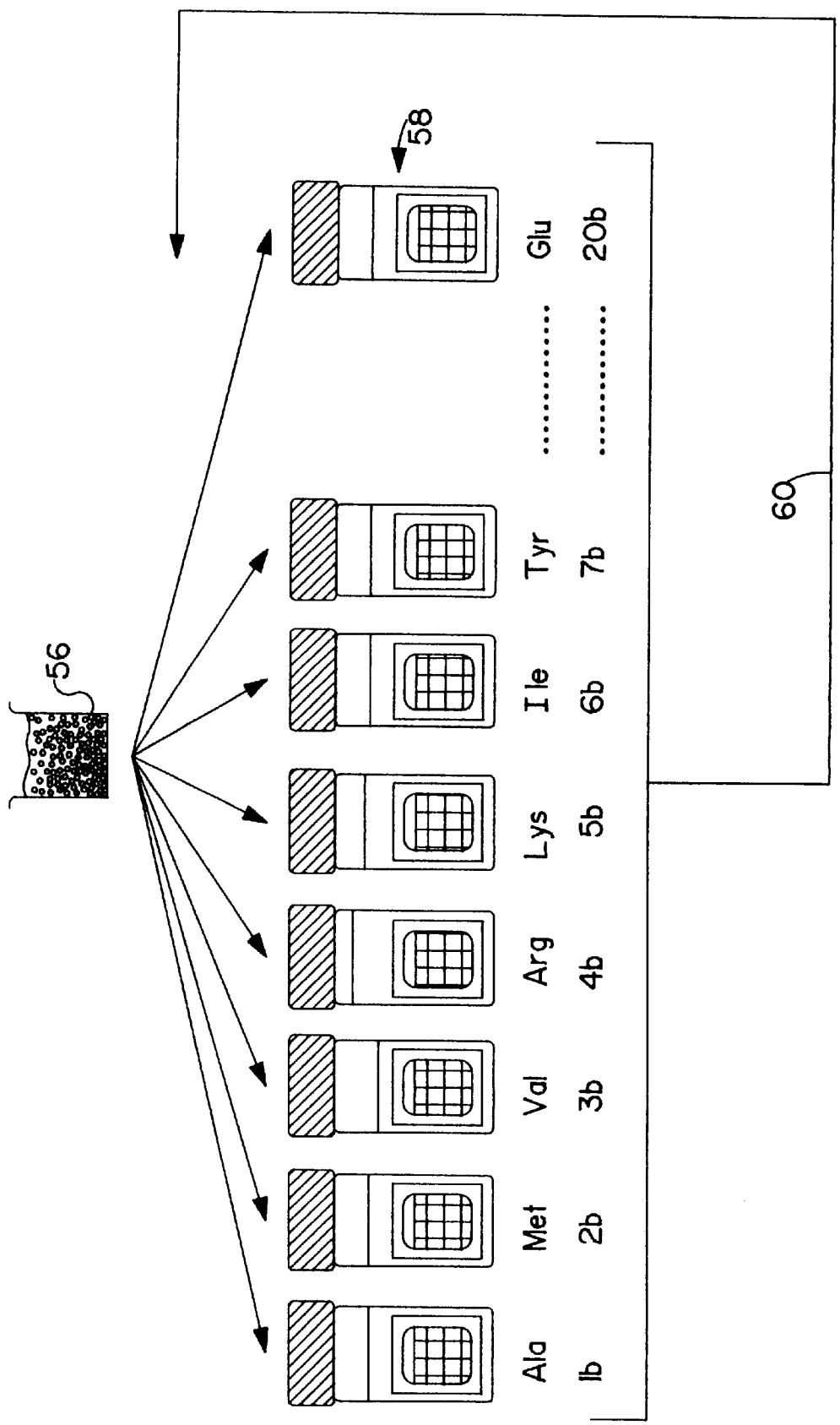
FIG. 1-B

US 6,197,529 B1

LINEAR SUBSTITUTED OLIGOALKYLENEIMINE LIBRARIES

CROSS-REFERENCE TO RELATED APPLICATIONS

This is a continuation-in-part of application Ser. No. 07/943,709, filed Sep. 11, 1992, now U.S. Pat. No. 5,556,762, that was a continuation-in-part of application Ser. No. 07/797,551 filed Nov. 19, 1991, now abandoned that was a continuation-in-part of application Ser. No. 07/701,658, filed May 16, 1991, now abandoned, that was a continuation-in-part of application Ser. No. 07/617,023, now abandoned, filed Nov. 21, 1990, whose disclosures are incorporated by reference.

TECHNICAL FIELD

The present invention relates to the synthesis and use of oligoalkyleneimine sequences. More particularly, the invention relates to the synthesis and use of a plurality of linear substituted oligoalkyleneimine libraries, as well as to individual olioalkyleneimine molecules that are preferably oligoethyleneimines.

BACKGROUND AND RELATED ART

Over the last several years, developments in peptide synthesis technology have resulted in automated synthesis of peptides accomplished through the use of solid phase synthesis methods. The solid phase synthesis chemistry that made this technology possible was first described in Merrifield et al. *J. Amer. Chem. Soc.*, 85:2149–2154 (1963). The "Merrifield method" has for the most part remained largely unchanged and is used in nearly all automated peptide synthesizer s available today.

In brief, the Merrifield method involves synthesis of a peptide chain on solid support resin particles. These particles typically are comprised of polystyrene cross-linked with divinyl benzene to form porous beads that are insoluble in both water and various organic solvents used in the synthesis protocol. The resin particles contain a fixed amount of amino- or hydroxylmethyl aromatic moiety that serves as the linkage point for the first amino acid in the peptide.

Attachment of the first amino acid entails chemically reacting its carboxyl-terminal (C-terminal) end with derivatized resin to form the carboxyl-terminal end of the oligopeptide. The alpha-amino end of the amino acid is typically blocked with a t-butoxy-carbonyl group (t-Boc) or with a 9-fluorenylmethyloxycarbonyl (Fmoc) group to prevent the amino group that could otherwise react from participating in the coupling reaction. The side chain groups of the amino acids, if reactive, are also blocked (or protected) by various benzyl-derived protecting groups in the form of ethers, thioethers, esters, and carbamates.

The next step and subsequent repetitive cycles involve deblocking the amino-terminal (N-terminal) resin-bound amino acid (or terminal residue of the peptide chain) to remove the alpha-amino blocking group, followed by chemical addition (coupling) of the next blocked amino acid. This process is repeated for however many cycles are necessary to synthesize the entire peptide chain of interest. After each of the coupling and deblocking steps, the resin-bound peptide is thoroughly washed to remove any residual reactants before proceeding to the next. The solid support particles facilitate removal of reagents at any given step as the resin and resin-bound peptide can be readily filtered and washed while being held in a column or device with porous openings such as a filter.

Synthesized peptides are released from the resin by acid catalysis (typically with hydrofluoric acid or trifluoroacetic acid), which cleaves the peptide from the resin leaving an amide or carboxyl group on its C-terminal amino acid. Acidolytic cleavage also serves to remove the protecting groups from the side chains of the amino acids in the synthesized peptide. Finished peptides can then be purified by any one of a variety of chromatography methods.

Though most peptides are synthesized with the above described procedure using automated instruments, a recent advance in the solid phase method by R.A. Houghten allows for synthesis of multiple independent peptides simultaneously through manually performed means. The "Simultaneous Multiple Peptide Synthesis" ("SMPS") process is described in U.S. Pat. No. 4,631,211 (1986); Houghten, *Proc. Natl. Acad. Sci.*, 82:5131–5135 (1985); Houghten et al., *Int. J. Peptide Protein Res.*, 27:673–678 (1986); Houghten et al., *Biotechniques*, 4, 6, 522–528 (1986), and Houghten, U.S. Pat. No. 4,631,211, whose disclosures are incorporated by reference.

Illustratively, the SMPS process employs porous containers such as plastic bags to hold the solid support synthesis resin. A Merrifield-type solid-phase procedure is carried out with the resin-containing bags grouped together appropriately at any given step for addition of the same, desired amino acid residue. The bags are then washed, separated and regrouped for addition of subsequent same or different amino acid residues until peptides of the intended length and sequence have been synthesized on the separate resins within each respective bag.

That method allows multiple, but separate, peptides to be synthesized at one time, since the peptide-linked resins are maintained in their separate bags throughout the process. The SMPS method has been used to synthesize as many as 200 separate peptides by a single technician in as little as two weeks, a rate vastly exceeding the output of most automated peptide synthesizers.

A robotic device for automated multiple peptide synthesis has been recently commercialized. The device performs the sequential steps of multiple, separate solid phase peptide synthesis through iterative mechanical-intensive means. This instrument can synthesize up to 96 separate peptides at one time, but is limited at present by the quantity of its peptide yield.

Of interest is work by Geysen et al., which deals with methods for synthesizing peptides with specific sequences of amino acids and then using those peptides to identify reactions with various receptors. Geysen et al.'s work presupposes that one has a prior knowledge of the general nature of the sequences required for the particular receptors, so that the appropriate group of peptides can be synthesized. See U.S. Pat. Nos. 4,708,871 and 4,833,092; P.C.T. Publications Nos. WO 84/03506 and WO 84/03564; Geysen et al., *Proc. Natl. Acad. Sci. U.S.A.*, 11:3998–4002 (1984); Geysen et al., *Proc. Natl. Acad. Sci. U.S.A.*, 82:178–182 (1985); Geysen et al., in *Synthetic Peptides as Antigens*, 130–149 (1986); Geysen et al., *J. Immunol. Meth.*, 102:259–274 (1987); and Schoofs et al., *J. Immunol.*, 140:611–616 (1988).

Several research groups have reported the synthesis of synthetic combinatorial libraries of peptides. Those reports are discussed below.

In published PCT application PCT/AU85/00165 (WO 86/00991), Geysen describes a method for determining so-called "mimotopes". A mimotope is defined as a catamer (a polymer of precisely defined sequence formed by the condensation of a precise number of small molecules), which in at least one of its conformations has a surface region with the equivalent molecule topology to the epitope of which it is a mimic. An epitope is defined as the surface of an antigenic molecule which is delineated by the area of interaction with an antibody molecule.

The mimotopes are synthesized on a series of solid polymer (e.g. polyethylene with a coating of grafted polyacrylic acid) rods having a diameter of about 4 mm and a length of about 50 mm. A spacer formed by reaction of the ε-amino group of t-Boc-lysine methyl ester and then t-Boc-alanine was added to the grafted polyacrylic acid resins, followed by removal of the t-Boc group to provide an amino group to be used to begin the syntheses.

A mixture of blocked amino acids containing different amounts of each of the blocked twenty amino acids to be used was dissolved in dimethyl formamide and then coupled to the rods. That first coupling was repeated three times using conventional solid phase synthesis techniques. Twenty amino acid residues were individually next added so that twenty 5-mer sequences were prepared, each having a single, known amino acid residue at the amino-terminus and a mixture of amino acid residues at each of the four other positions of the chain. Each of those twenty rod-linked peptides was then individually reacted with each of the twenty amino acid residues to form 400 (20×20) 6-mer peptides having the two amino-terminal positions defined and the four remaining positions as mixtures. Two more positions of mixtures of amino acids were then added, and the terminal amine acetylated to form N-acetyl 8-mers linked to the rods whose first two amino acid positions were undefined (mixtures), followed by two defined positions, followed by four undefined positions (mixtures), followed by the spacer and then the supporting rods.

The 400 rod-linked N-acetyl 8-mer peptide mixture preparations were then screened in an ELISA assay using a monoclonal antibody to a desired antigenic protein. The 8-mers having the preferential binding to the antibody were identified. Two sets of further 8-mers that contained the identified best-binding 2-mer sequences within those 8-mers were prepared.

A first set contained mixed amino acids at the three C-terminal positions, followed toward the N-terminus, by a position containing each of the twenty amino acids made by twenty separate couplings, the identified 2-mer sequences, two further mixtures at the next two positions, and an N-terminal acetyl group. The second group contained mixed amino acids at the four C-terminal positions, the identified 2-mer sequences, a position made by separate couplings of each of the twenty amino acids, mixed amino acids as the terminal residues and an N-terminal acetyl group.

Each of those rod-linked N-acetyl 8-mers was again screened in an ELISA with the monoclonal antibody. The preferential binding sequences for each group were identified, and thus 4-mer, preferential-binding sequences were identified.

The above process of separately adding each of the amino acids on either side of identified preferential-binding sequences was repeated until an optimum binding sequence was identified.

The above method, although elegant, suffers from several disadvantages as to peptides. First, owing to the small size of each rod used, relatively small amounts of each peptide is produced. Second, each assay is carried out using the rod-linked peptides, rather than the free peptides in solution. Third, even though specific amounts of each blocked amino acid are used to prepare the mixed amino acid residues at the desired positions, there is no way of ascertaining that an equimolar amount of each residue is truly present at those positions.

In addition, Furka et al., (1988, 14th International Congress of Biochemistry, Volume 5, Abstract FR:013) described the synthesis of nine tetrapeptides each of which contained a single residue at each of the amino- and carboxy-termini and mixtures of three residues at each position therebetween. The abstract further asserts that those authors' experiments indicated that a mixture containing up to 180 pentapeptides could be easily synthesized in a single run. No biological assays were reported. More recently, Furka et al., *Int. J. Peptide Protein Res.*, 37:487–493 (1991) reported on the synthesis of mixtures of 27 tetrapeptides and 180 pentapeptides prepared by physically mixing reacted resin-linked peptides. Those peptides were synthesized with one or mixtures of three or four residues at each position along the chain. No biological results using those relatively simple mixtures were reported.

Recent reports (Devlin et al., *Science*, 249:404–405 [1990] and Scott et al., *Science*, 249:386–390 [1990]) have described the use of recombinant DNA and bacterial expression to create highly complex mixtures of peptides. For example, a 45-nucleotide base pair stretch of DNA was synthesized in which the individual nucleotide bases were varied to contain all four possible nucleotide bases (guanine, adenine, cytosine and thymidine) at every position in the synthesized DNA chain, except at each third position (3, 6, 9, etc.) which contained only guanine and cytosine. The omission of adenine and thymidine at every third position in the synthesized DNA removed the possibility of chain terminator triplet codons ending in A or T, such as TAA or TGA.

The resulting DNA sequence would then code for a mixture of 15-mer peptides with all combinations of the 20 naturally occurring amino acids at each position.

Those investigators fused the 45 synthetic nucleotide sequence to a gene coding for the coat protein of a simple bacteriophage and created a large library of these bacteriophages. Each member of the library contained a different 45-mer DNA fusion sequence and therefore each member of the library resulted in a different 15-mer peptide fused to the outer coat protein of its corresponding fully assembled bacteriophage particle. Screening of the recombinant bacteriophage particles in a biochemical assay allowed the investigators to find individual peptide-coat protein fusions (bacteriophages) that were active in that assay by enrichment, selection and clonal isolation of the enriched bacteriophages that contained active peptide fusions. By determining the DNA sequence of the cloned bacteriophages, the investigators could deduce which peptide sequences were active in their assay.

That method yielded several peptide sequences from a mixture of $10^7$ or more recombinant bacteriophages. Each of the 15-mer peptides found contained the same four-amino-acid sequence somewhere within its overall sequence, thereby allegedly validating the assay accuracy and methodological approach.

The recombinant DNA method is extremely powerful for screening large numbers of peptides. However, it is limited in that the peptides must be fused to a larger protein as a result of and integral to the design of the method. The peptide-protein fusions (and corresponding bacteriophage particles) are likely to be unreactive in many biochemical, biological and in vivo assays where the peptides must be present in solution without steric hindrance or conformational distortion. In addition, the method results in an over-representation of some sequences of peptides due to the inherent redundancy of the genetic code which has several codons per amino acid in some cases and only one codon per amino acid in others.

Still further, neither group reported data as being definitive for the determination of optimal peptide ligands for strepavidin (Devlin et al.), or for the two monoclonal antibodies raised against myohemerythrin (Scott et al.). Neither group provided a single specific answer comparable to the expected sequence.

More recently, Fodor et al., *Science*, 251:767–773 (1991), described the solid phase synthesis of thousands of peptides or nucleotides on glass microscope slides treated with aminopropyltriethoxysilane to provide amine functional groups. Predetermined amino acids were then coupled to predefined areas of the slides by the use of photomasks. The photolabile protecting group NVOC (nitroveratryloxycarbonyl) was used as the amino-terminal protecting group.

By using irradiation, a photolabile protecting group and masking, an array of 1024 different peptides coupled to the slide was prepared in ten steps. Immunoreaction with a fluorescent-labeled monoclonal antibody was assayed with epifluorescence microscopy.

This elegant method is also limited by the small amount of peptide or oligonucleotide produced, by use of the synthesized peptide or nucleotide affixed to the slide, and also by the resolution of the photomasks. This method is also less useful where the epitope bound by the antibody is unknown because all of the possible sequences are not prepared.

The primary limitation of the above new approaches for the circumvention of individual screening of millions of individual peptides by the use of a combinatorial library is the inability of the peptides generated in those systems to interact in a "normal" manner with acceptor sites, analogous to natural interaction processes (i.e., in solution at a concentration relevant to the receptors, antibody binding sites, enzyme binding pockets, or the like being studied without the exclusion of a large percentage of the possible combinatorial library). Secondarily, the expression vector systems do not readily permit the incorporation of the D-forms of the natural amino acids or the wide variety of unnatural amine acids which would be of interest in the study or development of such interactions.

Yet another approach was reported by Lam et al., *Letters to Nature*, 354:82–84 (1991). Those workers reported the preparation of millions of bead-linked peptides, each bead containing a different peptide. The peptide-linked beads were reacted with a fluorescent- or enzyme-labeled acceptor, the beads bound by the acceptor were physically removed, and the sequence of the bound peptide was analyzed.

The interest in obtaining biologically active peptides for pharmaceutical, diagnostic and other uses would make desirable a procedure designed to find a mixture of peptides or a single peptide within a mixture with optimal activity for a target application. screening mixtures of peptides enables the researcher to greatly simplify the search for useful therapeutic or diagnostic peptide compounds. Mixtures containing hundreds of thousands or more peptides are readily screened since many biochemical, biological and small animal assays are sensitive enough to detect activity of compounds that have been diluted down to the nanogram or even picogram per milliliter range, the concentration range at which naturally occurring biological signals such as peptides and proteins operate.

Almost all of the broad diversity of biologically relevant ligand-receptor (or affector-acceptor) interactions occur in the presence of a complex milieu of other substances (i.e., proteins make up approximately 5–10 percent of plasma, e.g. albumin 1–3 percent, antibodies 2–5 percent-salts, lipids/fats, etc.). This is true for virtually all biologically active compounds because most are commonly present, and active, at nanomolar and lower concentrations. These compounds are also, in most instances, produced distant from their affection sites.

That a small peptide (or other molecule) can readily "find" an acceptor system, bind to it, and affect a necessary biological function prior to being cleared from the circulation or degraded suggests that a single specific peptide sequence can be present in a very wide diversity, and concentration, of other individual peptides and still be recognized by its particular acceptor system (antibody, cellular receptor, etc.). If one could devise a means to prepare and screen a synthetic combinatorial library of peptides, then the normal exquisite selectivity of biological affector/acceptor systems could be used to screen through vast numbers of synthetic oligopeptides.

The above work with and implications from use of oligopeptides notwithstanding, oligopeptide life times in in vivo systems are typically quite short due to hydrolysis and other degradative mechanisms that depend on the peptide bind. Hydrolysis, both by enzymes and stomach acids, also limits peroral administration of otherwise active oligopeptides. Still further, the presence in an oligopeptide of one or more hydrophobic residues such as tryptophan, phenylalanine and tyrosine often makes the oligopeptide so insoluble in water and body fluids that it cannot be screened for activity let alone utilized.

The availability of a wide variety of clearly identified peptides or peptide-like molecules in relatively limited mixtures would greatly facilitate the search for optimal molecules for any particular therapeutic end use application. At the present time, researches are hampered by the inability to rapidly create, identify and screen large numbers of peptide-like molecules with specific receptors. Work such as reported by Geysen with peptides has been valuable where the general nature of the required amino acid residue sequence could be previously determined, so that the specific peptides of interest could be individually formulated. However, such techniques cannot insure that the optimum molecules are identified for testing.

It would therefore be of considerable interest to have a method for the synthesis of mixtures of peptide-like molecules in which individual amino acid side chain-containing repeating unit positions can be specifically defined, such that a comprehensive array of molecules is available to researchers for the identification of one or more of the optimal molecules for reaction with receptors (acceptors) of interest, from which one can derive optimum therapeutic materials for treatment of various organism dysfunctions.

BRIEF SUMMARY OF THE INVENTION

One aspect of the invention contemplates a library of linear substituted oligoalkyleneimine chains comprising a mixture of equimolar amounts of linear oligoalkyleneimine chain members containing the same number of about two to about ten alkyleneimine repeating units in each chain. Each of the alkyleneimine repeating units has a length of two to about six carbon atoms and has a reduced amino acid side chain bonded to the carbon atom alpha to the nitrogen atom in which the carboxamide groups of the reduced amino acid side chains are replaced by aminomethyl groups, carboxyl groups of the reduced amino acid side chains are replaced by hydroxymethyl groups, and guanidino groups of the reduced amino acid side chains are replaced by amino groups. The members of the library have one or more of the repeating units containing a predetermined reduced amino acid side chain at the same one or more predetermined positions of the oligoalkyleneimine chain, and the library has equimolar amounts of repeating units that contain at least six different of said reduced amino acid side chains at one or more of the same other positions of the oligoalkyleneimine chain. A first terminus of each of said oligoalkyleneimines in the library has a hydrogen, benzyl or $C_1$–$C_{18}$ hydrocarbyl group bonded to an amino group, and a second terminus is a hydroxyl or methylamino group.

The one or more repeating units containing the reduced amino acid side chains at the same one or more predetermined positions of the oligoalkyleneimine chain are preferably at a predetermined position that is adjacent to one terminus, and more preferably that one terminus is said first terminus. The first two repeating units contain the reduced amino acid side chains at the same one or more predetermined positions are adjacent said first terminus in another preferred embodiment. The equimolar amounts of repeating units that contain at least six different of the reduced amino acid side chains are at one or more positions that are adjacent to one terminus in another preferred embodiment, and more preferably, the one terminus is the second terminus.

The library of oligoalkyleneimine chains preferably contains five to about eight repeating units in each chain. Each alklyeneimine repeating unit preferably contains two carbon atoms and is thus an oligoethyleneimine chain. The alkyleneimine is preferably an acid addition salt.

Another aspect of the invention contemplates a process for determining the sequence of a linear reduced amino acid side chain-substituted oligoethyleneimine that preferentially binds to an acceptor. Such a process comprises the steps of:

(a) providing a plurality of libraries of linear reduced amino acid side chain-substituted oligoethyleneimines in which each library comprises a mixture of equimolar amounts of linear reduced amino acid side chain-substituted oligoethyleneimine member chains containing the same number of two to about ten reduced amino acid side chain-substituted ethyleneimine repeating units in each substituted oligoethyleneimine chain. The member chains of each library have one or more of at least six different predetermined substituent reduced amino acid side chains at one or more predetermined repeating unit positions of the oligoethyleneimine chain, and each library has an equimolar amount of at least six different reduced amino acid side chains at the same one or more other positions of the oligoethyleneimine chain. A first terminus of each of the oligoethyleneimines in the library has a hydrogen, benzyl or $C_1$–$C_{18}$ hydrocarbyl group bonded to an amino group, and the second terminus is a hydroxyl or methylamino group. The libraries differ in that the one or more predetermined reduced amino acid side chains present at the one or more predetermined chain positions within each library are different between the libraries.

(b) Each library from said plurality of libraries is separately admixed with the acceptor in an aqueous medium at a library concentration of about 0.1 milligrams per liter to about 100 grams per liter. The binding of each library to the acceptor is separately assayed. A library exhibiting preferential binding relative to the other libraries is determined, thereby identifying a substituent reduced amino acid side chain that provided preferential binding at said one or more predetermined positions.

(c) A second plurality of libraries of linear reduced amino acid side chain-substituted oligoethyleneimines is provided in which each library comprises a mixture of equimolar amounts of member linear reduced amino acid side chain-substituted oligoethyleneimine chains containing the same number of two to about ten substituted ethyleneimine repeating units in each substituted oligoethyleneimine chain as the chains of the first-named plurality of libraries. The member chains of each second plurality of libraries contain the one or more substituent reduced amino acid side chains of the first-named library identified as exhibiting preferential binding in the same one or more predetermined chain positions in the first-named libraries. The member chains of the second libraries have a predetermined one of the at least six different substituent reduced amino acid side chains at another predetermined position of the substituted oligoethyleneimine chain different from the one or more positions of the identified substituent reduced amino acid side chains of the first-named plurality of libraries. Each of the second plurality of libraries (a) has equimolar amounts of said at least six different substituent reduced amino acid side chains of the first-named libraries at the same one or more positions of the .substituted oligoethyleneimine chain not occupied by the one or more identified reduced amino acid side chain substituents or the predetermined reduced amino acid side chains, (b) has one fewer oligoethyleneimine repeating unit positions occupied by equimolar amounts of at least six different substituent reduced amino acid chains, and (c) has the same first and second termini as the oligoethyleneimines of said first-named library.

(d) Each library of said second plurality of libraries is separately admixed with the acceptor in an aqueous medium at a library concentration of about 0.1 milligrams per liter to about 100 grams per liter. The binding of each library to the acceptor is separately assayed. A second library exhibiting preferential binding is determined, thereby identifying a reduced amino acid side chain that provides preferential binding at said other predetermined position in the substituted oligoethyleneimine chain;

(e) Steps (c) and (d) are repeated using zero through seven further pluralities of libraries of linear reduced amino acid side chain-substituted oligoethyleneimines instead of the second plurality of libraries. Each further plurality of libraries of linear substituted oligoethyleneimines comprises a mixture of equimolar amounts of member linear substituted oligoethyleneimine chains containing the same number of two to about ten reduced amino acid side chain-substituted ethyleneimine repeating units in each oligoethyleneimine chain as the chains of the first-named plurality of libraries. The member chains of each further plurality of libraries contain the substituent reduced amino acid side chains in the oligoethyleneimine chain positions that exhibited preferential binding in a plurality of libraries used immediately before and a predetermined one of the at least six different substituent reduced amino acid side chains at another predetermined position of the substituted oligoethyleneimine chain different from the positions of the identified reduced amino acid side chains of the plurality of libraries used immediately before. Each of the further plurality of libraries has equimolar amounts of the at least six different substituent reduced amino acid side chains of the first-named libraries at the same one or more positions of the substituted oligoethyleneimine chain not occupied by the identified reduced amino acid side chains or the predetermined reduced amino acid side chains, and has the same first and second termini as the oligoethyleneimines of the first-named library.

(f) At least six reduced amino acid side chain-substituted oligoethyleneimine chains are provided in which each chain contains the same number of two to about ten substituted ethyleneimine repeating units in each substituted oligoethyleneimine chain as the chains of the first-named plurality of libraries. Each oligoethyleneimine chain contains the identified substituent reduced amino acid side chains in the substituted oligoethyleneimine chain positions that exhibited preferential binding in step (e) a predetermined one of the at least six different substituent reduced amino acid side chains at another predetermined position in the substituted oligoethyleneimine chain different from the positions of the identified substituent reduced amino acid side chains used in step (e), and has the same first and second termini as the oligoethyleneimines of the first-named library.

(g) Each of the at least six substituted oligoethyleneimines of (f) is separately admixed with the acceptor in an aqueous medium at a substituted oligoethyleneimine concentration of about 0.1 milligrams to about 100 grams per liter. The binding of each substituted oligoethyleneimine is separately assayed. The substituted oligoethyleneimine exhibiting preferential binding is determined, thereby determining the sequence of a linear reduced amino acid side chain-substituted oligoethyleneimine that preferentially binds to the acceptor.

The before-discussed preferences as to the libraries hold where the libraries are used in an above assay. In addition, it is preferred that the identified and predetermined substituent reduced amino acid side chains are substituents of adjacent repeating units. More preferably, the predetermined one or more of said at least six substituents reduced amino acid side chains at one or more predetermined positions of (a) include a terminal repeating unit position of the oligoethyleneimine chain.

It is also preferred that the first-named substituted oligoethyleneimine chains contain about 5 to about 8 repeating units. It is further preferred that at least ten different reduced amino acid side chain substituents are utilized instead of at least six.

In one preferred process, the acceptor is a cellular receptor. More preferably, the cellular receptor is present in a bacterium or yeast cell cultured in a growth medium.

Yet another embodiment is another process for determining the sequence of a linear reduced amino acid side chain-substituted oligoethyleneimine that preferentially binds to an acceptor. This process comprises the steps of:

(a) providing separate pluralities of libraries of linear reduced amino acid side chain-substituted oligoethyleneimine. Each library of those pluralities comprises a mixture of equimolar amounts of linear reduced amino acid side chain-substituted oligoethyleneimine chains containing the same number of two to about ten reduced amino acid side chain-substituted repeating units in each chain. Each substituted oligoethyleneimine chain has a single one of at least six different predetermined substituent reduced amino acid side chains at a single predetermined repeating unit position of the oligoethyleneimine chain, and each library has equimolar amounts of each of the at least six different substituent reduced amino acid side chains at the other positions of the oligoethyleneimine chain. Each library differs from the other libraries in the identity and chain position of the single predetermined substituent reduced amino acid side chain present at the predetermined repeating unit position within the library. A first terminus of each of the oligoethyleneimines in the library has a hydrogen, benzyl or $C_1$–$C_{18}$ hydrocarbyl group bonded to an amino group, and the second terminus is a hydroxyl or methylamino group.

(b) Each library is separately admixed with the acceptor in an aqueous medium at a library concentration of about 0.1 milligrams per liter to about 100 grams per liter, and the binding of each library to the acceptor is separately assayed. The substituent reduced amino acid side chain that exhibited preferential binding at each repeating unit position of the oligoethyleneimine chain provides the sequence of a linear reduced amino acid side chain-substituted oligoethyleneimine that preferentially binds to the acceptor.

The before-discussed preferences for the libraries also hold here. In addition, it is preferred that the single, predetermined repeating unit positions of the plurality of libraries, taken as a group, are adjacent to each other in the oligoethyleneimine chain. Each oligoethyleneimine chain also preferably contains about 5 to about 8 repeating units.

It is also preferred that the single predetermined repeating unit substituent side chain of each substituted oligoethyleneimine chain is one of at least ten different reduced amino acid side chains, and the same at least ten different substituent reduced amino acid side chains are present in equimolar amounts at the other substituted oligoethyleneimine positions of each library.

BRIEF DESCRIPTION OF THE DRAWINGS

In the drawings forming a portion of this disclosure;

FIG. 1 (on two sheets as FIG. 1-A and FIG. 1-B) is a schematic flow chart in two sheets illustrating a process for preparing peptides that can be utilized in this invention in an embodiment in which initial peptide mixtures are formed from the twenty naturally occurring amino acids.

The present invention has several benefits and advantages. One benefit of this invention is the facilitation of the formation and identification of specific biologically active substituted oligoalkyleneimine sequences for pharmaceutical, diagnostic and other uses, particularly those sequences that are of particular efficacy for the therapeutic treatment of target diseases.

An advantage of the present invention is that a sequence of a substituted oligoalkyleneimine ligand that preferentially binds to a preselected receptor can be ascertained in relatively few assays.

Another benefit of the present invention is that aliquots from the same library of linear substituted oligoalkyleneimines can be used for assays against any receptor to be screened.

Still further benefits and advantages of the invention will be apparent to the skilled worker from the discussion that follows.

DETAILED DESCRIPTION OF THE INVENTION

Introduction

Peptides are one of a number of fundamental classes of biologically relevant effector molecules. Acceptor systems for peptides include: antibodies, enzymes, membrane-bound and internal cellular receptors. Biologically important peptides include bradykinin, oxytocin, α-endorphins, insulin, and the like. Drug discovery involving peptides invariably requires the synthesis and testing of hundreds to thousands of analogs of the original biologically active sequences. In order to understand a given peptide's structure activity relationships, very large numbers of peptide analogs are needed in all of these areas.

The diversity of the combinatorial possibilities of even the 20 natural amino acids makes the before-described synthesis methods sorely limited in the task of screening for optimal peptide antigens, peptide ligands for biologically relevant acceptor systems, enzyme inhibitors, antimicrobials, and the like [i.e., there are 64,000,000 possible six residue peptides ($20^6$), 1,280,000,000 possible seven residue peptides ($20^7$), and the like]. Although the synthetic methods discussed before have greatly facilitated studies with synthetic peptides, and are available commercially either on a custom basis or for use in kit form, they permit only a very small fraction of possible oligopeptides (composed of either natural or unnatural amino acids) to be prepared.

Equimolar amounts of each component making up the library (or set) to be studied could be expected to ensure the necessary selectivity of the interactions of the desired oligoethyleneimine in the mixture to be used (i.e., the "needle in the haystack"-finding the correct hexaethyleneimine in the 64,000,000 possible combinations of the 20 natural amino acid side chains would be analogous to finding a single steel needle in 63,999,999 copper needles). As an insight into the extreme selection criterion involved in such a system, it is helpful if one considers that a single six-letter word would have to be readily found in the presence of 63,999,999 other six-letter words (63,999,999 six-letter words would fill approximately 50,000 pages of text of the size found in a usual scientific journal).

The present invention relates to oligomeric peptide-like molecules that have amino acid side chains. The peptide-like molecules of this invention are oligoalkyleneimines, and particularly oligoethyleneimines as are discussed below.

The present invention relates generally to substituted linear oligoalkyleneimines that contain 2 to about 10 alkyleneimine repeating units whose individual lengths can be 2 to about 6 carbon atoms. That is, compounds that include the linear repeating unit structure

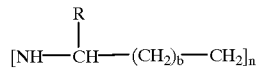

where b is zero through about 4 and n is an integer that is 2 through about 10, more preferably about 5 to about 8, and R is a substituent reduced amino acid side chain. It is noted that in a given oligoalkyleneimine, b for one repeating unit can be zero, whereas b for two repeating units is 1 and 4 for another repeating unit so that b need not be constant throughout the alkyleneimine chain. Preferably, b is constant throughout the chain and is zero, and the parenthesized methylene group [($CH_2$)] is absent so that a preferred oligoalkyleneimine is an oligoethyleneimine.

The preferred oligoethyleneimines are thus compounds that include the linear repeating unit structure

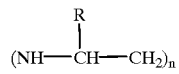

where n is an integer that is 2 through about 10, and more preferably about 5 to about 8, and R is a substituent reduced amino acid side chain. In another aspect, the invention relates to libraries of linear substituted oligoalkyleneimines, and particularly linear substituted oligoethyleneimines.

For ease of understanding, oligoethyleneimines will usually be discussed hereinafter as exemplary and preferred oligoalkyleneimines.

A contemplated linear oligoethyleneimine is substituted with a reduced amino acid side chain, R, located in the repeating unit alpha to the nitrogen atom depicted above; i.e., the first carbon away from the nitrogen atom. The usual amino acid side chains of the twenty natural amino acids such as hydrogen for glycine, methyl for alanine and the like are contemplated reduced side chain R groups, as are unnatural side chains such as that of ornithine.

The side chains of most amino acids are unchanged on reduction so that, for example, the methyl side chain of an alanine amino acid residue in an oligopeptide is a methyl side chain of an oligoethyleneimine repeating unit. Carbonyl group- and guanidino group-containing side chains are not inert to the contemplated, preferred reduction process. As such, the side chains of aspartic and glutamic acids, asparagine and glutamine, and the guanidino group-containing side chain of arginine are not contemplated.

Rather, the carbonyl group of a carboximide and a carboxyl is replaced by methylene so that the carboxamides of asparagine and glutamine become aminomethyl (—$CH_2NH_2$) groups and the carboxyls of aspartic and glutamic acids become hydroxymethyl (—$CH_2OH$) groups. Those replacement groups can also be referred to as methyleneamino and methylenehydroxyl, respectively. When prepared by reduction of a corresponding oligopeptide, as is preferred and discussed hereinafter, an oligoethyleneimine is substantially free of carbonyl groups such as those of peptide bonds, with each carbonyl group of the corresponding peptide being replaced by a methylene group.

Similarly, the guanidino group of arginine is reduced to an amine group so that an arginine side chain becomes an ornithine side chain. Asparagine side chains also become ornithine side chains on reduction. Because appropriately protected ornithine derivatives are available commercially for use in peptide syntheses, that amino acid can be used in a sequence rather than either an arginine or asparagine.

In view of the fact that most amino acid side chains are inert to reduction, all of the side chains present in oligoethyleneimine repeating units will be usually referred to as an "amino acid side chain" or more simply as a "side chain", rather than as a "reduced amino acid side chain" or "reduced side chain". Similarly, a linear reduced amino acid side chain-substituted oligoethyleneimine will usually be referred to herein as a "linear substituted oligoethyeneimine" or more simply still as an "oligoethyeleneimine".

The contemplated libraries of linear substituted oligoethyleneimines are preferably prepared from corresponding sets or mixtures of oligopeptides by reduction of the mixture. An individual linear substituted oligoethyleneimine is preferably also prepared from a corresponding individual oligopeptide. As a consequence, in the description below, the invention will be described in a preferred embodiment in which the linear substituted oligoethyleneimines (also referred to herein as oligoethyleneimines) are prepared from oligopeptides that do or can contain most or all of the twenty naturally occurring amino acid residues. It will be understood, however, that the invention can be used with at least six different amino acid residue side chains, and more than twenty different residue side chains.

For instance, an oligoethyleneimine can include the naturally occurring 20 amino acids, one or both isomers of ornithine, norleucine, hydroxyproline, and the D-stereoisomers of the naturally occurring twenty amino acids, whereas a linear substituted oligoalkyleneimine can further include β-alanine, and other $C_4$–$C_6$ amino acids such as γ-amino butyric and ε-amino caproic acids so that use of about 50 different D- and L-protected amino acid derivatives is contemplated. Precursor oligopeptide sets and oligopeptide mixture pools (discussed hereinafter) that contain all D-amino acid residues and mixtures of both D- and L-forms are contemplated for use in preparing corresponding individual linear substituted oligoethyleneimines and linear substituted oligoethyleneimine libraries. Consequently, as used herein, the term "amino acid" will, unless otherwise stated, be intended to include not only the naturally occurring L-amino acids but also their D-stereoisomers and the derivatives thereof as well as all other amino acids that contain up to about twelve carbon atoms. The phrases "amino acid derivative", "protected amino acid derivative" or the like are used herein for a protected amino acid added as a reactant, whereas the phrase "amino acid residue", "residue" or the like is used herein for a reacted protected amino acid that is a portion of an oligopeptide chain.

Further, the terms "peptide" and "oligopeptide" are considered to be synonymous (as is commonly recognized) and each term can be used interchangeably as the context requires. The word "polypeptide" is used for chains containing more than ten amino acid residues. All oligopeptide and polypeptide formulas or sequences shown herein are written from left to right and in the direction from amino-terminus to carboxy-terminus.

The abbreviations used herein for derivatives and residues of the twenty natural amino acids are reproduced in the following Table of Correspondence:

| TABLE OF CORRESPONDENCE | | |
|---|---|---|
| Abbreviation | | |
| 1-Letter | 3-Letter | Amino Acid |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |

| -continued | | |
|---|---|---|
| TABLE OF CORRESPONDENCE | | |
| Abbreviation | | |
| 1-Letter | 3-Letter | Amino Acid |
| C | Cys | cysteine |
| X | Xaa | another residue, or one of several residues |

The word "predetermined" is used in two contexts herein, and has a similar meaning in each context.

A "predetermined" amino acid residue is a single residue whose identity is known or specifically defined, e.g., alanine, glycine, tyrosine, etc., as compared to being a mixture of residues. A linear substituted oligoethyleneimine similarly contains a before-defined amino acid side chain whose identity is known or specifically defined.

A "predetermined position" in an oligopeptide mixture sequence or chain is a position, from and including the amino-terminal residue as position 1, occupied by a predetermined amino acid residue or of a mixture of residues, and which position is known and specifically identified. A linear substituted oligoethyleneimine similarly contains a repeating unit amino acid side chain substituent at a particular position in the chain and, a library of such oligoethyleneimines also contains a mixture of amino acid side chains at other known or specified position(s) in the chain.

The letter "O" is used to indicate a predetermined, but unspecified single amino acid residue or the reduced side chain of an oligoethyleneimine repeating unit. Subscripted letters "O", e.g., $O_1$, $O_2$, $O_3$ . . . $O_n$ etc. indicate a predetermined amino acid residue or repeating unit side chain that is predetermined (specified) and at the same position (1, 2, 3 . . . n) among a set of oligopeptide mixtures, solid support-coupled oligopeptide mixtures, or in an oligoethyleneimine or library. Thus, a subscripted letter "O" such as $O_1$ is used where a particular amino acid residue or side chain is intended such as alanine or serine, whereas an unsubscripted letter "O" is used to mean that each of the plurality of residues or side chains is present at a given position, but that that residue or side chain is not specified. Subscripted numbers need not start at the amino-terminus for any given mixture.

The letter "X" is used to indicate that a position in an oligopeptide set or oligoethyleneimine library formula occupied by that letter is an equimolar mixture of each of at least six amino acid residues coupled or repeating unit side chains, and preferably ten or more such residues or side chains, and more preferably about 15 to about 20.

The letter "B" is used to indicate a solid support used in the syntheses described herein, such as a particulate resin.

The N-terminus of an oligopeptide is referred to herein as the first terminus of a corresponding oligoethyleneimine, whereas the C-terminus of an oligopeptide is referred to herein as the second terminus of a corresponding oligoethyleneimine. An oligoethyleneimine sequence will thus be discussed in the same left to right, N-terminus to C-terminus manner as is a peptide. An oligoethyleneimine "corresponds" to an oligopeptide when the former is the reduced form of the latter. In addition, an illustrated oligoethyleneimine sequence will be usually prefaced by the word "RED-" to further distinguish an oligoethyleneimine from its corresponding oligopeptide.

For example, a trimer oligopeptide pool linked to a solid support whose first position is defined and whose second and third positions are mixtures can be represented as $O_1XX$-B. Similarly, a library of preferred linear substituted oligoethyleneimines having six repeating units whose second and third positions contain predetermined amino acid side chains, whose remaining positions are occupied by mixtures of side chains, whose first-terminal nitrogen atom is bonded to a hydrogen and whose second terminus is an amino group can be depicted as RED-$X_1O_2O_3$XXX-$NH_2$.

Mixtures of linear substituted oligoethyleneimines are particularly contemplated herein. Those mixtures are preferably prepared by reduction of a corresponding mixture of oligopeptides. As an aid in understanding, a group of mixed linear substituted oligoethyleneimines is generally referred to as a "library", whereas a corresponding precursor mixture of oligopeptides is referred to as a "set".

A contemplated linear substituted oligoethyleneimine library contains at least one (one or more) predetermined substituent reduced amino acid side chain at at least one (one or more) predetermined repeating unit chain position and mixtures of at least six substituent reduced amino acid side chains used for synthesis at at least one (one or more) other positions of the oligoethyleneimine chain. At least six different amino acid side chains are present at the mixed positions and one of those same six side chains is the at least one predetermined side chain position for a given library with an exception discussed hereinafter. In preferred practice at least ten different amino acid side chains are used, and more preferably still, about 15 to about 20 amino acid side chains are used as side chains of the mixture positions and each can constitute the single, predetermined side chain at the at least one predetermined position.

Thus, the side chain of that at least one predetermined position can be one of at least six, preferably ten or more preferably about 15 to about 20 side chains. That at least one side chain is usually referred to herein as "a predetermined amino acid side chain", whereas in other instances that side chain is described as "one of at least six amino acid side chains" or the like.

Synthesis Processes

Overview

The preparation of a library of substituted, linear oligoethyleneimines having a predetermined side chain at at least one position and equimolar amounts of at least six other desired side chain substituent at at least one other position preferably begins with the preparation of a corresponding oligopeptide set that is thereafter reduced. Equimolarity being of importance for the side chain of the mixture positions, synthesis of the corresponding oligopeptide set is of importance. Two general approaches to such syntheses are preferred.

One approach involves the separation and recombination of oligopeptide-coupled solid supports. This approach entails the coupling to completion of each of the desired protected amino acids (e.g., t-Boc alanine, etc.) with equimolar portions of starting oligopeptide solid support such as a resin. Assurance that the reactions have all been driven to completion (>99.5 percent for each step) is made by standard assay procedures.

The resulting reacted resins are then combined and thoroughly mixed as solids (physically mixed) to form a pool, and following their deprotection and neutralization, the resulting pooled mixture is again divided into a number of equal portions. Each of these portions (that contain equimolar amounts of the different starting amino acid residue-coupled resins) is reacted with a single, predetermined amino acid derivative or is again separately coupled to completion with each of the desired protected amino acid derivatives. Where the 20 natural amino acids are used at each of the two coupling steps, this yields 20 different dipeptide-coupled resins for each of the 20 single amino acid resins (400 different dipeptide-resins in total). This process is then repeated, for example, until the desired length of the mixture of oligopeptide-coupled resins has been obtained. The single, predetermined residue is added similarly, but without mixing after the coupling step.

This method can be used with any number or kind of amino acid without limitation, to generate the exact oligopeptide-coupled resin mixture pool required. After deprotecting (or deblocking) and cleavage of the oligopeptide mixture from the solid support, the resulting oligopeptide set is reduced as with diborane to form a linear substituted oligoethyleneimine library. An aliquot taken prior to reduction can be used for amino acid and sequence analyses to confirm the expected results, but the accuracy of the methods used to prepare the resin coupled mixtures as described herein exceeds that of the analysis systems. Thus, the exactitude of physically weighing the resins, mixing them, separating them, and recombining them, along with the assurance of individual amino acid coupling completion by ninhydrin, picric acid or other means, ensures the necessary equimolarity.

Using most or all of the twenty natural amino acids, an initial concern with oligopeptide sets was that the more hydrophobic components of the mixtures would prove highly insoluble. This was not found to be the case due to the mutually self-solvating properties of the different sequences in each mixture set. oligoethyleneimine libraries are even more soluble in aqueous media than are the corresponding oligopeptide sets.

Although preferred in some instances and most effective in achieving equimolarity, the above physical mixing of solids is not always required to obtain the equimolarity needed for assay purposes. Rather, a reaction mixture containing amounts of amino acid derivatives calculated to provide reacted equimolarity, as being present in amounts proportional to their coupling constants, can be used (chemical mixture) for the coupling reactions. Deprotection and cleavage from the solid support followed by reduction as before also provides a linear substituted oligoethyleneimine library with the required equimolarity of side groups.

Once boron-containing reaction products or other reaction products that result from oligopeptide reduction are removed, no other manipulation is typically necessary prior to use of a prepared library. A library can be used in solution concentrations of each mixture ranging from about 0.001 to about 100 mg/ml. This permits the screening of each library in assay systems at concentrations that ensure that a sufficient concentration of every individual oligoethyleneimine is present in each assay.

For example, if the average molecular weight of a hypothetical linear substituted oligoethyleneimine [prepared from an N-acetyl C-amide hexapeptide (6-mer) oligopeptide mixture set] having one designated position and five mixtures positions is approximately 687, then a solution of a library of 3,200,000 oligoethyleneimines at a total final concentration of 5 mg/ml yields a concentration of each oligoethyleneimine in each library of about 1.37 µg/liter (about 1.5 pmoles/liter). These concentrations, without any consideration of potential positional redundancy, ensure that a sufficient concentration of each oligoethyleneimine is present for normal antigen/antibody interactions, receptor/ligand interactions, and enzyme/substrate interactions.

Syntheses of oligopeptide sets is typically carried out by combining the above methods with the simultaneous multiple peptide synthesis (SMPS) approach described before. Hundreds to thousands or millions of individual peptides can be readily prepared with this method using any of the currently existing chemistries. A combination of synthetic chemistries [(t-Boc)] permits: (1) the removal of all side chain protecting groups without cleaving the peptides from the resin [Tam's "low" HF method; Tam et al., *J. Am. Chem. Soc.*, 105:6442–6455 (1983)] and (2) complete, or virtually complete, removal of all of the mixtures from the resin by a final high HF treatment [Houghten et al., *Intl. J. Peptide Protein Res.*, 16:311–320 (1980)]. Use of the SMPS method is not necessary herein, but facilitates the syntheses.

A. Physical Mixture Process

One exemplary synthetic process useful herein utilizes a physical process for the synthesis of a complex mixture pool of solid support-coupled amino acid residues wherein the mixture contains an equimolar representation (amount) of at least six different amino acid residues coupled at at least one position and a predetermined amino acid residue of those at least six different residues at at least one predetermined position. Solid support-coupled oligopeptide mixture syntheses are discussed below using porous containers for simplicity of expression so that each type of synthesis need not be described.

The various solid supports such as particles can be utilized enclosed in a porous container. When that is the case, at least coupling reactions are carried out in such containers. However, porous containers need not be used and coupling reactions can be carried out in beakers, flasks, test tubes or the like as are well known.

Several embodiments of this process for oligopeptide synthesis are disclosed in the above enumerated predecessor patent applications as well as in Houghten et al., *Nature*, 35:84 (1991) and in WO 92/09300, published Jun. 11, 1992.

According to this process, (a) at least six porous containers, each containing a solid support comprised of particles linked to reactive functional groups are provided. The functional group of the solid support reacts with each amino acid to be reacted. The solid support particles are of a size that is larger than the pores of the container so that the individual solid support particles are maintained within the porous containers. Both the container and solid support are substantially insoluble in and substantially inert to a liquid medium used during the synthesis.

(b) At least six liquid media are provided, each medium containing a different protected amino acid derivative from a plurality of protected amino acid derivatives from which the oligopeptides are to be formed. Each of the protected amino acid derivatives has a first reactive functional group that reacts with the reactive functional group of the solid support, and a second reactive functional group that is capable of reacting during the reaction of the solid support functional group and the first reactive functional group, but is protected from so reacting by a selectively removable, covalently linked protecting group.

It is preferred that the first reactive functional group be the carboxyl group and the second reactive functional group be the α-amino group. In this method of synthesis, the oligopeptide is synthesized from carboxy-terminus to amino-terminus. The reverse synthetic process can also be used, but is not preferred because stereochemical inversion frequently results.

Usual selectively severable protecting groups for second functional groups of such preferred syntheses are t-Boc and Fmoc. Specific selectively severable protecting groups for other amino acid side chain functional groups-are discussed hereinafter.

At least 6, more preferably at least 10, and still more preferably about 15 to about 20 different amino acid derivatives, are used. cysteine is often omitted because of its reactivity, and coupling of methionine, histidine and tryptophan can sometimes be difficult, with the presence of tryptophan sometimes leading to dimerization when t-Boc protecting groups are used. Cysteine is often omitted when mixtures are made, and tryptophan is usually omitted from mixture-containing positions when t-Boc groups are used.

(c) Each of the containers is placed in a different one of the liquid media and the reactive functional groups of each solid support in each container is therein reacted with a first reactive functional group of a protected amino acid derivative in that respective medium to couple that protected amino acid derivative to the solid support to form a reaction mixture.

(d) Each of the reactions is maintained for a time period and under conditions sufficient for all of the reactive functional groups of the solid support to couple to the protected amino acid derivative to form at least six protected amino acid residue-coupled solid supports.

(e) Each protected amino acid residue-coupled solid support is removed from its respective container. Equimolar amounts of the protected amino acid residue-coupled solid supports are admixed (the physical mixing step) to form a reaction product pool, wherein equal weights of the formed pool contain the same number of moles of each protected amino acid residue-coupled solid support.

The above mixture pool is useful in the stepwise synthesis of a complex mixture of solid support-coupled oligopeptides in which positions other than that occupied by the one or more, predetermined residues of each oligopeptide of the coupled mixture contain an equimolar representation of the at least six different amino acid residues added at each synthesis step. That predetermined one or more amino acid residue is preferably one of the at least six amino acid residues used at the mixture positions and can be present at the terminus of the oligopeptide, e.g. the C-terminus as described here, in which case it is added to the solid support prior to the above steps being carried out, as discussed hereinafter.

The worker using this process will often continue with steps (f)–(k), below, to provide further mixed positions. However, at a predetermined stage in the syntheses, steps (l)–(o) are followed one or more times, and then if desired, steps (f)–(k) are carried out. Regardless of the order of synthesis, each of the sets is prepared having at least one predetermined amino acid residue at at least one predetermined position in the sequence, with at least one other sequence position being occupied by an equimolar mixture of the remaining residues being used.

(f) The reaction product pool is separated into at least six aliquots of equal weight. Each of the aliquots is enclosed in another porous container.

(g) The protecting groups are selectively removed from the second reactive functional groups of the pool to form a reacted product pool having free reactive functional groups. Step (g) can precede step (f).

(h) Each of the enclosed aliquots having free reactive functional groups is placed into one of at least six liquid media, each medium containing a different protected amino acid derivative from a plurality of protected amino acid derivatives from which the oligopeptides are to be formed to form a reaction mixture, wherein each of said protected amino acid derivatives has a first reactive functional group that reacts with the free reactive groups of the enclosed reacted product pool aliquots and a second reactive functional group that is capable of reacting during the reaction of the free reactive functional groups of the pool, but is protected from so reacting by a selectively removable, covalently linked protecting group.

(i) Each of the reactions is maintained for a time period and under conditions sufficient for all of the free reactive functional groups of the enclosed reactant product pool aliquots to couple to the protected amino acid derivative to form at least six solid support-coupled protected amino acid residue reaction products.

(j) Each of the at least six reaction products formed in step (i) is removed, and equimolar amounts of each of those reaction products are admixed to form a reaction product pool. Equal weights of the reaction product pool contain the same number of moles of each reaction product.

(k) Thereafter, steps (f) through (j) are serially repeated zero or more times until a plurality of solid support-coupled reaction product oligopeptides having the desired number of amino acid residues is synthesized.

The equimolarity is only limited by the accuracy in driving the reactions to completion, which typically is 99.5 percent or more, and weighing errors in step (a) and in separating the substantially homogeneously mixed resins into aliquots, which can be done to even greater accuracy with a multigram sample.

At least one specific, predetermined amino acid residue is added at at least one specific position in the oligopeptide chain. The positions in the chain on either side or both sides of the at least one predetermined amino acid residue can contain one or more predetermined amino acid residues, and at least one position, usually more, contains the equimolar mixture of at least six different reacted amino acid residues.

More specifically, using the before-described oligopeptide mixture synthesis, and remembering that enclosure of the solid support is preferred, but not required, (l) each of the protected amino acid derivative-coupled solid supports of steps (e) or (k) is removed from its respective liquid medium, and container where appropriate. Equimolar amounts of protected amino acid derivative-coupled solid supports are admixed to form a further reaction product pool, wherein equal weights of the reaction product pool contain the same number of moles of each reaction product.

(m) An aliquot of the pool formed in step (l), typically all or a majority of the pool, is enclosed in a further porous container.

(n) The protecting groups are selectively removed from the second reactive functional groups to form a reacted solid support pool having free reactive functional groups. Deprotection can again precede enclosure (when used) of the aliquot, and step (m) is omitted where a porous container is not used.

(o) The pool aliquot (enclosed or not) having free second reactive functional groups is placed into a single liquid medium that contains a single, predetermined protected amino acid derivative that is preferably one of the at least six different protected amino acid derivatives discussed before to form a reaction mixture in which the free reactive functional groups and single protected amino acid derivative react, the single protected amino acid derivative having a first reactive functional group that reacts with the free reactive groups of the pool aliquot, and a second reactive functional group that is capable of reacting during the reaction of the free reactive functional groups of the pool aliquot, but is protected from so reacting by a selectively removable covalently linked protecting group.

(p) The reaction mixture is maintained for a time period and under conditions sufficient for all of the free reactive functional groups of the pool aliquot to couple with the single protected amino acid derivative and form a solid support-coupled oligopeptide mixture having a single, predetermined amino acid residue in the same position in the oligopeptide chain.

A complex oligopeptide mixture is provided by following steps (a)–(e) that can be represented by the formula X-B, wherein X represents the equimolar mixture of reacted amino acid residues, and B is the solid support, as before-discussed. Where steps (f)–(k) are followed, and the number of repeats of steps (f)–(j) carried out in step (k) is zero, an oligopeptide pool represented by the formula XX-B is formed. Where steps (f)–(j) are repeated once, an oligopeptide pool represented by the formula XXX-B is formed.

On the other hand, where steps (a)–(e) are followed by steps (l)–(p), a solid support-linked (-coupled) reaction product oligopeptide pool of the formula $O_1$X-B is formed, wherein X and B are as before, and $O_1$ is the single, predetermined amino acid residue. In this instance, the product formed in step (p) is itself a pool because of the pooling of step (e), and therefore when steps (f)–(k) are followed, with zero repeats of steps (f)–(j), an oligopeptide mixture pool is synthesized that corresponds to the formula $XO_1$X-B.

It is also contemplated herein that one can start with equimolar amounts of a predetermined amino acid coupled to the solid support. In this instance, the reactive functional group of the solid support is a free second reactive functional group of an amino acid residue such as an α-amino group. When that is the case, following steps (a)–(e) and steps (f)–(j) once each [zero repeats of steps (f)–(j) in step (k)] the resulting oligopeptide-linked solid support reaction product pool can be represented by the formula $XXO_1$-B. Steps (l)–(p) can then be carried out, or steps (f)–(j) repeated, or both in any order as desired.

It is further contemplated that a set of mixed oligopeptides be produced by following steps (a)–(e) and then (l)–(p). That procedure forms a solid support-coupled product pool of the formula $O_1$X-B. The reaction product of step (p) is itself a pool because of the mixing carried out in step (e), as noted before, so that steps (f)–(j) can be carried out on that product as many times as desired to form a coupled reaction product such as a mixture pool that includes mixed residues at positions 1–4, a specified residue at position 5 and a mixture of residues at position 6.

Once a desired support-coupled set is prepared, the peptide mixtures are deblocked and cleaved from the support, and then reduced to form a linear substituted linear oliogethyleneimine library.

It will be apparent to a worker skilled in this art that several further permutations and combinations of the before-described reactions can be utilized, such as where sets are prepared with a single predetermined residue at position 1 ($O_1$), one each of the at least six residues used at position 2 ($_2$a-f), and a mixture of all six residues at position 3 (X) so that the support-linked reaction product pool can be depicted as $O_1O_{2a-f}$X-B, which can be more generally written $O_1$OX-B. Consequently, no further examples will be provided here.

The physical mixture process and porous containers to hold the solid support particles are summarized schematically and exemplified in FIG. 1 of the drawings. A solid support comprised of a particle such as a resin linked to reactive functional groups 50 is distributed to a plurality of first porous containers shown in the row designed 52 in equal portions of moles of functional group or equal weight portions when a single homogeneous functional group-linked solid support is used. Preferred porous containers are mesh bags or packets discussed hereinafter.

For this example, it will be presumed that there are twenty porous containers in row 52, each labeled 1a–20a respectively, although all twenty are not shown for purposes of clarity, and one need not use all twenty natural amino acids in any study, or one can use more than twenty when non-natural amino acids are included. Each first container in row 52 is then separately placed in a liquid medium containing a single amino acid derivative with appropriate blocking by a selectively removable protecting group and one free, reactive functional group, e.g. a carboxyl group. Each medium contains a different amino acid derivative, so that each container is reacted with a different protected amino acid derivative, as indicated at row 54. Each protected amino acid derivative is then reactively coupled to its respective resin, with all reactions being maintained under conditions and for a time period sufficient for the reaction to go to completion, so that at the end of the reactions, each first container 1a–20a holds a support resin optimally loaded and completely reacted with a related single amino acid derivative.

The coupling reactions are typically driven to completion by adding an excess of the blocked amino acids, and each separate reaction carried out under optimal conditions. It is recognized that each coupling reaction requires different reaction conditions and time to provide full completion. Therefore it is understood that some reactions are completed before others. The earlier-completed reactions can be allowed to sit while the other reactions continue to completion, or, if the reaction products might become degraded, they can be removed from the reaction media and maintained under stabilizing conditions.

The coupling completion can be determined by standard means such as Gisen's picric acid procedure [Gisen, *Anal, Chem. Acta.*, 58:248–249 (1972)], Lebli's bromophenyl blue procedure [Krchnák et al., *Coll. Czech. Chem. Commun.*, 53:2542 (1988)] or by the quantitative ninhydrin test [Savin et al., *Anal. Biochem.*, 117:147–157 (1981)] after removing a small amount of resin from each container. Given the relatively large amount of resin (solid support) used in these reactions, e.g., several grams, removal of milligram amounts of reaction product for assays does not affect equimolarity in the reaction product.

The twenty reacted solid supports, each containing a single reacted amino acid residue, are then removed from the first porous containers 1a–20a and combined in a single vessel 56 (shown in FIG. 1-A and FIG. 1-B for convenience), in which they are thoroughly mixed to form a substantially homogeneous mixture in which the particles of solid support from each of the porous containers 1a–20a are substantially equally distributed throughout the vessel to form a reaction product pool in which equal weights of the pool contain the same number of moles of each reacted solid support.

This mixture pool is then divided into twenty (or another desired number) equal weight second aliquots and one aliquot is placed (enclosed) in each of twenty second porous containers labelled 1b–20b shown in row 58, so that each second porous container 1b–20b now holds reacted solid support particles with all twenty first amino acids equally represented. After suitable amino acid deblocking (deprotection), each of these second porous containers 1b–20b is placed in a separate liquid medium, each medium again containing only one of the twenty amino acids, also appropriately blocked, and containing a free reactive functional group. Further coupling reactions are run to completion in each medium, so that at the end of the second reaction sequence each second container 1b–20b contains reacted solid support particles onto which are attached (coupled) twenty 2-mer chains of amino acids; i.e., twenty first amino acids each coupled to the single second amino acid of this second reaction step. Thus, each porous container holds twenty different 2-mer peptides in essentially equimolar quantities, and the twenty bags in total contain 400 different 2-mer peptides.

The procedure is repeated (reacted solid support removal, thorough mixing, unblocking, placement in twenty new porous containers and reaction of each oligopeptide-linked solid support in each porous container in a different medium with each medium having only a single amino acid) as shown by arrow 60 until the desired number n of steps have been accomplished. At the end of each step the number of n-mer chain oligopeptides in each container is $20^{n-1}$, and the total number of n-mer oligopeptides in all twenty containers is $20^n$. Serially repeating the steps of separating-reenclosing, unblocking reaction with another blocked amino acid derivative, reaction maintenance and pooling steps provides a complex mixture of oligopeptides having the desired number of amino acid residues in length, with each amino acid utilized being present in equal molar amounts of each residue at each position in the oligopeptide chain.

These n-mer protected oligopeptides are deblocked and cleaved from the solid support, e.g., resin, using various methods such as conventional hydrogen fluoride/anisole procedures; see, e.g., Houghten et al., *Intl. J. Peptide Protein Res.*, 16:311–320 (1980). The resulting deblocked, cleaved oligopeptide sets are then reduced to form the oligoethyeneimine library.

The result can be illustrated by taking three of the samples shown in FIG. 1 as representative for descriptive purposes. Sample 1a is first reacted with alanine, and Sample 2a is first reacted with methionine, and Sample 3a is reacted with threonine, yielding the initial chains of:

1a) resin-ala;

2a) resin-met; and 3a) resin-val.

These three are then mixed, divided, e.g., into three aliquots 4b, 5b and 6b, and an aliquot is separately reacted respectively with, arginine, serine, and lysine, yielding three mixtures of 2-mer peptide chains as follows:

| | |
|---|---|
| 1b) | resin-ala-arg, resin-met-arg and resin-val-arg; |
| 2b) | resin-ala-lys, resin-met-lys and resin-val-lys; and |
| 3b) | resin-ala-ser, resin-met-ser and resin-val-ser. |

The total number of different oligopeptides will be seen to be $X^n$, where X represents the number of different amino acids in the initial plurality and n is the number of amino acids in each chain. Thus, with the twenty naturally occurring amino acids as the starting plurality, the process results in $20^n$ different peptide sequences. For example, a chain with a length of six amino acid residues results in $20^6$=64,000,000 different oligopeptide sequences.

Mixtures of peptides can be synthesized with mixtures of at least six to all twenty amino acids or to include D-amino acids or L-, D- or symmetric amino acids at all positions in the sequence but one, with a fixed, single, predetermined amino acid at one position and mixtures in the remaining positions in the peptide chain. An example of a mixture of peptides of this latter sort is the 6-mer peptide mixture pool having alanine in position 1 ($O_1$) and mixtures of residues, $X_{2-6}$, at positions 2–6 so that each $X_n$ represents a mixture of amino acid residues used, yielding a mixture set having 3,200,000 different oligopeptides. The first amino acid can be synthesized on the resin using known methods for single amino acid additions, and the remaining positions are synthesized using the physical mixing process described herein.

B. Chemical Mixture Process

A set of mixed solid support-coupled oligopeptides can also be prepared by chemical mixture means. Here, instead of physically mixing the reacted amino acid residue-coupled solid supports to form equimolar amounts of mixed residues, the amino acid derivatives are mixed in the reaction medium (chemical mixing step) and reacted together with a deprotected second reactive functional group in a single reaction. The resulting oligopeptide-coupled solid support (resin) obtained after each step thus corresponds to the pools discussed earlier.

Such reactions are discussed in Rutter et al. U.S. Pat. No. 5,010,175 and Geysen's published WO 86/00991 (PCT/AU85/00165) published Feb. 13, 1986, whose disclosures are incorporated by reference. Basically, in both of those methods, and the process discussed hereinafter, the protected amino acid derivatives are mixed in the reaction medium in proportion to their relative coupling constants to each other to achieve equimolarity in coupling and then coupled to the reactive functional groups of the solid support or free second reactive functional group of a deprotected residue to form the positions of the mixtures.

The single, predetermined amino acid residues are then added to separate portions of the sequence of mixtures in a manner as discussed previously. The various sets are then kept separated as further mixture positions are added.

Thus, for example, using X, O and B as previously defined, one can synthesize the mixture set XX-B by separate reactions of the mixed reaction mixture with an intervening deprotection step. After separation into aliquots, deprotection and separate reaction with each desired single, predetermined protected amino acid derivative, the solid support-coupled OXX-B product is obtained.

Changing the order of the above reactions, it is readily seen that the solid support-coupled $XO_1X$-B and $XXO_1$-B products can be readily formed. Each of those products is then extended as desired by further single or chemically mixed couplings to form support-coupled pools having at least one predetermined amino acid residue at at least one predetermined position of the oligopeptide chain and equimolar amounts of residues at at least one of the remaining, other positions of the oligopeptide chain.

It should be similarly apparent that longer oligopeptides having at least one predetermined residue further distant from the solid support can also be readily prepared by use of different numbers of reaction/deprotection steps with the chemical mixture of protected amino acid derivatives.

A solid support-coupled pool is then deblocked, cleaved from the support to form an oligopeptide set, and that set is reduced to form a linear substituted oligoethyleneimine library.

Table 1 below provides the amounts of particular protected amino acid derivatives that can be utilized herein, and are reported by Rutter et al. and Geysen above, all α-amino protecting groups utilized are N-t-BOC.

TABLE 1*

| Amino Acid | Example[1] | Rutter et al.[2] | Geysen[3] |
|---|---|---|---|
| Ala | 19 mg | 113 | 32 |
| Asp (Bn) | 33 mg | 238 | 90 |
| Glu (Bn) | 36 mg | 230 | 96 |
| Phe | 20 mg | 177 | 61 |
| Gly | 15 mg | 84 | 27 |
| His (DNP) | 50 mg | 668 | 147 (Tsl) |
| Ile | 123 mg | 667 | 51 (1/2H$_2$O) |
| Lys (Cl-CBZ) | 76 mg | 387 | 124 (CBZ) |
| Leu | 36 mg | 185 | 55 (H$_2$O) |
| Met | 18 mg | 176 | 54 |
| Asn | 37 mg | 171 | 47 |
| Pro | 27 mg | 157 | 42 |
| Gln | 39 mg | 168 | 53 |
| Arg (Tsl) | 82 mg | 286 | 167 (Tsl,H$_2$O) |
| Ser (Bn) | 24 mg | 243 | 76 |
| Thr (Bn) | 44 mg | 451 | 83 |
| Val | 72 mg | 510 | 42 |
| Tyr (Br-CBZ) | 60 mg | 485 | 116 (Bn) |
| Trp | — | 203 | 78 |

*Parenthesized designations in the left column are used by each unless another parenthesized protecting group is shown. Bn = benzyl; DNP = dinitrophenyl; Tsl = toluenesulfonyl; CBZ = benzyloxy carbonyl; Cl-CBZ = o-chlorobenzyloxy carbonyl; Br-CBZ = o-bromobenzyloxy carbonyl.
[1]Milligrams (mg) of each protected amino acid derivative present in a chemical mixture per 1 milliequivalent of resin -NH$_2$ group. Diisopropylcarbodiimide (DIPCD) used as coupling agent. (See Example 2)
[2]Milligrams of each protected amino acid derivative in 6 ml dimethyl formamide (DMF) and 44 ml dichloromethane (DCM). DIPCD used as coupling agent. (U.S. Pat. No. 5,010,175.)
[3]Milligrams of each protected amino acid derivative in 102 ml of DMF. Dicyclohexylcarbodiimide (DCC) used as coupling agent. (WO 86/00991.)

When using Fmoc protecting groups on a cellulose (cotton) solid support, a Fmoc glycine ester is typically first esterified onto the cotton. The remaining available hydroxyl groups are thereafter esterified by reaction of excess acetic anhydride (Ac$_2$O) in the presence of N-methylimidazole (NMI).

After removal of the excess Ac$_2$O and washings, the Fmoc group is removed from the spacer glycine and mixed Fmoc amino acids at 0.3M in DMF are coupled to the support. The mixed Fmoc amino acids typically include all of the naturally occurring amino acids except cysteine. The molar ratios of the Fmoc amino acids in a chemical mixture useful herein are shown in Table 2, below, and can also be used with a particulate support such as a resin or bead.

TABLE 2*

| Amino Acid | Mole Ratio |
|---|---|
| Ala | 0.22 |
| Asp($^t$Bu ester) | 0.47 |
| Glu($^t$Bu ester) | 0.62 |
| Phe | 0.35 |
| Gly | 0.20 |
| His (Tr) | 0.72 |
| Ile | 2.51 |
| Lys ($^t$Boc) | 0.59 |
| Leu | 0.48 |
| Met | 0.34 |
| Asn | 1.65 |
| Pro | 0.20 |
| Gln | 2.03 |
| Arg (Mtr) | 1.98 |
| Ser ($^t$Bu ether) | 0.80 |
| Thr ($^t$Bu ether) | 2.18 |
| Val | 1.85 |

TABLE 2*-continued

| Amino Acid | Mole Ratio |
|---|---|
| Tyr ($^t$BU ether) | 0.81 |
| Trp | 0.99 |

*Parenthesized designations in the left column are protecting groups. $^t$Bu = t-butyl; Tr = trityl; $^t$Boc = t-butyloxycarbonyl; Mtr = 4-methoxy-2,3,6-trimethylbenzenesulfonyl.

The reactions used for these couplings were basically those of Eichler et al., *Peptide Res.*, 4:296 (1991) and also in allowed U.S. patent application Ser. No. 07/645,121, whose disclosures are incorporated by reference, with the exception that a spacer such as $HOCH_2C_6H_4O(CH_2)_3CO_2H$ of that allowed application is usually not utilized. These procedures are discussed in greater detail hereinafter.

This chemical mixture process does not provide exact equimolarity as does the physical mixture process described before. For example, U.S. Pat. No. 5,010,175 reported variation from equimolarity in the range of 0.20–0.32 moles and an average of 0.25±0.04, with each amino acid being no more than 0.8 to 1.28 times the desired result. Deviations from equimolarity from that obtained with the physical mixture method of up to about 35 percent have been observed herein with no adverse effect.

Regardless of the deviations from exact equimolarity observed from use of the chemical mixture method, the various oligopeptides required to obtain enhanced binding by a corresponding oligoethyleneimine are present in large enough quantities to be useful in the assay methods discussed hereinafter.

Once prepared, libraries of any of oliogethyleneimine mixtures can then readily be reacted with a desired acceptor such as a cellular receptor and then assayed for identification of those sequences that react most strongly with the receptor. This assay process can be repeated as many times as desired with different mixture sets to insure that all reasonable candidates for reaction are assayed.

From the identification of the optimum library sequences for reaction and binding, one can prepare an appropriate oligoethyeneimine to be used for the therapeutic treatments of organism dysfunctions that involved that receptor as an acceptor. A number of pharmaceuticals for the treatment of human, animal and plant diseases can be identified and developed in this manner.

It should also be apparent that usual chemical techniques for preparing linear oligoethyleneimines can be used to prepare a contemplated single linear substituted oliogethyleneimine or a library of such compounds. Such techniques are not preferred as they are extremely cumbersome.

In some instances, it can, however, be useful to couple a reagent directly to a deblocked amino group of a free or solid support-coupled oligpeptide. For example, a first-terminal benzyl group can be added to a first-terminal amino group of a support-coupled peptide by reductive alkylation using benzaldehyde and sodium borohydride or by nucleophilic displacement with a benzyl halide such as benzyl bromide, as well as by coupling with benzoic acid followed by the usual reduction process.

C. Termini, Solid SupDorts and CouDling

In preferred practice, each oligopeptide is coupled to the solid support during synthesis by a selectively severable covalent bond, such as an ester or an amide bond. An ultimately produced oligopeptide mixture set is cleaved (separated or severed) from the solid support, recovered and thereafter reduced to form a library of linear substituted oligoethyleneimines.

As noted earlier, each linear substituted oligoethyleneimine contains two to about ten repeating units, and more preferably about five to about eight repeating units so that a corresponding oligopeptide set member contains a chain having two to about ten reacted amino acid residue repeating units. More preferably, each corresponding oligopeptide contains a chain of about five to about eight reacted amino acid residues. The exemplary oligopeptides discussed in detail hereinafter typically contain six reacted amino acid residues, and are referred to as 6-mers.

A $C_1$–$C_{18}$ straight or branched chain acyl group is usually bonded to the N-terminus of an oligopeptide so that after deblocking, cleavage and reduction each member of an oligoethyleneimine library contains a $C_1$–$C_{18}$ straight or branched chain hydrocarbyl group. An acetyl group, a $C_2$ acyl group, is preferred and is often referred to herein as "Ac". Other exemplary $C_1$–$C_{18}$ acyl groups include formyl, propionyl, butyryl, 2-methylpropionyl, hexanoyl, benzoyl, octanoyl, lauroyl, palmitoyl, oleoyl and stearoyl, with their corresponding reduced hydrocarbyl (e.g., alkyl, alkenyl, polyalkenyl, phenyl or alkynyl) groups being methyl, propyl, butyl, 2-methylpropyl, hexyl, benzyl, octyl, lauryl, palmityl, oleyl and stearyl bonded to the nitrogen atom at the first terminus. Hydrogen can also be present at the first terminus of the chains.

A $C_1$–$C_{18}$ acyl group is added by reaction of a corresponding anhydride such as acetic anhydride, acid halide such as octanoyl chloride or by reaction of a suitable activated ester such as N-hydroxysuccinimidyl benzoate. A $C_1$–$C_{18}$ acyl group is usually added to a solid support-coupled oligopeptide upon removal of the selectively removable blocking (protecting) group from the second reactive functional group, when that second reactive functional group is an α-amino group. In preferred practice for oligopeptide syntheses, the second reactive functional group is the N-terminal amino group and the selectively removable protecting group is a t-Boc or Fmoc group, as noted before.

Where an oligopeptide mixture pool is coupled to the solid support by an ester group formed from the C-terminal residue, and a C-terminal amide is desired, the oligopeptide set can be severed from the solid support by aminolysis using ammonia. Cleavage of an ester group-bonded oligopeptide from the solid support using HF results in a C-terminal carboxyl group. Cleavage of an amide-bonded oligopeptide from a benzhydrylamine resin solid support with HF results in the formation of a C-terminal amide group [—C(O)NH$_2$], as is used in the examples hereinafter. Reduction of a C-terminal carboxyl groups of an oligopeptide provides a hydroxyl group at that second terminus, whereas reduction of a C-terminal amido group provides an amino group at the second terminus.

The containers used for syntheses do not appreciably react chemically with and are substantially insoluble in water, acids such as trifluoroacetic acid and anhydrous hydrogen fluoride, bases such as diisopropylethylamine, and organic solvents such as acetone, benzene, toluene, xylene, ethyl acetate, dimethyl sulfoxide, methylene chloride, chloroform, dimethyl acetamide, N-methyl pyrrolidone, dimethyl formamide and the like. Thus, the container is substantially inert to reaction or dissolution with common laboratory liquids. Suitable containers are preferably prepared from polymerized ethylene, propylene and mixtures thereof. Stainless steel and polytetrafluoroethylene can also be utilized for the container. A container can be in rigid shaped form such as closable cylinders or in flexible form such as the sealable bags used in the SMPS process.

Each container includes a sufficient number of foraminae, pores or openings to permit ready entrance and exit of solvent and solute molecules at the reaction temperature, which is typically that of ambient air in a laboratory. For instance, a container can be prepared from a woven mesh, in which the foraminae are the interstices between the woven fiber. Other suitably inactive perforate or porous materials can also be employed, such as a perforated sheet or a non-woven fabric sheet material, either having equal or unequal foraminae. The container material can be substantially completely foraminous (e.g., being formed substantially entirely from mesh materials) or partially foraminous if desired. Containers can be closed in any suitable manner, such as by sealing with liquid-tight lids, heat sealing, and so forth. Subsequent reopening can be by lid removal, cutting of the sealed container, etc.

The foraminae (pores) are of a size that is smaller than any of the enclosed reactive particles. Exemplary polypropylene mesh is available having in interstices of about 35 to about 100 microns. Stated differently, the mesh foraminae are of a size to retain particles that are retained on a 140–400 standard sieve mesh. More preferably, the foraminae are such that particles retained within the foraminae are those that are retained on a 200–400 standard sieve mesh. The foraminae of the containers are large enough to permit draining of all solvents used during a solid phase synthesis within a time period of about five minutes, and more preferably, within a time period of about three minutes, the draining times being measured at the temperature of the organic reaction.

Exemplary foraminous (porous) containers are further described in U.S. Pat. No. 4,631,211, whose disclosures are incorporated by reference.

A container of a synthesis means of this invention encloses a known quantity of solid phase synthesis particles comprised of one or more constituents that includes a covalently linked reactive functional group or a subunit covalently linked to the particle by a selectively severable bond.

Several solid supports containing covalently linked reactive functionalities have been described in the chemical and biochemical literature, and any such support can be utilized so long as the solid support is insoluble in water, in the before-mentioned organic solvents and is substantially chemically inert to the reaction conditions utilized, as discussed before for the containers. The solid support preferably swells in the solvents utilized during the synthesis due to physical, rather than chemical processes.

Perhaps the most utilized particles for oligopeptide syntheses are polymerized resins. The polymerized resins are generally in the form of porous beads.

Of the resins, the hydrophobic polymerized styrene cross-linked with divinyl benzene (typically at about 0.5 to about 2 weight percent) resins are the most often utilized, especially for oligopeptide syntheses. The resin beads so prepared are further reacted to provide a known quantity of a benzyl moiety as a portion of the polymerized resin. The benzyl moiety contains a reactive functional group through which the subunits of the sequence to be synthesized may be covalently linked by a selectively severable bond. Although the reactive benzyl moieties are typically added after the resin bead has been synthesized by reaction of a polymerized styrene moiety, such resins are herein generally described as polymerized styrene cross-linked with divinyl benzene and including a known amount of polymerized vinyl benzyl moiety.

The reactive functionality of the benzyl moiety is typically selected from the group consisting of aminobenzyl and halobenzyl such as chlorobenzyl. Polymerized, cross-linked styrene resins containing chlorobenzyl moieties are sometimes referred to in the art as chloromethyl styrene resins, whereas resins containing aminobenzyl moieties are sometimes referred to as amino-styrene or aminomethyl-styrene resins.

It is noted that the peptide/particle link formed between a particle containing aminobenzyl moiety and a carboxylic acid is not readily cleavable under usual conditions of synthesis. As a consequence, such particles are used with severable linking groups between the particle and first linked subunit, where a free reaction product is desired to be recovered.

Another useful synthetic technique, particularly for use in the chemical mixture process, is the process described in the Lebl et al. allowed U.S. application Ser. No. 07/645,121, whose disclosures are incorporated herein by reference.

Briefly, a planar circular disk is provided having a circular path defined around the disk. The disk is divided into a plurality of individual compartments, each containing an inert porous material such as cotton cloth as a solid support. The compartments are spaced circumferentially along the circular path defined around the disk. At least one functional group for synthesis of an oligopeptide is anchored onto the porous material to form a plurality of individual functionalized compartments.

A dosing head is arranged at a fixed location adjacent the circular path. The dosing head includes means for directly applying measured quantities of at least one liquid component from a common reservoir of the component such as the individual amino acid derivatives or a chemical mixture thereof.

The disk is positioned so that one of the functionalized compartments is positioned to receive a liquid component directly applied by the dosing head. A measured quantity of a liquid component is directly applied to the individual functionalized compartment from the reservoir via the dosing head. The applied liquid component provides an amino acid derivative or mixture to form a covalent bond with the functional group of the functionalized compartment.

The disk is rotated to position another individual compartment along the circular path to receive the same or another liquid component from the dosing head. After the amino acid derivative(s) of each applied liquid component has reacted, or after all have reacted, the disk is spun to centrifugally separate the liquids from the reacted solid support.

A deprotection step follows, followed by further additions of liquid component, reaction, and centrifugation. Those steps are repeated until an oligopeptide of the desired length is prepared.

It should be apparent from the above discussion that the mixture positions of an oligopeptide set can readily be prepared by use of mixed amino acid derivatives. It should be similarly apparent that the single, predetermined amino acid derivative can be similarly added at its predetermined position.

An ester group is typically utilized to link the oligopeptide to the solid support with Fmoc protecting groups. The synthesized oligopeptide is then cleaved with trifluoroacetic acid.

Various useful solid supports, methods of their use, reagents for linking the growing oligopeptide to the support, cleaving an oligopeptide from the support and the like are well known to workers skilled in this art such that further exemplification is unnecessary. Further such exemplifications can, however, be found in U.S. Pat. No. 4,631,211 and in WO 92/09300, published Jun. 11, 1992, whose disclosures are incorporated by reference.

D. Oligopeptide Reduction

Oligopeptide mixture sets are reduced under time, temperature and reductant concentrations sufficient to reduce substantially all of the carbonyl and guanidino bonds present. Guanidino groups of arginine side chains are typically reduced to amine groups of ornithine side chains within the time required for carbonyl group reduction so one need only reduce for the time required for carbonyl reduction to obtain a desired result for both groups. Preferably, reduction is carried out using diborane ($B_2H_6$) in tetrahydrofuran (THF).

A large molar excess of the oligopeptide per each amide bond is typically utilized such as about 10:1 to about 100:1 (moles:mole). Usually used amounts are at a mole ratio of about 40:1 to about 80:1, with usual amount of oligopeptide being about 10–20 mg/ml.

A solvent other than THF can also be used so long as it does not react with the borane such as dimethoxyethane or diethoxyethane. Exemplary commercially available borane-containing compositions include borane-tri-n-butylphosphine, borane-triethylamine and borane-trimethylamine. Use of THF as solvent is preferred because of the ready solvent removal by distillation that is afforded by THF.

The reduction using an above excess of diborane-THF can be carried out at ambient room temperature through reflux temperature (about 65° C.). Typical times for such a reduction at reflux are two to about five days, with about three to about four days being usual and preferred; i.e., about 75 to about loo hours. It is preferred, however, to utilize a temperature below reflux, e.g. about 45–55° C. and a pressurized vessel for this reaction as the usually used THF solvent tends to decompose when kept at reflux for several days.

Upon completion of the carbonyl bond reduction, the excess of diborane is quenched by the addition of an excess of methanol. The methanol forms a volatile compound with boron (trimethyl borate; b.p. 67–68° C.) that can be removed by evaporation under reduced pressure, and forms a 7:3 azeotrope (b.p. 52–54° C.) with methanol.

The diborane reduction process provides a boron-oxygen (for carboxyl groups) or boron-nitrogen (for amides) complex. That complex can be broken and the boron removed by reaction of the boron-containing oligoethyleneimine with a methanolic solution of a strong acid such as HCl, HBr or $H_2SO_4$, HCl being preferred.

In an exemplary synthesis, about 25 milligrams (mg) of solid boron-containing oligoethyleneimine are first shaken with about 5 milliliters (ml) of 2N HCl in methanol. The methanol, HCl and volatile boron compound are then removed under reduced pressure. Another 5 ml of 2N HCl in methanol are added to the residue and the resulting mixture is heated at reflux for about 18 hours (e.g. overnight). The volatile portion is then removed under reduced pressure and another about 5 ml of methanol are added and removed as before. This methanol addition and removal is typically utilized three times. The oligoethyleneimine as a single entity or library (mixture) is then ready for use.

Other methods of reduction can also be utilized as is well known in the art. For example, Raney nickel can be the reductant. In addition, each of the carbonyl oxygen atoms can be replaced by a sulfur atom and that sulfur removed to provide an oligoethyleneimine or oligoethyleneimine library from a corresponding oligopeptide or oligopeptide set. See, for example Raucher et al., *Tetrahedron Lett.*, 21:4061–4064 (1980).

An oligoalkyleneimine or oligoalkyleneimine library can be used in its free amine form. More usually, an individual molecule or library is prepared and used as an acid addition salt of the amine and imine groups present.

Substantially any acid can be used to neutralize the amine and form an addition salt so long as the anion does not react with the alkyleneimine molecules. Hydrochloric acid is preferred. Other exemplary acids include hydrobromic, sulfuric, phosphoric, a $C_1$–$C_{18}$ hydrocarbyl acid such as formic acetic, propionic, iso-butyric, hexanoic, octanoic, decanoic, lauryic, myristic, palmitic, oleic, stearic, benzoic, maleic, fumaric and tartaric acids. It is preferred that the oligoalkyleneimine acid addition salt be water-soluble or water-dispersible.

Where assays are carried out using living cells or organisms, the acid should be non-toxic as to that organism, as is well known. Where living cells are not involved, as in the case of antibody assays toxicity of the acid is not of particular import.

Analytical results with standard acid hydrolytic techniques utilized for amino acid analysis of oligopeptides or proteins when performed on libraries or individual oligoethyleneimines have indicated that all carbonyl groups originally present are not always completely reduced. Some heterogeneity as to carbonyl group content is therefore permitted in a library or individual oligoalkyleneimine.

Those results also indicate that two adjacent peptide bonds are not present after reduction as no identifiable single amino acids have been found. Thus, upon reduction as described hereinbefore, it is sufficient that carbonyl bonds be reduced sufficiently that the library or individual oligoalkyleneimine be free from two adjacent peptide bonds.

The Oligoalkyleneimine Libraries

One aspect of the present invention contemplates a library of linear substituted oligoalkyleneimine chains that comprises a mixture of equimolar amounts of linear oligoalkyleneimine chain members, each member having a first and a second terminus, and containing the same number of two to about ten alkyleneimine repeating units in each chain. Each of the alkyleneimine repeating units has an amino acid side chain bonded to the carbon atom alpha to the nitrogen atom of an alkyleneimine repeating unit. The carboxamide groups of amino acid side chains are replaced by aminomethyl groups, the carboxyl groups of amino acid side chains are replaced by hydroxymethyl groups and the guanidino groups are replaced by amino groups. The members of the library have one or more (at least one) repeating units containing a predetermined amino acid side chain at the same one or more predetermined positions of the oligoalkyleneimine chain. The library also has equimolar amounts of repeating units that contain at least six different amino acid side chains, preferably including the side chain at the at least one predetermined position, at one or more (at least one) of the same other positions of the oligoealkyleneimine chain. A first terminus of each of the oligoalkyleneimines in the library has a hydrogen, benzyl or $C_1$–$C_{18}$ straight or branched chain hydrocarbyl group bonded to an amino group and the second terminus has a hydroxyl or amino group.

A contemplated oligoalkyleneimine library is preferably prepared from a corresponding set of oligopeptides or oligopseudopeptides as where a β-alanine residue is present. For that reason and because peptide nomenclature is well developed and understood whereas nomenclature for oligoalkyleneimines is less developed and cumbersome, exemplary predecessor oligopeptide sets will first be discussed, with that discussion being followed by a discussion of the corresponding oligoalkyleneimine libraries.

Particularly preferred oligoalkyleneimine libraries are oligoethyleneimine libraries, and most of the rest of the following discussion will be directed to oligoethyleneimine libraries as being illustative of the group of oligoalkyleneimines.

A complex mixture pool of solid support-coupled oligopeptides described hereinbefore once deprotected and cleaved or severed from the solid support is referred to herein as an oligopeptide set, an oligopeptide mixture set, by a similar phrase, or more simply as a "set". Being severed from the solid support, an oligopeptide set is unsupported, and because of its method of synthesis, such a set is linear. A corresponding mixture of oligoethyleneimine molecules referred to as a "library", is similarly unsupported and linear.

An oligopeptide mixture set comprises a mixture of equimolar amounts of oligopeptide chains that contain the same number of amino acid residues in each chain; i.e., have the same chain length of 2 to about 10 residues, and more preferably about 5 to about 8 residues. A corresponding linear substituted oligoethyleneimine library is similarly a mixture of oligoethyleneimines of the same length, having the same number of 2 to about 10 repeating units, and preferably 5 to about 8 repeating units;

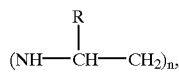

where n is 2 to about 10, and R is the amono acid side chain as discussed before. Inasmuch as each oligoethyleneimine of a library has the same number of repeating units and thus the same length, n is the same for each chain in a library. As noted before, the first terminus of an oligoethyleneimine has a hydrogen, benzyl or $C_1$–$C_{18}$ straight or branched chain hydrocarbyl group bonded to the depicted amino group, whereas the second terminus has a hydroxyl or amino group bonded to the depicted methylene group.

An oligopeptide set has one or more (at least one) predetermined (specifically defined) amino acid residues at the same one or more (at least one) predetermined (specifically defined) positions of the oligopeptide chain and equimolar amounts of at least six different amino acid residues, more preferably at least ten different residues, and most preferably about 15 to about 20 different amino acid residues, at one or more (at least one) predetermined (specifically defined) other positions of the chain, the one or more predetermined residues preferably being one of the at least six different residues present in equimolar amounts. When more than one predetermined amino acid residue is present at more than one predetermined position of the chain, those residues can be the same of different. A corresponding library has one or more (at least one) predetermined reduced amino acid side chain substituents on the same one or more (at least one) predetermined repeating units of the oligoethyleneimine chain, and equimolar amounts of at least six different reduced amino acid side chain substituents at one or more (at least one) predetermined repeating unit positions of the chain.

The number of amino acid residues for the equimolar mixture positions, and thus the number of different sets, is at least six, and more preferably about ten. Most preferably, that number is 15–20. The same is the case for amino acid side chains in a library. It is often preferred to use 18 (t-Boc-synthesized) or 19 (Fmoc-synthesized) sets for each plurality of sets; i.e., the naturally occurring 20 amino acids are used except cysteine that tends to cross-link and tryptophan that is difficult to couple and can also cross-link. However, tryptophan is often used at a predetermined terminal position as the at least one predetermined amino acid residue of a set even though it is not one of the residues utilized at equimolar mixtures positions.

In addition, where it is desired to use tryptophan in a precursor oligopeptide set or library, the tryptophan can be added to a growing solid phase-linked oligopeptide by the use of $N_\alpha$-t-BOC-N-formyl tryptophan that is available from Bachem, Inc., Torrence, Calif. Use of the formyl group protects against the adversed side reactions discussed before.

The N-formyl group can be removed during the usual side chain deprotecting step by the addition of a mercaptan-containing reagent such as ethanedithiol during the "low HF" deprotection reaction discussed herein. The N-formyl group can also be maintained during the side chain deprotection step by omission of the mercaptan-containing reagent during that step in which case that N-formyl group is reduced to a methyl group so that the tryptophan residues of a library or oligoethyleneimine are present as N-methyl tryptophan, as is exemplified hereinafter.

A preferred oligopeptide mixture set contains the one or more predetermined residues at one or more predetermined positions that include a chain terminus, most preferably the N-terminus. A set also includes an equimolar amount of at least six different amino acid residues at one or more predetermined chain positions, and more preferably those chain positions are adjacent to one another. In particularly preferred practice, those adjacent equimolar mixture positions are at a terminus of the oligopeptide chain, and most preferably, that terminus is the C-terminus. Preferably, the same mixture of residues is present at each predetermined position.

In other embodiments, the N-terminal two residues are predetermined residues within the set, the N-terminal three residues are predetermined, or the N-terminal four residues are predetermined when a set is six residues long or longer with the other positions being occupied by equimolar mixtures of residues. Thus, one or more predetermined chain positions at the N-terminus are occupied by predetermined residues and one or more chain positions at the C-terminus are occupied by an equimolar mixture of residues.

In a corresponding library, it is preferred that the one or more (at least one) amino acid side chain-containing repeating units are (is) at the first terminus, with the equimolar side chain mixture positions preferably including the second terminus. It is also preferred that equimolar side chain positions be adjacent to each other.

For a precursor set six residues long or longer, an exemplary oligopeptide mixture set contains equimolar amounts of at least six different amino acid residues at the carboxy-terminal 1, 2, 3, 4 or 5 positions of the oligopeptide chain (i.e., positions 2, 3, 4, 5 and 6 from the amino-terminus of a 6-mer), as specifically defined position(s). At least one other position and preferably more than one other position of the chain of such an oligopeptide mixture set is occupied by a predetermined amino acid residue whose identity is the same at an analogous position within the chain for each set, and those predetermined amino acid residues are most preferably at an amino-terminal position of the chain, including the amino-terminus of the chain. It is to be understood that although the identity of each predetermined residue at a given position in the chain is the same within each set, each such chain position can be occupied by the same or a different residue as between sets.

Exemplary precursor oligopeptide mixture sets include a dipeptide having one position predetermined and the other a mixture; a tripeptide having two positions occupied by predetermined residues and the other a mixture, or vice versa; a tetrapeptide having one predetermined position, e.g. position 1, and three mixture positions; a 5-mer whose first position is defined (predetermined) and whose remaining positions are occupied by mixtures; a 5-mer whose first and fifth positions are defined and whose second, third and fourth positions are occupied by mixtures; a 6-mer whose first two positions are predetermined and whose last four are occupied by mixtures; a hexamer whose first three positions are predetermined and whose last three are occupied by mixtures; a 7-mer whose first position and positions 4–7 are mixtures and whose second and third positions are predetermined; a 7-mer whose first, third and fourth positions are predetermined and whose remaining positions are mixtures; an 8-mer whose third and fourth positions are predetermined and whose remaining positions are occupied by mixtures of residues; an 8-mer whose first four positions are predetermined and whose last four positions are each mixtures; a 9-mer whose fourth and fifth positions are predetermined, and whose remaining positions are mixtures; a 10-mer whose positions 3–7 are predetermined, and whose remaining positions are occupied by mixtures; a 10-mer whose first position is predetermined, with the remaining positions occupied by mixtures; a 10-mer whose positions 7–9 are predetermined, with the remaining positions occupied by mixtures and the like where each mixture is an equimolar mixture of a plurality of coupled amino acid residues that includes at least 6, and more preferably at least about 10, and most preferably about 15 to about 20, different amino acid residues as discussed previously.

Corresponding linear substituted oligoethyleneimine libraries are contemplated for each of the above sets.

Precursor oligopeptide mixture sets that contain two chain positions of predetermined amino acid residues and four or more positions of equimolar mixtures along the chain are among those preferred. For 6-mers, those sets have the configurations of predetermined, single amino acid and equimolar mixtures shown below:

| Predetermined Positions | Mixture Positions |
| --- | --- |
| 1,2 | 3–6 |
| 2,3 | 1,4–6 |
| 3,4 | 1,2,5,6 |
| 4,5 | 1–3,6 |
| 5,6 | 1–4 |
| 1,3 | 2,4–6 |
| 1,4 | 2,3,5,6 |
| 1,5 | 2–4,6 |
| 1,6 | 2–5 |
| 2,4 | 1,3,5,6 |
| 2,5 | 1,3,4,6 |
| 2,6 | 1,3–5 |
| 3,5 | 1,2,4,6 |
| 3,6 | 1,2,4,5 |
| 4,6 | 1–3,5 |

Each of those positional configurations defines 400 mixture sets when the twenty natural amino acids are used. It is preferred that the predetermined residues, O, be adjacent to each other in the chain.

Precursor oligopeptide mixture sets containing three predetermined positions along the chain and three or more equimolar mixture positions are also preferred. Six-mer sets for those preferred sets have the configurations of predetermined, single amino acid and mixtures shown below:

| Predetermined Positions | Mixture Positions |
| --- | --- |
| 1–3 | 4–6 |
| 2–4 | 1,5,6 |
| 3–5 | 1,2,6 |
| 4–6 | 1–3 |
| 1,2,4 | 3,5,6 |
| 1,2,5 | 2,3,6 |
| 1,2,6 | 3–5 |
| 1,3,4 | 2,5,6 |
| 1,4,5 | 2,3,6 |
| 1,5,6 | 2–3 |
| 1,3,5 | 2,4,6 |
| 1,3,6 | 2,4,5 |
| 2,3,5 | 1,4,6 |
| 2,3,6 | 1,4,5 |
| 3,5,6 | 1,2,4 |

Each of the above positional configurations defines 8000 oligopeptide mixture sets when the twenty natural amino acid residues occupy a predetermined position in the chain. It is preferred that the three predetermined positions be adjacent in the chain.

Using the twenty natural amino acids as exemplary, a precursor 6-mer mixture set having only the first position occupied by a predetermined residue has twenty member sets each of which contains 3.2 million member oligopeptides. A precursor set having the first two positions occupied by predetermined residues includes 400 member sets each of which includes 160,000 member oligopeptides. Corresponding linear substituted oligoethyleneimine libraries have slightly fewer member oligoethyleneimine members because both asparigine and arginine form ornithine on reduction and the presence of both causes a redundancy in number of resulting libraries.

The discussion as to precursor oligopeptide sets should be taken to apply to corresponding libraries of linear substituted oligoethyleneimines, including the above-discussed preferences as they apply to corresponding libraries.

In another particularly preferred embodiment, each precursor set comprises equimolar amounts of linear oligopeptide chains containing the same number of two to about ten amino acid residues in each chain. Each set, and its members, have only one, single, predetermined amino acid residue e.g. Ala, D-Val, Ser etc., at a singly predetermined position of the oligopeptide chain, e.g. positions 1, 2, 3 . . . 10 from the amino-terminus.

Thus, each of the plurality of precursor sets has equimolar amounts of the same at least six different amino acid residues at the positions other than that of the single, predetermined amino acid present at the predetermined chain position, and that single residue is preferably one of the same at least six different amino acid residues. Each of the plurality of sets differs from the other sets by the single, predetermined amino acid at the predetermined chain position.

Using a 6-mer corresponding oligopeptide as exemplary, the positions of predetermined, single residue and positions of equimolar mixtures of residues are shown below.

| Predetermined Positions | Mixture Positions |
| --- | --- |
| 1 | 2, 3, 4, 5, 6 |
| 2 | 1, 3, 4, 5, 6 |
| 3 | 1, 2, 4, 5, 6 |

-continued

| Predetermined Positions | Mixture Positions |
|---|---|
| 4 | 1, 2, 3, 5, 6 |
| 5 | 1, 2, 3, 4, 6 |
| 6 | 1, 2, 3, 4, 5 |

There is thus one set of precursor peptides for each of the single, predetermined amino acid residue at position 1. Because at least six amino acid residues are used in the mixture positions and each of those is also preferably used at position 1, the number of the plurality of position-1 sets is six. The same is true for each of the other positions. The sets defined by the position of the single, predetermined amino acid residues can be referred to as positional sets.

These positional sets of 6-mers can also be referred to as 5×sets because of their five mixture positions. Where the peptides are five residues long or have four mixture positions, the sets can be referred to as 4×sets, and so on.

Because there are six positions in the 6-mer, the number of the plurality of plurality of precursor sets for the above group of positional sets is 6 times 6 or 36. There are, however, $6^6$ or 46,656 total oligopeptides represented by that plurality of set pluralities. Use of 20 amino acid residues for the mixture positions of a 6-mer provides 6 times 20 or 120 positional sets, and a total of 64,000,000 individual oligopeptides.

The single, predetermined amino acid at the predetermined chain position is utilized in the equimolar mixture of amino acid residues present at those other positions. If that single, predetermined residue is not present in the mixture positions, the binding assay results of a library of oligoethyleneimines as to that residue lose some meaning as to that residue.

Corresponding linear substituted oligoethyleneimine positional libraries have a single predetermined amino acid side chain at a single predetermined repeating unit position with equimolar amounts of at least six different amino acid side chains at the other repeating unit positions of the chain. Each of the libraries differs from the other libraries by the predetermined amino acid side chain at the predetermined chain position.

It should be apparent from the foregoing discussion that a plurality or library of linear substituted oligoethyleneimines libraries is also contemplated. Each library of the plurality has one or more predetermined amino acid side chains at one or more predetermined repeating unit positions of the oligoethyleneimine chain and the same sequence of equimolar amounts of at least six different amino acid side chains at one or more predetermined repeating unit positions in the oligoethyleneimine chain. The libraries of oligoethyleneimine libraries differ in that at least one predetermined residue present at a predetermined position within each library is different between the libraries. Thus, for example, a 3-mer library of libraries can be depicted as RED-OXX-NH$_2$, where O for each library is $O_a$, $O_b$, $O_c$ etc.

Exemplary libraries of libraries are those corresponding to the previously discussed 400 oligopeptide sets whose first two oligoethyleneimine repeating unit positions are each occupied by one of the twenty naturally occurring amino acid side chains, and the remaining positions 3–6 are occupied by mixtures. Each member of those 400 libraries has two predetermined amino acid side chains ($O_1$ and $O_2$) at one or more predetermined positions (e.g., the first-terminal first two positions) and equimolar amounts of the at least six different residue side chains at one or more predetermined positions (e.g., the four second-terminal positions). One such library is depicted as RED-O$_1$O$_2$XXXX-NH$_2$.

Another exemplary 6-mer library of oligoethyleneimine libraries can be depicted RED-O$_1$O$_2$OXXX-OH where each of the subscripted "O$_{1-2}$"; i.e., "O$_1$" and "O$_2$", is a predetermined amino acid side chain and constant (the same within the library), O is a predetermined side chain that illustratively can be each of the twenty natural amino acid residues, (O$_{a-t}$) and the remaining positions are occupied by mixtures of side chains. Similar libraries of libraries have positions 1–3 occupied by specific predetermined residue side chains, the fourth position occupied by one of the amino acid side chains used in the study, and repeating unit positions 5 and 6 occupied by mixtures of side chains. Another library of libraries has the first four positions defined, the fifth occupied by each of the reduced amino acid side chains used, and the sixth position a mixture.

Thus, the above library of libraries is comprised of member libraries each of which is comprised of a mixture of equimolar amounts of linear substituted oligoethyleneimine chains containing the same number of repeating units in each oligoethyleneimine chain; i.e., here each library has a sequence length of six repeating units. The members of each library have one to four first-terminal positions occupied by the same, single, predetermined amino acid side chain (the $O_1$, $O_2$, $O_3$ etc. positions) and four to one respective second-terminal positions occupied by equimolar amounts of at least six different amino acid side chains utilized (the equimolar mixture positions, X). The single position remaining in each library the position between those enumerated above, is occupied by one each of the amino acid side chains utilized at that position.

The number of libraries within the library of libraries is determined by the number of different amino acid side chains utilized at the above, single remaining position. Thus, where the twenty naturally occurring amino acid residues are used, each library contains 20 mixtures (or nineteen because of the Arg/Asn redundancy). The number of individual oligoethyleneimines in each mixture of a library is determined by multiplying the numbers of substituted repeating units used at each equimolar mixture position.

The linear substituted oligoethyleneimine positional libraries of exemplary 6-mer libraries (obtained by reduction of the previously discussed corresponding 120 6-mer oligopeptide sets) each of which contains one predetermined position and five mixture positions are also contemplated, and illustrate particularly preferred libraries of oligoethyleneimine libraries. Here, again, each library contains a sequence length of six repeating units. one position in each library is occupied by one of at least six of the predetermined amino acid side chain-containing repeating units utilized for that position. The remaining five positions of each library are occupied by equal molar amounts of at least six different amino acid side chain-containing repeating units. Again, the number of members of each library is determined by the number of predetermined side chains utilized, and the number of oligoethyleneimines in each library is determined by multiplying the numbers of side chains utilized at each equimolar mixture position.

The previously discussed mixtures having equimolar amounts of at least six different amino acid side chains occupying the four second-terminal positions also constitute a library of libraries. Here, the libraries contain a sequence length of five to ten substituted repeating units. The first-terminal repeating unit in each library is occupied by each one of the predetermined amino acid side chains utilized at that position (O). The repeating unit sequence between the enumerated first terminus and four second-terminal positions is the same in each library from a second-terminal direction to a first-terminal direction.

Still further libraries of oligoethyleneimines will be apparent to the skilled worker from the previous discussion and need not be gone into further here.

It is presently impossible to assay a mixture the complexity of those described herein. However, by using the synthetic methods discussed before, a skilled worker can construct a mixed precursor oligopeptide set, which upon hydrolysis and amino acid analysis has molar ratios of each amino acid to each other in the range of about 0.5 to about 1.5; i.e., the molar ratio of one amino acid residue to any other residue is 1:1± about 0.5, more preferably, this ratio is 1:1± about 0.25, which ratios carry through to the oligoethyleneimines.

Each chain of a set or library is also present in an equimolar amount and is of the same length (contains the same number of residues or repeating units) compared to the other chains present in the set or library. This equimolarity is also impossible to measure directly. However, by carrying out each reaction to completion and maintaining the previously discussed equimolarity, one can prepare chains that are of the same length and are present in equimolar amounts.

A resin-linked oligopeptide mixture set can also be directly reduced to form a resin-linked oligoethyleneimine library using a before-discussed reduction procedure. Reduction while the peptide/ethyleneimine is linked to the resin facilitates purification of the resulting library from unwanted reaction products.

Such a resin-linked library can then be used in an assay as discussed hereinafter for binding to a soluble reactor such as an antibody or an external cellular receptor such as ELAM1, but is not as useful for general assays for cellular receptors as is a free library. A resin-linked oligoethyleneimine library can also be cleaved using sodium in liquid ammonia, but it is preferred to cleave the peptide first and then reduce it.

A library can also be viewed as a reduced, linear substituted oligoalkyleneamide set, whose alkylene group length, substituent groups and their positions are discussed before and shown in structures. A preferred reduced, linear substituted oligoalkyleneamide set is a reduced linear oliogpeptide set. Such a set will be used illustratively here.

That reduced oligopeptide set comprises a mixture of equimolar amounts of reduced linear oligopeptide chain members, each member having a first and a second terminus, and containing the same number of two to about ten peptide repeating units in each chain. The carboxamide groups of reduced peptide bonds and amino acid side chains are replaced by aminomethyl groups, the carboxyl groups of amino acid side chains are replaced by hydroxymethyl groups and the guanidino groups are replaced by amino groups. The members of the library have one or more (at least one) repeating units containing a predetermined reduced amino acid side chain at the same one or more predetermined positions of the reduced oligopeptide chain. The library also has equimolar amounts of repeating units that contain at least six different reduced amino acid side chains, preferably including the side chain at the at least one predetermined position, at one or more (at least one) of the same other positions of the reduced oligopeptide chain. A first terminus of each of the reduced oligopeptides in the library has a hydrogen, benzyl or $C_1$–$C_{18}$ straight or branched chain hydrocarbyl group bonded to an amino group, and the second terminus has a hydroxyl or amino group.

An individual linear oligoalkyleneimine can similarly be referred to as a reduced linear oligopeptide. Reduced linear oligopeptide sets and individual reduced linear peptides will hereinafter be referred to as linear oligoalkyleneimine libraries and linear individual oligoalkyleneimines, respectively.

It is to be understood that in referring to a contemplated library or individual oligoethyleneimine as a reduced olitopeptide set or reduced linear-oligopeptide, all of the previously discussed preferences as to a library or an individual oligoethyleneimine, and those discussed hereinafter as to the use of a library or individual oligoethyeneimine, apply equally to a reduced linear oligopeptide set or to an individual reduced linear oligopeptide.

It can also be useful for an oligoethyleneimine library to include a label. A radioactive label such as $^3$H can be used as part of an N-terminal acyl group such as an acetyl group that is subsequently reduced to an N-ethyl group.

Other contemplated labels include chromophores such as the 2,4-dinitrophenyl or 4-nitrophenyl groups and fluorescent molecules such as a dansyl group that can be coupled to an N-terminal amino group of an oligoethyleneimine using dansyl chloride (5-dimethylamino-1-naphthalenesulfonyl chloride).

A 2,4-dinitrophenyl or 4-nitrophenyl group can be coupled to a first terminal amine of an oligoethyleneimine library by means of an appropriate halogen derivative such as a chloro or fluoro group. The resulting nitrophenyl aniline derivatives have a yellow to yellow/orange color that can be readily observed.

It is also contemplated that a photoreactive label be coupled to an oligoethyleneimine library, particularly at the first terminus. Exemplary photoreactive labels include the 4-azidobenzoyl and 4-azidosalicyl groups that are present as N-terminal amides prepared by reaction of the N-hydroxysuccinimide ester of either group with the free, first-terminal amino group. Each of the esters is available from Sigma Chemical Co., St. Louis, Mo.

Assay Processes and Oligoethyleneimines

The present invention also contemplates a process for determining the sequence of a linear substituted oligoethyleneimine ligand that preferentially (optimally) binds to an acceptor (receptor). In accordance with one such process, (a) a plurality of libraries of linear substituted oligoethyleneimines in which each library comprises a mixture of equimolar amounts of linear substituted oligoethyleneimine member chains containing the same number of two to about ten reduced amino acid side chain-substituted ethyleneimine repeating units in each oligoethyleneimine chain is provided. As discussed previously, the member chains of each library have one or more (at least one) of at least six different predetermined amino acid side chains at one or more (at least one) predetermined repeating unit positions of the oligoethyleneimine chain, and each library has equimolar amounts of at least six different amino acid side chains at the same one or more (at least one) other positions of the oligoethyleneimine chain. Preferably, the same at least six side chains are used at the mixture positions and the predetermined position. However, in some instances, the one or more predetermined positions of these libraries are occupied by side chain-substituted repeating units not used in the mixture positions. A first terminus of each of the oligoethyleneimines in the library have a hydrogen, benzyl or $C_1$–$C_{18}$ hydrocarbyl group bonded to an amino group, and the second terminus being a hydroxyl or methylamino group, as discussed before. The plurality of libraries differ in that the one or more (at least one) predetermined amino acid side chain present at the one or more (at least one) predetermined chain positions within each library is different between the libraries.

(b) Each library from the plurality of libraries is separately admixed with the acceptor in an aqueous medium at a library concentration of about 0.1 milligrams per liter to about 100 grams per liter, and preferably about 1 milligram per liter to about 100 grams per liter. The binding of each library to the acceptor is separately assayed, and the one or more libraries of the plurality of libraries that exhibits optimal or preferential binding compared to the other libraries assayed is determined, thereby identifying the one or more side chains that provide optimal or preferential binding at that one or more predetermined positions.

(c) A second plurality of libraries of linear substituted oligoethyleneimines is provided in which each library comprises a mixture of equimolar amounts of member linear substituted oligoethyleneimine chains containing the same number of two to about ten repeating units in each oligoethyleneimine chain (having the same chain length) as the chains of first-named plurality of libraries. The members of each second library contain the one or more side chains of the first library identified as exhibiting optimal or preferential binding in the one or more predetermined chain positions occupied in the first-named libraries, and have one of at least six different predetermined amino acid side chains at another preferably adjacent predetermined position of the oligoethylene chain different from the position of the one or more predetermined positions of the first-named plurality of libraries. Each of the second plurality of libraries has equimolar amounts of the same at least six different amino acid side chains as the first-named libraries at the same one or more other positions of the oligoethyleneimine chain not occupied by the one or more identified or predetermined side chains. The first and second termini of the oligoethyleneimines of the second library are the same as those of the first-named library. The second plurality of libraries thus differ from the first plurality of libraries in that at least two chain positions within the second library are identified and. predetermined (defined), and that second library contains one fewer mixture positions.

(d) Each library from the second plurality of libraries (of step c) is separately admixed with the acceptor in an aqueous medium at a concentration of about 0.1 milligrams per liter to about 100 grams per liter and preferably about 1 milligram per liter to about 100 grams per liter. The binding of each second library to the acceptor is separately assayed and the one or more libraries of the second plurality of libraries that exhibits optimal or preferential binding compared to the other libraries assayed is determined, as discussed before, so that another side chain that provides optimal or preferential binding is determined.

(e) Steps (c) and (d) can be repeated with further, e.g., third, fourth, fifth, etc., pluralities of libraries until the desired number of library pluralities, e.g. two through seven, (typically at least three for a 3-mer) have been assayed, each of those library pluralities differing from the immediately previous pluralities by having one more defined (predetermined) repeating unit position occupied by one of at least six predetermined side chains, and one fewer predetermined repeating unit position occupied by equimolar amounts of at least six side chains.

Each of those further plurality of libraries of linear substituted oligoethyleneimines of (e) comprises a mixture of equimolar amounts of member linear substituted oligoethyleneimine chains containing the same number of two to about ten reduced amino acid side chain-substituted ethyleneimine repeating units in each oligoethyleneimine chain as the chains of the first-named plurality of libraries. The member chains of each further plurality of libraries contain the substituent reduced amino acid side chains in the oligoethyleneimine chain positions that exhibited preferential binding in a plurality of libraries used immediately before and also one of at least six different predetermined substituent reduced amino acid side chains at another preferably adjacent predetermined position of the substituted oligoethyleneimine chain that is different from the positions of the identified reduced amino acid side chains of the plurality of libraries used immediately before. Thus, each subsequent plurality of libraries contains each of the previously identified repeating unit substituent side chains in the oligoethyleneimine chain position that exhibited preferential binding as well as a preferably adjacent predetermined repeating unit side chain at a position in the oligoethyleneimine chain previously occupied by an equimolar mixture position. Each of those further pluralities of libraries also has the same termini as the first-named library and has equimolar amounts of the at least six different substituent reduced amino acid side chains of said first-named libraries at the same one or more positions of the substituted oligoethyleneimine chain not occupied by the identified reduced amino acid side chains or the predetermined reduced amino acid side chains.

As noted previously, it is preferred that the one or more predetermined positions of the libraries of (a) are at one or the other terminus of the oligoethyleneimine chain, more preferably the first-terminus. It is also preferred that each new predetermined position in subsequently used libraries be in a position adjacent to the position whose amino acid side chain was identified in the immediately previous assay. Thus, as each of steps (c) and (d) are repeated with new pluralities of libraries, one more position in the sequence becomes identified, and the libraries contain one fewer mixture position.

Once the preferential or optimal binding side chains for all but the last repeating unit position have been determined, at least six individual linear substituted oligoethyleneimine chains are provided. These molecules contain the same number of repeating units and same termini as did the chains of the first-named plurality of libraries, and contain the amino acid side chains in the sequence determined by the above assays; i.e., the molecules contain each of the identified side chains at its position that exhibited preferential binding in the previous assays, and one each of the at least six amino acid side chains used at the final position. These at least six oligoethyleneimines are separately admixed with the acceptor and assayed for preferential or optimal binding as discussed before. Determination of the side chain that exhibits preferential binding as compared to the other side chains assayed from the results of this group of assays provides the last side chain of the sequence and thereby a preferential binding sequence for the linear substituted oligoethyleneimine.

The above assay process is particularly useful with libraries prepared from the before-discussed 400 corresponding 6-mer oliogpeptide sets. Thus, after the first assay, the two first-terminal preferential binding side chains are determined to be from library RED-$O_1O_2$XXXX-$NH_2$, for example. In step (d), the exemplary libraries RED-$O_1O_2$OXXX-$NH_2$ are used, where O represents each of the at least six side chains used as a group, and a preferential binding side chain ($O_3$) is determined to be present in library RED-$O_1O_2$OXXX. Libraries RED-$O_1O_2O_3$OXX-$NH_2$ are then used to determine an optimal side chain for repeating unit 4 ($O_4$), followed by libraries RED-$O_1O_2O_3O_4$OX-$NH_2$ used to determine the an optimal binding side chain at postion $O_5$. Individual oligoethyleneimines RED-$O_1O_2O_3O_4O_5$O-$N_2$ are used to complete the determination of the overall preferential binding sequence by determining optimal binding side chain $O_6$.

Also preferred are libraries 5–10 repeating units in length whose corresponding C-terminal (second-terminal) four positions are occupied by amino acid residue side chain mixtures, and whose corresponding amino-terminal (first terminus) positions are occupied by predtermined residue side chains. Each above library can be prepared from a single preparation of solid support-coupled 4-mer oligopeptide mixtures to which one or more predetermined acid residues is coupled, then deblocked, cleaved and reduced following each acceptor binding assay.

For example, starting with a batch of support-coupled 4-mer oligopeptide mixtures whose positions are all equimolar mixtures, twenty mixtures can be prepared by separately coupling each of the twenty natural amino acids to a separate portion of the batch. After deblocking, cleavage and reduction, a binding assay is run as with a monoclonal antibody to determine preferential binding. Another set of twenty is then prepared using the same batch with an optimal binding residue at position 2 in the sequence from the corresponding N-terminus (first terminus in a library) and each of the twenty residues at position 1. The binding assay is run again after deblocking, cleavage and reduction, and optimal binding is determined. This process is continued until a predetermined oligoethyleneimine sequence of desired length is completed.

Another particularly preferred assay process utilizes libraries prepared from corresponding positional oligopeptide sets, such as the 120 precursor 6-mer sets. Here, (a) a plurality of libraries of linear reduced amino acid side chain-substituted oligoethyleneimines in which each library comprises a mixture of equimolar amounts of linear reduced amino acid side chain-substituted oligoethyleneimine chains containing the same number of two to ten repeating units in each oligoethyleneimine chain is provided. As discussed previously, the members of each library have one of at least six different predetermined amino acid side chains at a single predetermined repeating unit position of the oligoethyleneimine chain, and first and second termini as discussed before. Each library has equimolar amounts of those same at least six different amino acid side chains at the same other positions of the oligoethyleneimine chain. As is the case with all of the libraries discussed herein, it is preferred to use about 10 or more and more preferable to use about 15 to about 20 different amino acid side chains. The plurality of libraries differ in that the single predetermined amino acid side chain present at a single predetermined chain position within each library is different between the libraries.

(b) Each library from the plurality of library is separately admixed with the acceptor in an aqueous medium at a library concentration of about 0.1 milligrams per liter to about 100 grams per liter, and preferably about 1 milligram per liter to about 100 grams per liter. The binding of each library to the acceptor is separately assayed, and the one or more libraries of the plurality of libraries that exhibits preferential binding compared to the other libraries assayed is determined, thereby identifying the one or more side chains that provide preferential binding at that single, predetermined position.

(c) A second plurality of libraries of linear substituted oligoethyleneimines is provided in which each library comprises a mixture of equimolar amounts of linear substituted oligoethyleneimine chains containing the same number of two to ten repeating units in each oligoethyleneimine chain (having the same chain length) as the first-named plurality of libraries. The members of each second library have the same first and second termini as the first library number chains, and have one of the same at least six different predetermined amino acid side chains of the first-named libraries at another single predetermined position of the oligoethylene chain different from the position of the first-named plurality of libraries, and each of these libraries has equimolar amounts of the same at least six different amino acid side chains at the same other repeating unit positions of the oligoethyleneimine chain. The second plurality of libraries differs from the first plurality of libraries in that the single predetermined chain position within each library that contains the one of at least six different residue side chains is different between the libraries. Put differently, the second plurality of libraries has the same termini as the first-named library, and has equimolar amounts of the at least six side chains at a oligoetheyleneimine chain position occupied by the single side chain in the first-named library plurality, and a single side chain in a position occupied by equimolar amounts of side chains in the first-named libraries. For example, the first named plurality of libraries can have its single one of at least six different predetermined amino acid side chains at position 1, whereas this second plurality of libraries has its single predetermined amino acid side chain at any of positions 2–10, and equimolar amounts of at least six different side chains at position 1.

(d) Each library from the second plurality of libraries (of step c) is separately admixed with the acceptor in an aqueous medium at a concentration of about 0.1 milligrams per liter to about 100 grams per liter and preferably about 1 milligram per liter to about 100 grams per liter. The binding of each second library to the acceptor is separately assayed and the one or more libraries of this second plurality of libraries that exhibits preferential binding compared to the other libraries assayed is determined, thereby identifying a reduced amino acid side chain that provides preferential binding at that predetermined position in the oligoethyleneimine chain.

(e) Steps (c) and (d) are repeated with third, fourth, fifth, etc., pluralities of libraries until the desired number of library pluralities have been assayed, each of those library pluralities differing from the other pluralities by the position that contains the one of at least six different amino acid side chains. It should also be apparent that where diethyleneimines are used, the process is stopped so that steps (c) and (d) can be repeated zero times.

The identity and position of the amino acid side chain of each one or more libraries that provided preferential or optimal binding so determined for each plurality of libraries provides the identity of a repeating unit sequence for the ligand that preferentially binds to the acceptor. Thus, because each of the pluralities of positional libraries assayed provides the identity of a residue(s) that provide(s) enhanced binding for that position, and because there is equimolar representation of all the other side chains at the mixture positions, knowledge of the identity and position of side chains that provide enhanced binding for the utilized positions provides a sequence for a ligand or donor-substituted oligoethyleneimine that provides enhanced binding.

It should be understood that determining the identity and position of two side chains that each provide greatly enhanced binding can be extremely useful when preparing completed reduced peptides because several fewer such reduced peptides need be prepared. Of course, knowledge of three identities and positions is more preferred, and knowledge of four is more preferred still, etc.

The above process is referred to as a scanning synthetic ethyleneimine combinatorial library (SECL) process in that side chains at each position of a sequence are individually scanned.

It is preferred that, as a group, the single, predetermined repeating unit positions be adjacent to each other. Thus, exemplary libraries for positions 1–3 of a trimer, or positions 2–6 of a hexamer are used or 1–6 of a decamer oligoethyleneimine are used.

It should be understood that although it is preferred to scan adjacent repeating unit positions, one need not utilize the pluralities of libraries in any order by position. Thus, although convenient, one need not use the plurality of libraries that contain the one of at least six different predetermined side chains at position 1 followed by the libraries having the one of at least six different predetermined side chains at position 2, and so on.

In addition to there being no need to utilize the pluralities of positional libraries in any order, it is also not necessary to utilize a single plurality of positional libraries followed by another and another, etc. Rather, one can utilize the individual libraries in any order because the position and identity of the single one of at least six different predetermined amino acid side chains of each library is known. This is in contrast to the previously discussed process where it is preferred to use a predetermined side chain adjacent to an identified side chain.

Thus, a more general scanning SECL process is also contemplated. Here, (a) separate pluralities of libraries of linear substituted oligoethyleneimines are provided. Each library of those pluralities of libraries comprises a mixture of equimolar amounts of linear substituted oligoethyleneimine chains containing the same number of two to about ten repeating units in each chain, and having a hydrogen, benzyl or $C_1$–$C_{18}$ hydrocarbyl group bonded to the amino group of the first terminus and having a hydroxyl or methylamino group as the second terminus. Each library has a single one of at least six different predetermined amino acid side chains at a single, predetermined repeating unit position of the oligoethyleneimine chain, and has equimolar amounts of each of the same at least six different amino acid side chains at the same other positions of the oligoethyleneimine chain. Each library differs from the other libraries in that the identity and chain position of the one of at least six different predetermined amino acid side chains present at the single predetermined repeating unit chain position within each library is different between the libraries. The maximum number of libraries provided is equal to the product of the number of different amino acid side chains present at the predetermined chain positions containing the one of at least six different side chains times the number of different chain positions containing the one of at least six different predetermined amino acid side chains.

(b) Each library is separately admixed with the acceptor in an aqueous medium at a library concentration of about 0.1 milligrams per liter to about 100 grams per liter and preferably about 1 milligram per liter to about 100 grams per liter. The binding of each library to the acceptor is separately assayed for each library. The one or more libraries that provide preferential binding for each different chain position is determined.

The identity and position of the repeating unit containing an amino acid side chain of each one or more libraries that exhibited preferential binding provides the side chain sequence for the ligand that preferentially binds to the acceptor.

Although an above process can be carried out with diethyleneimine libraries, it is preferred to use libraries of at least pentamers. Thus, at least five pluralities of positional libraries are typically utilized (scanned). It is preferred, but not necessary, that those five pluralities of libraries, as a group, contain single, predetermined side chains at adjacent positions in the sequence. For example, in a 5-mer, those positions would be 1–5 of the sequence. However, in a 10-mer, those positions could be positions 6–10, 5–9, 3–7 or the like. Of course, one obtains more precise sequence identification information if adjacent positions of the oligoethyleneimine chain are determined, and if the identity of the side chain exhibiting enhanced binding for each chain position is determined.

Those identified side chains that exhibit preferential binding within about a factor of two of a best binding side chain at that position are typically considered to exhibit preferential or optimal binding and are used to prepare a series oligoethyleneimines using the other identified side chains at the other positions to determine which combination provides optimal or preferential overall properties. Thus, using a 6-mer as exemplary, although one may not be able to determine a single optimal sequence out of the 64,000,000, the field is typically cut down to about 5–50 or sometimes thousands of sequences, which because of their sequential similarity, can be readily prepared by the SMPS method discussed in U.S. Pat. No. 4,631,211, followed by reduction. Even where the scanning SECL process narrows the possible optimal binding linear substituted oligoethyleneimine sequences to several thousand, the worker's knowledge has been advanced, and he or she can use a peptide synthesis method described in WO 92/09300, or Houghten et al., Nature, 354:84 (1991), in U.S. Pat. No. 5,010,175 or in WO 86/00991 followed by reduction to complete the sequence or obtain new optimal binding sequences.

In any assay discussed herein, all of the at least six different predetermined side chains at a predetermined position can provide similar binding. That phenomenon is referred to as positional redundancy or redundancy, and any convenient side chain is utilized at that position when an oligoethyleneimine ligand is synthesized.

The aqueous medium used in an assay can be extremely varied and includes tap water, distilled or deionized water, as well as a buffer solution as is used for antibody binding studies or a cell growth medium as is useful for culturing bacteria, yeast, fungi, plant or animal cells, all of which are well known to skilled workers.

The concentration of an linear substituted oligoethyleneimine library in the aqueous medium is selected so that the oligoethyleneimine library is present at concentrations of about 0.1 milligrams per liter to about 100 grams per liter and preferably about 1.0 µg/ml to about 100 mg/ml. Thus, when each oligoethyleneimine mixture is made up of 3.2 million individual oligoethyleneimines; i.e., a reduced N-acetyl C-amide 6-mer oligopeptide using the 20 natural amino acid residues, then each 6-mer oligoethyleneimine within each mixture is present in a preferred concentration of about 1.0 µg/ml/3,200,000=0.31 pg/ml, to about 100 mg/ml/3,200,000=31.25 ng/ml. Presuming an average molecular weight of a reduced N-acetyl C-amide 6-mer peptide (a 6-mer oligoethyleneimine) to be 687 gm/mole as a free base, then at 1.0 µg/ml, the individual hexamers are present at a concentration of about 0.5 pmolar and at 100 mg/ml the individual hexamers are present at about 50 nmolar. More preferably, concentrations of about 0.5 mg/ml to about 10 mg/ml are used.

It is to be understood that the wide breadth of concentrations specified above is intended to take into account the contemplated range of oligoethyleneimine libraries that can have up to nine positions as mixtures, and the fact that wide ranges of concentrations are often used for determining $IC_{50}$ and $K_i$ values. It is also to be understood that when present as an acid addition salt, as is usually the case for a library used in a process disclosed herein, the molecular weight of each oligoethyleneimine salt is greater than that noted above for the free base so that the molarity of individual oligoethyleneimine chains per a given weight amount is still less.

An oligoethyleneimine library and its individual members can be looked at as donor (ligand) in donor-acceptor (receptor) binding complex formation. Exemplary acceptor molecules are antibody combining site-containing molecules such as whole antibodies, F(ab), F(ab')$_2$ and Fv antibody portions, solubilized or non-solubilized cell surface receptor molecules, internal cellular receptors and viral protein receptors, all but the antibody combining site-containing molecules being collectively referred to as "cellular receptors". "Cellular receptors" also include living cells that contain receptors that interact with an oligoethyleneimine library as ligand (donor).

Any well known binding or binding inhibition assay format can be used. For example, a solid phase assay using a solid phase-bound antibody binding site and a radiolabeled oligoethyleneimine library is contemplated. Also contemplated is a competitive binding assay in which a protein or polypeptide is bound to a solid phase as an antigen and a monoclonal antibody binding to that antigen is admixed with an oligoethyleneimine library. Inhibition of binding of the monoclonal antibody by the oligoethyleneimine library provides a measure of the binding between the oligoethyleneimines and monoclonal antibody. Monoclonal antibody binding inhibition and the inhibition of other acceptors' binding can be assayed using enzyme or radiolabels as is well known.

It is often the case that one has receptors (acceptors) such as antibodies to a particular ligand such as an antigen, but the specific ligand (antigen) that binds those antibodies is unknown. Under these circumstances, usual solid phase assay in which the ligand is affixed to a plate or other solid phase matrix cannot be carried out because the relatively short oligoethyleneimine libraries contemplated herein do not bind well to microtiter plate walls and similar solid phase matrices.

Avidin binds well to microtiter plate walls and similar matrices. Use of that fact and its well known binding partner, biotin, can be made for those assays in which the ligand bond by the receptor is unknown or is otherwise unavailable.

Thus, avidin is coated on a solid phase matrix such as microtiter plate walls using standard, well known techniques such as adsorption. Biotin, which contains a free carboxyl group, is coupled to the first-terminal amine of a before-described oligoethyleneimine library via the biotin carboxyl group, using usual coupling chemistry as described herein for coupling amino acids. The biotinylated library is dissolved in an aqeuous medium and admixed with the avidin-coated solid phase matrix to form a solid/liquid phase admixture. That admixture is maintained for a time period sufficient for the avidin and biotinylated oligoethyleneimine library complex, typically five minutes to about five hours, and form a biotinylated oligoethyleneimine library-containing solid support and a liquid phase depleted of biotinylated oligoethyleneimine. The solid and liquid phases are then separated, and the solid support is typically washed.

The thus prepared solid support that contains an affixed oligoethyleneimine library, is then utilized with the receptor (acceptor) in standard solid phase assays. Where the receptor is an antibody, usual detecting systems such as the use of radiolabeled or enzyme-linked anti-antibodies such as goat anti-mouse antibodies where the receptors are mouse antibodies are utilized to detect binding. Where the receptor is a cellular receptor, radiolabels incorporated into the receptor by culture of the cells in a medium containing radioactive amino acids are typical detecting means of choice.

It is frequently convenient to provide a spacer group between the oligoethyleneimine library and the biotin. Exemplary spacers include one to about five glycine, $C_2$–$C_6$ straight chain ω-amino acids such as glycine, α-alanine, 4-aminobutyric acid (GABA) or 4-aminocaproic acid.

Thus, a N-terminal biotinylated oligoethyleneimine library as otherwise described before is also contemplated. That biotinylated oligoethyleneimine library can further include one to about five $C_2$–$C_6$ straight chain ω-amino acid residues between the first terminal amine of the oligoethyleneimines and the biotin group.

For a before-discussed chromophore- or fluorescent-labeled oligoethyleneimine library, contact between the acceptor and oligoethyleneimine library can be carried out with the acceptor linked to a solid support such as sepharose or agarose. The non-binding and poorer binding libraries can be separated from the solid support-bound acceptor molecules by washing at increasingly higher salt concentrations until a predetermined concentration is reached that is used to define a better or preferential binding oligoethyleneimine. The choromophoric or fluorescent label can be used to follow the elution. Using the 2,4-dinitrophenyl chromophore as exemplary, the presence of a yellow to yellow/orange color on the solid support for a given library after washing indicates an optimal binding library.

An exemplary assay using a photoreactive label can be carried out with an enzyme having a known substrate. Here, the enzyme as acceptor and photoreactive labeled-oligoethyleneimine library are admixed and the admixture maintained so that binding can occur. The admixture is then irradiated using sufficient quanta of light at an appropriate wavelength, as are well known, to cause the decomposition of the photoreactive group such as an azide group and the insertion of the resulting oligoethyleneimine-containing radical into the enzyme polypeptide backbone. That insertion links the oligoethyleneimine to the enzyme and blocks reaction with the enzyme's substrate. Thus, an assay of enzymic activity after irradiation provides a determination of which oligoethyleneimine library bound optimally, with a diminished activity indicating enhanced binding.

Cellular receptor molecules are also particularly contemplated as useful in this assay system. The cellular receptor whose binding is contemplated for assay need not be isolated, but can be part of an intact, living cell such as bacterial, yeast, fungal, mammalian or plant cells, or viruses. When such intact, living cells are utilized, relative binding amounts can be determined by the growth or inhibition of growth of the admixed, assayed cells. The aqueous medium here is a growth or culture medium, known to promote growth of the assayed cells.

The concentration of free acceptor molecules, including those obtained from cell preparations or those present in intact, living cells used for such binding assays is an assay-effective amount such as is normally used for such assays, and is well known in the art. It is to be understood that different concentrations of free acceptor molecules or those present in intact, living cells can vary with each acceptor studied.

A before-described assay can be carried out in vitro as is specifically illustrated hereinafter, as well as being carried out in vivo. For in vivo assays, living plants such as tobacco, alfalfa, corn (maize), zinnias and the like are contemplated hosts, whereas small laboratory mammals such as rats, mice, guinea pigs, rabbits and dogs are contemplated hosts for animal assays.

An oligoethyleneimine library-containing composition can be administered and an oligoethyleneimine contacted with the acceptors internally or externally in plants through watering, misting of foliage, or injection. For the animals, a composition can be administered internally, orally or by injection such as intraperitoneally, subcutaneously or intramuscularly or topically as by application to skin for the contact between donor and acceptor to take place.

Binding here can be assessed by relative growth rate (positive or negative) or by the affect of the composition on one or more tissues, as through microscopic examination, by body temperature where pathogen-infected animals are used, and the like as are well known.

The following examples are intended to illustrate, but not limit, the invention.

EXAMPLE 1

Exemplary Synthesis of a Set of Mixed Oligopeptides having Equimolar Amounts of the Twenty Natural Amino Acid Residues Aliquots of five grams (4.65 mmols) of p-methylbenzhydrylamine hydrochloride resin (MBHA) are placed into twenty porous polypropylene bags. These bags are placed into a common container and washed with 1.0 liter of $CH_2Cl_2$ three times (three minutes each time), then again washed three times (three minutes each time) with 1.0 liter of 5 percent $DIEA/CH_2Cl_2$ (DIEA=diisopropylethylamine). The bags are then rinsed with $CH_2Cl_2$ and placed into separate reaction vessels each containing 50 ml (0.56 M) of the respective t-Boc-amino acid/$CH_2Cl_2$. N,N-Diisopropylcarbodiimide (DIPCDI; 25 ml; 1.12 M) is added to each container, as a coupling agent.

Twenty amino acid derivatives are separately coupled to the resin in 50/50 (v/v) $DMF/CH_2Cl_2$. After one hour of vigorous shaking, Gisen's picric acid test [Gisen, *Anal. Chem. Acta*, 58:248–249 (1972)] is performed to determine the completeness of the coupling reaction. On confirming completeness of reaction, all of the resin packets are then washed with 1.5 liters of DMF and washed two more times with 1.5 liters of $CH_2Cl_2$.

After rinsing, the resins are removed from their separate packets and admixed together to form a pool in a common bag. The resulting resin mixture is then dried and weighed, divided again into 20 equal portions (aliquots), and placed into 20 further polypropylene bags (enclosed). In a common reaction vessel the following steps are carried out: (1) deprotection is carried out on the enclosed aliquots for thirty minutes with 1.5 liters of 55 percent $TFA/CH_2Cl_2$; and 2) neutralization is carried out with three washes of 1.5 liters each of 5 percent $DIEA/CH_2Cl_2$.

Each bag is placed in a separate solution of activated t-Boc-amino acid derivative and the coupling reaction carried out to completion as before. All coupling reactions are monitored using the above quantitative picric acid assay. Next, the bags are opened and the resulting t-Boc-protected dipeptide resins are mixed together to form a pool, aliquots are made from the pool, the aliquots are enclosed, deprotected and further reactions are carried out.

This process can be repeated any number of times yielding at each step an equimolar representation of the desired number of amino acid residues in the peptide chain. The principal process steps are conveniently referred to as a divide-couple-recombine (DCR) synthesis.

After a desired number of such couplings and mixtures are carried out, the polypropylene bags are kept separated to here provide the twenty sets having the amino-terminal residue as the single, predetermined residue, with, for example, positions 2–4 being occupied by equimolar amounts of the twenty residues. To prepare sets having the single, predetermined amino acid residue at other than the amino-terminus, the contents of the bags are not mixed after adding a residue at the desired, predetermined position. Rather, the contents of each of the twenty bags are separated into 20 aliquots, deprotected and then separately reacted with the twenty amino acid derivatives. The contents of each set of twenty bags thus produced are thereafter mixed and treated as before-described until the desired oligopeptide length is achieved.

The side chain protecting groups used with α-amino-terminal t-Boc and Fmoc protecting groups are usually different. The side chain protecting groups utilized for one type of synthesis or the other are as shown in the table below. Other usually used side chain protecting groups are also utilized for both types of syntheses.

| | Side Chain Protecting Group | |
| --- | --- | --- |
| Amino Acid Derivative | N-t-Boc Protected | N-Fmoc Protected |
| Arginine | Toluenesulfonyl* | Mtr** |
| Cysteine | p-Methoxybenzyl | t-Butyl ether |
| Glutamic acid | O-Benzyl | t-Butyl ester |
| Histidine | N-im-dinitrophenyl* | Trityl |
| Lysine | N-(o-chlorobenzyl-oxycarbonyl) | t-Boc |
| Serine | O-Benzyl | t-Butyl ether |
| Threonine | O-Benzyl | t-Butyl ether |
| Tyrosine | O-(m-bromobenzenyl-oxycarbonyl) | t-Butyl ether |
| Aspartic acid | O-Benzyl | t-Butyl ester |

*Arginine and histidine are coupled in the presence of N-hydroxylbenztriazole [Hruby et al., Angew. Chem. Int. Ed. Engl., 10:336–339 (1971)].
**Mtr = 4-Methoxy-2,3,6-trimethylbenzenesulfonyl.

For oligopeptide mixture sets not having an N-terminal $C_1$–$C_{18}$ acyl (e.g. acetyl) group, the following procedure is used for side chain deprotection of N-t-Boc-protected oligopeptide chains. The fully protected solid support-coupled oligopeptide mixtures are treated with 55 percent trifluoroacetic acid in methylene chloride prior to the HF treatment to remove the final t-Boc-protecting group. Then the protected solid support-coupled oligopeptide mixtures, in polypropylene mesh packets [Houghten, *Proc. Natl. Acad. Sci., USA*, 82:5131–5135 (1985)] are rinsed with alternating washes of $CH_2Cl_2$ and isopropanol, and dried under reduced pressure for twenty-four hours.

The low HF step [Tam et al., *J. Am. Chem. Soc.*, 195:6442–6455 (1983)] is carried out in a two liter polypropylene reaction vessel, using a solution of 60 percent dimethylsulfide, 25 percent HF, 10 percent p-cresol and 5 percent ethylenedithiol. The ethanedithiol is used to cleave the N-formyl groups from tryptophan residues. Where it is desired not to cleave the N-formyl groups, ethanedithiol is omitted from the mixture and its amount is replaced by HF. $N_\alpha$-t-BOC-N-formyl tryptophan is available from Bachem, Inc., Torrence, Calif.

HF is condensed at −78° C. After condensation, the HF-scavenger solution is carefully transferred to the reaction vessel that contained the resin-containing packets. The low HF solution is made to give 5 mls per 0.1 mmol of oligopeptide. After the reagents are added, the reaction vessel is placed in an ice water bath and shaken for two hours. The low HF solution is removed and the packets containing the deprotected peptide resins are quickly washed with chilled $CH_2Cl_2$. The $CH_2Cl_2$ wash is repeated nine times (one minute each) followed by ten alternating washes of isopropanol and $CH_2Cl_2$. Finally, the resin is washed five times with DMF, then twice more with $CH_2Cl_2$. Deprotected peptide resin packets are dried under reduced pressure. After this process is completed, the unprotected peptides are ready to be cleaved by anhydrous HF.

The N-terminal Fmoc protecting groups of enclosed, protected solid support-coupled oligopeptide mixtures are removed by treatment with twenty percent piperidine in DMF for ten minutes. Then the resulting N-deprotected, side chain-protected peptide resins in polypropylene packets are washed with DMF twice (five minutes each) followed by two rinses with $CH_2Cl_2$ (one minute each) and dried in a vacuum for twenty-four hours. Although porous containers are not utilized, each solid support-coupled reaction product must still be maintained separately during reactions.

The side chain deprotection is carried out in a two liter polypropylene reaction vessel, using a solution of 85 percent TFA, 5 percent phenol, 4 percent thioanisole, 4 percent deionized $H_2O$ and 2 percent ethanedithiol. The resins are shaken for 3.5 hours at room temperature. The reaction solution is removed, and the packets containing the completely deprotected solid support-coupled oligopeptide mixtures are quickly washed with chilled ether. The ether wash is repeated nine times (one minute each) followed by ten alternating washes of isopropanol and $CH_2Cl_2$. Finally, the solid support-coupled oligopeptide mixtures are washed five times with DMF, then twice more with $CH_2Cl_2$. Deprotected solid support-coupled oligopeptide mixtures and their enclosing packets are dried under reduced pressure. After this process is completed, the unprotected peptides are ready to be cleaved by anhydrous HF.

Where an N-acyl group such as an acetyl group is to be present on an oligopeptide mixture set, the final t-Boc or Fmoc protecting group is removed as above, an excess of acetic anhydride is added and the reaction is maintained until there are no more free amino groups present as discussed elsewhere herein. The above rinsing and drying steps are then carried out, followed by deprotection and cleavage of the oligopeptide mixture set from the solid support.

As noted earlier, use of a benzhydrylamine resin as a solid support and anhydrous HF/anisole for cleavage of the oligopeptide mixture set provides a C-terminal amido group for the oligopeptide mixture set produced. Use of a benzhydrylalcohol resin solid support and that cleavage procedure provides a C-terminal carboxylic acid. Use of a disulfide-containing linking group between the solid support and oligopeptide chains and cleavage with a disulfide bond breaking agent as discussed provides a C-terminal mercaptan linking group amide-bonded to the oligopeptide chains.

Reaction at reflux for 3 to 4 days of the resulting oligopeptide set in a sufficient volume of 1M diborane-THF to provide an about 25:1 molar ratio of diborane to carbonyl groups present provides a corresponding linear substituted oligoethyleneimine library after work-up, as discussed before.

EXAMPLE 2

Chemical Mixture Synthesis

These syntheses using 18 of the 20 naturally occurring amino acid derivatives (Cys and Trp omitted) are carried out substantially as described in U.S. Pat. No. 4,631,211 and Example 1.

A cross-linked polystyrene resin is used as solid support that also included 0.93 milliequivalents (meq) of benzhydrylamine groups per gram. The solid support resin is typically utilized in an amount of 300 milligrams (mg) so that 2.79 meq of resin-amine are initially provided in each reaction.

The mixture of amino acid derivatives noted in Table 1 at 0.5M in 4 ml of dimethylformamide (DMF) is used for each coupling, as about a 7-fold molar excess over the amount of amine present, as resin-amine or after deprotection to provide N-terminal amine (free amine) groups. One equivalent of DIPCDI as coupling agent and one equivalent of N-hydroxylbenztriazole-$H_2O$ are used per equivalent of mixed amino acid derivative, so both are also present in about a 7-fold excess over the free amine groups present.

Each coupling is carried out at room temperature until there is no remaining free amine groups as in Example 1; about one hour. Deprotection and neutralizations are also carried out as in Example 1.

Each position containing equimolar amounts of amino acid residues is added as described above. Using a 6-mer SECL whose fifth position is occupied by one of eighteen predetermined amino acid side chains as exemplary, the above coupling provides a support-coupled one-mer peptide product of the formula X-B.

That support-coupled product is then divided into at least 18 aliquots of equal weight, small portions of the preparation often being retained for analytical purposes. Those aliquots are enclosed in labeled porous packets, as discussed in Example 1, and the 18 individual amino acid derivatives are reacted separately with those aliquots after deprotection and neutralization to form 18 support-coupled products of the formula $O_5$X-B.

Those 18 labeled porous packets containing the $O_5$X-B support-coupled product are then deprotected and neutralized together, and those products are together reacted again as discussed before with the mixed amino acid derivatives, while being maintained in their packets, to form 18 sets of support-coupled products of the formula $XO_5$X-B. This procedure is repeated three more times to form the 18 support-coupled 6-mer sets whose fifth position from the N-terminus is occupied by each of the 18 different predetermined amino acid residues and whose other positions are occupied by equimolar amounts of the 18 amino acid residues present in the reaction mixtures.

Where N-terminal acetyl groups are to be used, the N-terminal t-Boc groups are removed, the resulting free amines neutralized and the support-coupled 6-mers are reacted with acetic anhydride to form N-acetyl (Ac) groups. The N-acetyl coupled peptides are then deprotected and cleaved from the solid support to form a plurality (18) of N-acetyl C-terminal amide 6-mer oligopeptide sets.

The above procedures are similarly used, as appropriate, to prepare the remaining five pluralities of 18 sets (another 90 sets) having one of eighteen predetermined amino acid residues at predetermined positions 1–4 and 6, and mixtures of equal molar amounts of the 18 amino acid residues at the other oligopeptide chain positions.

The relative equimolarity of coupling using the above procedure as compared to the physical mixture methods was determined by amino acid analysis of support-coupled products from a single coupling reaction. A commercial amino acid analyzer was utilized for these assays. The specific manipulations utilized are discussed hereinafter.

As is well known, even commercially available amino acid analyzers do not provide precise determinations because of several factors including decomposition of the amino acids, and the various reactions and responses the machines must carry out and make. On the other hand, the physical mixture method provides equimolar mixtures to a precision that is much greater than that obtained by the machine alone.

Thus, a physical mixture process solid support-coupled product (X-B) of one coupling reaction was prepared as in Example 1, deprotected, cleaved from the solid support resin and collected. A similar X-B solid support-coupled product was prepared by the chemical mixture method of this example. That X-B product was similarly deprotected, cleaved from the solid support resin and collected. Those samples were then sent amino acid analysis.

More specifically, after each of the above t-Boc, side chain-protected mixtures was prepared, the t-Boc groups were removed, and the side chains deprotected. Each of the two mixed amino acid-coupled solid supports (X-B) was dried, and 20 mg of each resin-linked product was placed into 5 ml glass ampules. One milliliter of propionic acid:HCl (50:50, V/V) was added to each ampule. Air was removed from the ampules with a vacuum pump with care being taken not to aspirate the contents of the ampules. Each ampule was then sealed using a propane flame, while under vacuum. The sealed ampules were placed in a dry block heater and maintained at 130° C. for two hours to cleave the reacted amino acids from the solid support resin and form hydrolyzate solutions.

Thereafter, upon cooling to room temperature, the ampules were broken open and their contents filtered into separate 12–75 mm culture tubes. Aliquots (20 $\mu$l) of the hydrolyzate solution were placed into 5–50 mm culture tubes in duplicate. Those samples were coded, dried and sealed.

The sealed, coded samples were sent to Core Laboratories, New Orleans, La. for amino acid analysis. The results of that analysis are shown below, for each sample. In addition, because it is known that the physical mixture method provides more precise results than does amino acid analysis, the percentage of deviation from equimolarity for the chemical mixture method was determined by presuming that the value obtained for the individual amino acid residues obtained from the physical mixture method was the correct value of one-eighteenth mole percent (5.56 percent). It is noted that Glu and Gln analyze together as do Asp and Asn because the resin-cleaving step also destroys the Gln and Asn amide bonds, forming Glu and Asp, respectively.

| | Mole Percent | | |
|---|---|---|---|
| Amino Acid | Physical Mixture | Chemical Mixture | Deviation from Equimolarity (Percent) |
| Asp,Asn | 13.84 | 16.73 | +21 |
| Glu,Gln | 10.87 | 11.99 | +10 |
| Ser | 4.11 | 4.14 | −1 |
| Gly | 5.13 | 5.04 | −2 |
| His | 4.84 | 3.16 | −35 |
| Arg | 6.57 | 5.03 | −23 |
| Thr | 5.48 | 6.10 | +11 |
| Ala | 6.36 | 6.48 | +2 |
| Pro | 7.22 | 7.28 | +1 |
| Tyr | 4.31 | 3.53 | −18 |
| Val | 6.08 | 6.76 | +11 |
| Met | 3.38 | 4.13 | +22 |
| Ile | 5.08 | 4.07 | −20 |
| Leu | 6.58 | 5.95 | −10 |
| Phe | 5.17 | 3.78 | −27 |
| Lys | 4.96 | 5.85 | +18 |

Reduction of a chemical mixture-produced oligopeptide set as discussed here, using a reduction discussed in Example 1 provides the corresponding oligoethyleneimine library.

EXAMPLE 3

Synthesis of Peptide Mixtures on Cotton Carriers

Twenty discs cut out of commercially available cotton fabric (diameter 4.7 cm) are shaken for 15 minutes in 50 ml of dichloromethane (DCM) containing 25 percent trifluoroacetic acid (TFA). The discs are then taken out and placed into a flat ceramic funnel with the same diameter as the cotton discs. The funnel is placed on top of an 1000 ml suction flask with an outlet to a vacuum pump. The 25 percent TFA/DCM is removed from the cotton discs into the suction flask under reduced pressure. The cotton discs are then washed with DCM (2×10 ml), DCM containing 5 percent DIEA (2×10 ml) and DCM (2×10 ml) again. The washings are done by adding the wash solution to the funnel holding the cotton discs and removal of the solvent with a vacuum pump. After the last wash the cotton discs are removed and air dried. All manipulations are at room temperature unless otherwise stated.

A. Manual Synthesis

Fmoc-Glycine (1.118 g, 4 mmol), N-hydroxybenztriazole (HOBt) (540 mg, 4 mmol), N-methylimidazole (NMI) (656 $\mu$l, 8 mmol) and DIPCDI (626 $\mu$, 4 mmol) are dissolved in 6.7 ml DMF. This corresponds to a 0.5 M Fmoc-Gly/HOBt/DIPCDI, 1 M NMI solution. The cotton discs are soaked with this solution in a 20 ml scintillation vial and maintained for three hours. After transferring the discs to the ceramic funnel, the cotton carriers are washed with DMF (3×10 ml) and DCM (2×10 ml) as described above. This procedure is repeated once more identically.

The general peptide mixture and single, predetermined peptide coupling procedure is as follows:

1. Fmoc-deprotection: 20 percent piperidine/DMF, 15 minutes.
2. Wash: 3×DMF, 3×DCM.
3. Coupling: 0.3 M Fmoc-amino acid/HOBt/DIC in DMF, 90 minutes—two hours.
4. Wash: 3×DMF, 2×DCM.

More specifically, the twenty cotton discs, placed into the ceramic funnel, are soaked with 10 ml 20 percent piperidine/

DMF, and maintained for 15 minutes. After removing the 20 percent piperidine/DMF, the cotton discs are washed with DMF (3×10 ml) and DCM (2×10 ml) as described above.

(a) Coupling of the same amino acid to all cotton discs

The Fmoc-amino acid to be coupled (2.4 mmol), HOBt (324 mg, 2.4 mmol) and DIPCDI (380 µl, 2.4 mmol) are dissolved in 7.6 ml DMF. This corresponds to a 0.3 M Fmoc-amino acid/HOBt/DIC solution. The cotton discs are soaked with this solution in a 20 ml scintillation vial and maintained for 90 minutes. After transferring the discs to the ceramic funnel, the coupling solution is removed, and the cotton carriers are washed with DMF and DCM, as before.

(b) Coupling of another amino acid to each cotton disc (O-coupling)

The 20 natural amino acids (0.12 mmol each) are separately dissolved in 0.4 ml of a 0.3 M solution of HOBt and DIPCDI in DMF (324 mg HOBt and 380 µl DIPCDI dissolved in 7.6 ml DMF). The cotton discs are labeled as to amino acid identify with the letters A through Y, soaked with the amino acid solution, labeled with the letter of the amino acid of the solution, and maintained for 90 minutes. After transferring the discs to the ceramic funnel, the cotton discs are washed with DMF and DCM, as before.

(c) Coupling of the amino acid mixture (X-coupling)

A 0.3 M solution of the 20 natural amino acids except Cys in the molar ratio of Table 2 and HOBt in DMF is prepared and aliquoted. The aliquots (7.6 ml each) are stored at −20° C. Before the coupling, the mixture aliquot is warmed up to room temperature, followed by addition of 380 µl DIPCDI. After 20 minutes (preactivation), the 19 cotton discs are soaked with this solution and maintained for two hours. After transferring them to the ceramic funnel, the cotton discs are washed with DMF and DCM, as before.

After coupling of the last (N-terminal) amino acid or mixture, the cotton discs are Fmoc-deprotected and washed. The deprotected cotton discs are soaked with 8 ml of a mixture of acetic anhydride/pyridine/DMF 1:2:3 (v/v/v) and maintained for 60 minutes. After transferring them to the ceramic funnel, the cotton discs are washed with DMF and DCM.

The acetylated cotton discs are placed into a bottle containing 30 ml 50 percent TFA, 5 percent triisobutylsilane in DCM and maintained for two hours. After pouring off the solution, 100 ml DCM are added and the bottle shaken for two minutes. This wash is repeated twice with DCM, then three times with 5 percent DIEA/DCM and again three times with DCM. The cotton discs are taken out, blotted between layers of filter paper and air dried. The dry cotton discs are cut into small discs (diameter 7 mm) with an ordinary hole puncher, labeled and refrigerated.

B. Machine Synthesis

The synthesis is done as described in allowed U.S. patent application Ser. No. 07/645,121, whose disclosures are incorporated by reference, and above. The essential difference between the manual synthesis of peptide mixtures and the synthesis of individual peptides on the synthesizer machine is the following: The manually prepared mixtures are synthesized directly on the glycine-cotton. Upon alkaline hydrolysis of the glycine-cotton ester, the cotton-cleaved peptides therefore contain an additional C-terminal Gly residue. In case of the synthesis of individual peptides on the machine synthesizer, a TFA-cleavable linker, in this case N-f-Moc-2,4-dimethoxy-4'-(carboxymethyloxy)-benzhydrylamine for the synthesis of peptide amides, is coupled onto the amino group of the glycine-cotton ester. After Fmoc-deprotection of the linker, the first amino acid of the peptide is coupled to the amino group of the linker. Upon cleavage of the peptides with TFA, simultaneously with the deprotection of side chains, the set of oligopeptide amides are formed, with the linker and the glycine remaining bound to the cotton. Reduction of the oligopeptide amide sets as discussed before provides the corresponding linear substituted oligoethyleneimine libraries.

EXAMPLE 4

Exemplary 6-Mer Preparation and Assay

An N-acetyl C-amide 6-mer oligopeptide set of sets was prepared using the physical mixture method as discussed in Example 1 in which the N-terminal two residues were predetermined from the naturally occurring twenty amino acids and were the same, and the C-terminal four residues were equimolar mixtures of nineteen residues, Cys being omitted from the mixture positions. After deblocking and cleavage from the solid support resins, the sets were reduced using $B_2H_6$ in THF at ambient room temperature for a time period of 100 hours, with a mole ratio of $B_2H_6$ to each carbonyl bonds of 60:1.

Following reduction, samples were taken from each resulting library and were treated with 6N HCl under usual oligopeptide hydrolyzing conditions (reflux for 16 hours) to hydrolyze any remaining peptide bonds. The results of this study showed that where both corresponding N-terminal (first-terminal) amino acid residues were phenylalanine isoleucine, leucine, proline or valine, reduction of carbonyl bonds was substantially complete. Carbonyl bond reductions were not as complete as in other studies. The use of refluxing THF and a reduction reaction time period of 3–4 days at reflux temperature provides substantially complete reduction of all carbonyl bonds present.

Table 3, below, shows a comparison of activities of several linear substituted oligoethyleneimine libraries and corresponding oligopeptide sets when assayed against *Staphylococcus aureus* (*S. aureus*).

TABLE 3

Inhibition of *S. aureus* Growth by
Contact with Hexamer Libraries and Sets[1]

| Amino Acid Side Chain at Positions 1 and 2 | $IC_{50}$ Value for Set (µg/ml) | $IC_{50}$ Value for Library (µg/ml) | Fold Increase[2] |
|---|---|---|---|
| Alanine | >2500 | 156 | >16 |
| Cysteine | >2500 | 39 | >64 |
| Phenylalanine | 1250 | 5–10 | 166 |
| Glycine | >2500 | 1250 | >2 |
| Isoleucine | >2500 | 40–80 | >42 |
| Lysine | 625 | 80–150 | 5 |
| Leucine | ~2500[3] | ~10–20 | >167 |
| Proline | >2500 | ~80–160 | >21 |
| Valine | >2500 | 78 | >32 |
| Tryptophan[4] | 1250 | 2.5–5 | 333 |
| Tyrosine | 325 | 156 | 2 |

[1]Data for N-acetyl C-amide oligopeptide sets and corresponding reduced linear substituted oligoethyleneimine library hexamers where the N-terminal first two residues of the precursor sets were the same and are as shown, and the C-terminal four residues were equimolar mixtures of the remaining residues. No appreciable change in $IC_{50}$ value between the sets and libraries was noted when the remaining nine natural amino acid residues occupied the two N-terminal positions of the precursor sets.
[2]Fold-Increase = $IC_{50}$ for a set/$IC_{50}$ value for a library.
[3]~ = an approximate amount.
[4]N-Formyl or N-methyl tryptophan as appropriate.

As can be seen from the above data, the libraries were either about equivalent to the sets in activity or exhibited enhanced activity in inhibiting growth of *S. aureus*. Tryptophan side chains at the first two positions of the library provided quite active materials and a surprisingly great enhancement in activity (333-fold) over the corresponding oligopeptide set. Each library or set used in these assays contained a mixture of more than 100,000 separate oligomers.

*Staphylococcus aureus* (ATCC 29213) are Gram-positive (+) bacteria. Bacteria were grown overnight (about 18 hours) at 37° C. in Mueller-Hinton I (MHI) broth. This culture was reinoculated and incubated at 37° C. for approximately two hours to reach the exponential phase of bacteria growth. For use in the assay, the bacterial suspension was diluted using double strength (2x) MHI broth to contain about $10^5$ to $5 \times 10^5$ colony-forming units (CFU)/ml. The exact concentration of bacterial cells was established by plating 100 μl of different dilutions of the culture solution (e.g., $10^{-2}$, $10^{-3}$ and $10^{-4}$) onto solid agar plates. Following an overnight (about 18 hours) incubation at 37° C., the CFU thus formed were counted on each agar plate.

Sterile flat-bottomed 96-well culture plates were utilized, with eight wells of the plate containing only medium as control blanks, whereas eight wells contained medium plus bacterial cells as a positive growth control. These controls were used to detect possible medium contamination and to provide a measure of uninhibited growth of the microorganisms. Appropriate dilutions of control antibiotics were also included to ensure the stable antimicrobial susceptibility of the bacterial strain used in the assay.

The oligopeptide sets or oligoethyleneimine libraries were diluted two-fold, ranging from 1000 μg/ml to 1.95 μg/ml, in the same 96-well plates utilizing sterile distilled water. A time=0 (t=0) reading was taken for each plate on an ELISA plate reader at optical density (O.D.) 620 nm. The plates were then incubated overnight (about 18 hours) at 37° C., and the O.D. 620 nm was again determined. The t=0 reading was subtrated from the t=18 hours reading, and the data expressed as the percentage of growth in the treated wells as compared to the untreated (growth control wells). $IC_{50}$ values (concentration necessary to inhibit 50 percent growth of the bacteria) and the MIC (concentration necessary to inhibit 100 percent growth of the bacteria) values were determined.

EXAMPLE 5

Studies with Linear Substitute Diethyleneimines

Twenty separate linear substituted diethyleneimine molecules were prepared from corresponding N-acetyl C-amide dipeptides that were themselves prepared as in Example 1 in which the N-terminal residue was N-methyl Trp (W) and the C-terminal residue was one of the twenty natural amino acid residues. The resulting diethyleneimine molecules had an ethyl group at the first terminus and amino groups at the second terminus. Those separate molecules were then screened for inhibition of growth of *S. aureaus, Candida albicans* (*C. albicans*) and *Streptococcus sanpuis* (*S. sanguis*). The results of those studies are shown in Tables 4 through 6, below, for several of the preferential compounds in terms of $IC_{50}$ values (the concentration necessary to inhibit 50 percent of the growth) and/or MIC values (the concentration necessary to inhibit 100 percent of the growth).

TABLE 4

Inhibition of *S. aureus* Growth by Diethyleneimine Molecules (Reduced N-Acetyl C-Amide Dipeptides)

| Reduced Dipeptide* | $IC_{50}$ Value (μg/ml) | MIC (μg/ml) |
| --- | --- | --- |
| Ac-WW-NH$_2$ | 4.01 | 7.25 |
| Ac-WF-NH$_2$ | 9.15 | 14.5 |
| Ac-WL-NH$_2$ | 10.67 | 29 |
| Ac-WI-NH$_2$ | 20.34 | 29 |
| Ac-WM-NH$_2$ | 24.22 | 58 |
| Ac-WV-NH$_2$ | 26.16 | 58 |
| Ac-WH-NH$_2$ | 29.73 | 58 |
| Ac-WC-NH$_2$ | 34.84 | 58 |
| Ac-WK-NH$_2$ | 35.52 | 58 |
| Ac-WN-NH$_2$ | 36.15 | 58 |
| Ac-WA-NH$_2$ | 36.36 | 58 |
| Controls | | |
| Oxacillin | 0.057 | 0.25 |
| Erythromycin | 0.157 | 1 |

*The diethyleneimine is shown as its precursor corresponding N-acetyl (Ac-) C-amide (-NH$_2$) dipeptide. The prefix RED- usually used for libraries is omitted for better clarity in the table, and all tryptophan residues are present as N-methyl derivatives.

TABLE 5

Inhibition of *S. sanguis* Growth by Diethyleneimine Molecules (Reduced N-Acetyl C-Amide Dipeptides)

| Reduced Dipeptide* | $IC_{50}$ Value (μg/ml) | MIC (μg/ml) |
| --- | --- | --- |
| Ac-WW-NH$_2$ | — | 7.25 |
| Ac-WF-NH$_2$ | 7.49 | 14.5 |
| Ac-WL-NH$_2$ | 8.61 | 14.5 |
| Ac-WI-NH$_2$ | 14.35 | 29 |
| Ac-WV-NH$_2$ | 15.82 | 29 |
| Ac-WM-NH$_2$ | 18.34 | 29 |
| Ac-WK-NH$_2$ | 18.4 | 29 |
| Ac-WH-NH$_2$ | 20.34 | 29 |
| Ac-WC-NH$_2$ | 24.32 | 58 |
| Ac-WA-NH$_2$ | 26.47 | 58 |
| Ac-WD-NH$_2$ | 33.0 | 58 |
| Ac-WQ-NH$_2$ | 34.2 | 58 |
| Ac-WN-NH$_2$ | 35.2 | 58 |
| Ac-WY-NH$_2$ | 38.24 | 58 |
| Ac-WP-NH$_2$ | 39.64 | 58 |

*The diethyleneimine is shown as its precursor corresponding N-acetyl (Ac-) C-amide (-NH$_2$) dipeptide. The prefix RED- usually used for libraries is omitted for better clarity in the table, and all tryptophan residues are present as N-methyl derivatives.

TABLE 6

Inhibition of *C. albicans* Growth by Diethyleneimine Molecules (Reduced N-Acetyl C-Amide Dipeptides)

| Reduced Dipeptide* | $IC_{50}$ Value (μg/ml) |
| --- | --- |
| Ac-WW-NH$_2$ | 132.3 |
| Ac-WQ-NH$_2$ | 208.57 |
| Ac-WF-NH$_2$ | 223.08 |
| Ac-WL-NH$_2$ | 246.42 |
| Ac-WK-NH$_2$ | 261.56 |

TABLE 6-continued

Inhibition of *C. albicans* Growth
by Diethyleneimine Molecules
(Reduced N-Acetyl C-Amide Dipeptides)

| Reduced Dipeptide* | IC$_{50}$ Value ($\mu$g/ml) |
|---|---|
| Controls | |
| Amphotericin B | 3.07 |
| Nystatin | 0.438 |

*The diethyleneimine is shown as its precursor corresponding N-acetyl (Ac-) C-amide (-NH$_2$) dipeptide. The prefix RED- usually used for libraries is omitted for better clarity in the table, and all tryptophan residues are present as N-methyl derivatives.

As is seen from the above assay results, many of the linear substituted diethyleneamines were quite effective, with the N-methyl reduced tryptophan-containing RED-Ac-WW-NH$_2$, RED-Ac-WF-NH$_2$, RED-Ac-WL-NH$_2$ and RED-Ac-WI-NH$_2$ diethyleneimines being particularly active against both *S. aureus* and *S. sanpuis*.

*S. aureus* assays were conducted as described previously, using a concentration of 464 $\mu$g/ml as the initial library concentration.

For antifungal studies carried out using *Candida albicans* ATCC 10231 as the target microbe, the yeast culture was spread onto YM agar plates and incubated at 30° C. for 48 hours. Three colonies of this culture (about 1 mm in diameter each) were then inoculated in 5 ml of 1×PBS solution. The suspension was vortexed and diluted 10-fold in YM broth, for an approximate final concentration of 10$^5$ to 5×10$^5$ CFU (colony forming units)/ml.

Actual concentrations of yeast cultures were determined by plating 100 $\mu$l of different solutions of the culture solution (10$^{-3}$, 10$^{-4}$ and 10$^{-5}$) onto solid YM agar plates. After 48 hours of incubation at 30° C., CFU formed were counted from each plate.

The assays were carried out in 96-well tissue culture plates. Eight wells containing only medium of YM broth served as negative controls, whereas eight wells containing medium and yeast culture served as positive controls. These controls were used to detect possible medium contamination and to provide a measure of uninhibited growth of the yeast. Two antifungal drugs, Amphotericin 8 and Nystatin, were included in each assay for comparative purposes.

For screening studies, diethyleneimines were added to the yeast suspension in duplicates with a starting concentration of 362 $\mu$g/ml. For IC$_{50}$ (concentration necessary to inhibit 50 growth of the yeast) oligoethyleneimines were added to the yeast suspension at concentrations derived from two-fold dilutions. The plates were incubated over a period of 48 hours at 30° C., and the optical density (OD) at 24 and 48 hours was determined at 620 nm.

*Streptococcus sanguis* ATCC 10556 [Gram-positive (+) bacteria present in tooth crevices] was grown overnight at 37° C. in Brain Heart Infusion (BHI) broth. This culture was reinoculated and incubated at 37° C. to reach the exponential phase of bacterial growth; i.e., a final bacterial suspension containing 10$^5$ to 5×10$^5$ colony-forming units (CFU)/ml. The concentration of cells was established by plating 100 $\mu$l of different dilutions of the culture solution (e.g., 10$^{-2}$, 10$^{-3}$ and 10$^{-4}$) onto solid agar plates. Following an overnight (about 18 hour) incubation at 37° C., the CFU thus formed were counted on each agar plate.

In 96-well tissue culture plates, as control blanks, eight wells per plate contained only medium, while as a positive growth control, eight other wells contained medium plus cells. These controls were used to detect possible medium contamination and to provide a measure of uninhibited growth of the microorganisms. For screening studies, ethyleneimines were added to the bacterial suspension at a starting concentration of about 4.64 $\mu$g/ml. The plates were incubated overnight (about 18 hours) at 37° C., and the optical density (OD) determined at 620 nm after 20 to 24 hours incubation.

EXAMPLE 6

Studies with Linear Substituted Ethyleneimine Libraries

Dimer, trimer and hexamer libraries were prepared from correspondng N-acetyl C-amide oliopeptide sets prepared as described in Example 1. Reduction of the oligopeptide sets to form the libraries was carried out using 1M diborane-THF in sufficient volume to provide an approximately 25:1 mole ratio of reductant to carbonyl groups. The reduction was carried out at reflux for about 96 hours, followed by work-up as discussed before.

The constructed libraries contained one of nineteen predetermined amino acid side chains at the first terminus and equimolar amounts of nineteen amino acid side chains (Cys omitted) at the second terminus (dimer); a predetermined amino acid side chain at the first terminus, one of nineteen predetermined side chains on the second repeating unit, and equimolar amounts of the same nineteen side chains at the second terminus (trimer); and two predetermined side chains at the first two terminal repeating unit positions, one of nineteen predetermined side chains on the third repeating unit and equimolar amounts of the same nineteen side chains at each of the three second-terminal repeating unit positions (hexamer).

Using the nomenclature discussed before, these three types of libraries can be depicted by the following formulas:

RED-Ac-OX-NH$_2$;

RED-Ac-O$_1$OX-NH$_2$; and

RED-Ac-O$_1$O$_2$OXXX-NH$_2$.

Representative data for the preferential results obtained with four libraries used to inhibit growth of *C. albicans* are shown in Table 7, below.

TABLE 7

Inhibition of Growth of *C. albicans*
Using Diethyleneimine Libraries
(Reduced N-Acetyl C-Amide Peptide Sets)

| Reduced Peptide[1] | IC$_{50}$ Value ($\mu$g/ml)[2] | MIC Value ($\mu$g/ml)[2] |
|---|---|---|
| Ac-HX-NH$_2$ | 60.33 | 125 |
| Ac-AX-NH$_2$ | 66.1 | 250 |
| Ac-FX-NH$_2$ | 67.43 | 250 |
| Ac-LX-NH$_2$ | 72.27 | 250 |
| Ac-GX-NH$_2$ | 81.43 | 250 |
| Ac-EX-NH$_2$ | 84.56 | 250 |
| Ac-QX-NH$_2$ | 88.41 | 250 |
| Ac-IX-NH$_2$ | 92.66 | 250 |
| Ac-WX-NH$_2$ | 95.63 | 250 |
| Ac-WNX-NH$_2$ | 31.25 | 62.5 |
| Ac-WKX-NH$_2$ | 31.45 | 62.5 |
| Ac-WQX-NH$_2$ | 31.48 | 62.5 |
| Ac-WRX-NH$_2$ | 31.63 | 62.5 |
| Ac-WFX-NH$_2$ | 31.81 | 125 |
| Ac-WHX-NH$_2$ | 42.67 | 125 |
| Ac-WIX-NH$_2$ | 42.76 | 250 |

TABLE 7-continued

Inhibition of Growth of *C. albicans*
Using Diethyleneimine Libraries
(Reduced N-Acetyl C-Amide Peptide Sets)

| Reduced Peptide[1] | IC$_{50}$ Value ($\mu$g/ml)[2] | MIC Value ($\mu$g/ml)[2] |
|---|---|---|
| Ac-WWX-NH$_2$ | 46.01 | 125 |
| Ac-WWYXXX-NH$_2$ | 29.31 | 62.5 |
| Ac-WWFXXX-NH$_2$ | 32.55 | 125 |
| Ac-WWGXXX-NH$_2$ | 32.93 | 125 |
| Ac-WWNXXX-NH$_2$ | 33.06 | 125 |
| Ac-WWSXXX-NH$_2$ | 33.1 | 62.5 |
| Ac-WWLXXX-NH$_2$ | 34.35 | 125 |
| Ac-WWIXXX-NH$_2$ | 36.32 | 125 |
| Ac-WWEXXX-NH$_2$ | 38.35 | 125 |
| Ac-WWMXXX-NH$_2$ | 38.46 | 250 |
| Ac-WWWXXX-NH$_2$ | 38.54 | 125 |
| Ac-WWVXXX-NH$_2$ | 39.5 | 125 |
| Ac-WWPXXX-NH$_2$ | 40.03 | 125 |
| Ac-LLWXXX-NH$_2$ | 30.97 | 62.5 |
| Ac-LLQXXX-NH$_2$ | 31.08 | 62.5 |
| Ac-LLLXXX-NH$_2$ | 31.11 | 62.5 |
| Ac-LLSXXX-NH$_2$ | 31.13 | 62.5 |
| Ac-LLFXXX-NH$_2$ | 31.14 | 62.5 |
| Ac-LLRXXX-NH$_2$ | 31.25 | 62.5 |
| Ac-LLVXXX-NH$_2$ | 31.25 | 62.5 |
| Ac-LLTXXX-NH$_2$ | 31.25 | 62.5 |
| Ac-LLAXXX-NH$_2$ | 31.25 | 62.5 |
| Ac-LLDXXX-NH$_2$ | 31.25 | 62.5 |
| Ac-LLKXXX-NH$_2$ | 31.25 | 62.5 |
| Ac-LLGXXX-NH$_2$ | 31.25 | 62.5 |
| Ac-LLIXXX-NH$_2$ | 31.33 | 62.5 |
| Controls | | |
| Amphotericin B | 5.08 | >25 |
| Nystatin | 0.815 | 2 |

[1]Each oligoethyleneimine library is shown as its precursor corresponding N-acetyl (Ac-) C-amide (-NH$_2$) oligopeptide set. The prefix RED- usually used for libraries is omitted for better clarity in the table, and all tryptophan residues are present as N-methyl derivatives.
[2]These studies were carried out as discussed in Example 5 with two exceptions: (1) the starting concentration was 250 $\mu$g/ml, and (2) four rather than eight 2-fold dilutions were used.

EXAMPLE 7

Inhibition of the Growth of Methicillin-Resistant *S. aureus* Using Various Oligoethyleneimine Libraries and Individual Oligoethyleneimine Molecules A series of exemplary studies were carried out to examine inhibition of the growth of methicillin-resistant *S. aureus* (MRSA; ATCC 33591) using oligoethyleneimine libraries and individiaul oligoehtyleneimine molecules prepared by reduction of N-acetyl C-amide oligopeptide sets and individual dipeptides as the inhibitors. The oligopeptide sets were prepared and were reduced as discussed in Example 1.

This strain of *S. aureus* was cultured as discussed before with the following changes: an incubation temperature of 35° C. was used instead of 37° C., and the bacterial cells were cultured in Mueller-Hinton II broth (cation-adjusted). IC$_{50}$ values were determined as discussed before using the following library or diethyleneimine concentration ranges: RED-Ac-WO-NH$_2$ 362.5–2.83 $\mu$g/ml, and 500–3.9 $\mu$g/ml for the libraries. The concentration of a library or diethyeleneimine that killed one-half of either Vero (ATCC CCL 81) or McCoy (ATCC CRL 1696) mammalian cells (TC$_{50}$ values) was also calculated. Therapeutic indices (T.I. values) as to this *S. aureus* and one or the other of the mammalian cells were also determined (T.I.=TI$_{50}$/IC$_{50}$). Representative results for the more active libraries are shown in Tables 8–12 below.

TABLE 8

Inhibition of Growth of Methicillin-Resistant
*S. aureus* Using Diethyleneimine Libraries
(Reduced N-Acetyl C-Amide Dipeptide Sets)

| Reduced Peptide[1] | IC$_{50}$ Value ($\mu$g/ml) | TC$_{50}$ Value ($\mu$g/ml)[2] | T.I.[3] |
|---|---|---|---|
| Ac-QX-NH$_2$ | 5.3 | 4.6 | 0.87 |
| Ac-NX-NH$_2$ | 6.7 | 5.1 | 0.76 |
| Ac-PX-NH$_2$ | 7.2 | 5.7 | 0.79 |
| Ac-RX-NH$_2$ | 10.8 | 4.2 | 0.39 |
| Ac-HX-NH$_2$ | 17.9 | 1.9 | 0.11 |
| Ac-GX-NH$_2$ | 19.4 | 5.1 | 0.26 |
| Ac-EX-NH$_2$ | 20.8 | 5.3 | 0.25 |
| Ac-AX-NH$_2$ | 22.5 | 5.2 | 0.23 |
| Ac-TX-NH$_2$ | 25.9 | 4.2 | 0.16 |
| Ac-IX-NH$_2$ | 27.1 | 2.1 | 0.08 |
| Ac-SX-NH$_2$ | 29 | 5.2 | 0.18 |
| Ac-DX-NH$_2$ | 33.6 | 1.7 | 0.05 |
| Ac-KX-NH$_2$ | 38.1 | 4.7 | 0.12 |
| Ac-WX-NH$_2$ | 46.3 | 1.8 | 0.04 |

[1]Each diethyleneimine library is shown as its precursor corresponding N-acetyl (Ac-) C-amide (-NH$_2$) dipeptide set. The prefix RED- usually used for libraries is omitted for better clarity in the table, and all tryptophan residues are present as N-methyl derivatives.
[2]TC = The quantity of linear substituted oligoethyleneimine required to kill one-half of McCoy cells (ATCC CRL 1696).
[3]TI = Therapeutic index, TC$_{50}$/IC$_{50}$.

TABLE 9

Inhibition of Growth of Methicillin-Resistant
*S. aureus* Using Diethyleneimines
(Reduced N-Acetyl C-Amide Dipeptides)

| Reduced Peptide[1] | IC$_{50}$ Value ($\mu$g/ml) | TC$_{50}$ Value ($\mu$g/ml)[2] | T.I.[3] |
|---|---|---|---|
| Ac-WW-NH$_2$ | 7.57 | 7 | 0.92 |
| Ac-WL-NH$_2$ | 12.41 | 15.9 | 1.28 |
| Ac-WI-NH$_2$ | 13.78 | 15.4 | 1.12 |
| Ac-WK-NH$_2$ | 14.76 | 221.3 | 14.99 |
| Ac-WV-NH$_2$ | 16.17 | 22.4 | 1.39 |
| Ac-WH-NH$_2$ | 18.48 | >250 | >13.52 |
| Ac-WF-NH$_2$ | 19.43 | 9.1 | 0.47 |

[1]Each diethyleneimine is shown as its precursor corresponding N-acetyl (Ac-) C-amide (-NH$_2$) dipeptide. The prefix RED- usually used for libraries is omitted for better clarity in the table, and all tryptophan residues are present as N-methyl derivatives.
[2]TC = The quantity of linear substituted oligoethyleneimine required to kill one-half of cultured Vero cells (ATCC CCL 81).
[3]TI = Therapeutic index, TC$_{50}$/IC$_{50}$.

TABLE 10

Inhibition of Growth of Methicillin-Resistant
*S. aureus* Using Triethyleneimine Libraries
(Reduced N-Acetyl C-Amide Tripeptide Sets)

| Reduced Peptide[1] | IC$_{50}$ Value ($\mu$g/ml) | TC$_{50}$ Value ($\mu$g/ml)[2] | T.I.[3] |
|---|---|---|---|
| Ac-WFX-NH$_2$ | 4.9 | 1.03 | 0.21 |
| Ac-WLX-NH$_2$ | 5.4 | 0.94 | 0.17 |
| Ac-WIX-NH$_2$ | 6.7 | 0.98 | 0.15 |
| Ac-WWX-NH$_2$ | 8.3 | 0.68 | 0.08 |
| Ac-WHX-NH$_2$ | 8.5 | 1.17 | 0.14 |
| Ac-WQX-NH$_2$ | 8.9 | 0.75 | 0.08 |
| Ac-WVX-NH$_2$ | 9.2 | 0.8 | 0.09 |
| Ac-WKX-NH$_2$ | 9.6 | 0.72 | 0.08 |

TABLE 10-continued

Inhibition of Growth of Methicillin-Resistant
S. aureus Using Triethyleneimine Libraries
(Reduced N-Acetyl C-Amide Tripeptide Sets)

| Reduced Peptide[1] | IC$_{50}$ Value ($\mu$g/ml) | TC$_{50}$ Value ($\mu$g/ml)[2] | T.I.[3] |
|---|---|---|---|
| Control | | | |
| Ac-WXX-NH$_2$ | 12.3 | | |

[1]Each triethyleneimine library is shown as its precursor corresponding N-acetyl (Ac-) C-amide (-NH$_2$) tripeptide set. The prefix RED- usually used for libraries is omitted for better clarity in the table, and all tryptophan residues are present as N-methyl derivatives.
[2]TC = The quantity of linear substituted oligoethyleneimine required to kill one-half of McCoy cells (ATCC CRL 1696).
[3]TI = Therapeutic index, TC$_{50}$/IC$_{50}$.

TABLE 11

Inhibition of Growth of Methicillin-Resistant
S. aureus Using Hexaethyleneimine Libraries
(Reduced N-Acetyl C-Amide Hexpeptide Sets)

| Reduced Peptide[1] | IC$_{50}$ Value ($\mu$g/ml) | TC$_{50}$ Value ($\mu$g/ml)[2] | T.I.[3] |
|---|---|---|---|
| Ac-WWVXXX-NH$_2$ | 5.1 | 1.02 | 0.20 |
| Ac-WWIXXX-NH$_2$ | 5.4 | 2.06 | 0.38 |
| Ac-WWWXXX-NH$_2$ | 6 | 0.98 | 0.16 |
| Ac-WWMXXX-NH$_2$ | 6.2 | 2.04 | 0.33 |
| Ac-WWFXXX-NH$_2$ | 6.6 | 1.07 | 0.16 |
| Control | | | |
| Ac-WWXXXX-NH$_2$ | 4.58 | | |

[1]Each oligoethyleneimine library is shown as its precursor corresponding N-acetyl (Ac-) C-amide (-NH$_2$) olgipeptide set. The prefix RED- usually used for libraries is omitted for better clarity in the table, and all tryptophan residues are present as N-methyl derivatives.
[2]TC = The quantity of linear substituted oligoethyleneimine required to kill one-half of McCoy cells (ATCC CRL 1696).
[3]TI = Therapeutic index, TC$_{50}$/IC$_{50}$.

TABLE 12

Inhibition of Growth of Methicillin-Resistant
S. aureus Using Hexaethyleneimine Libraries
(Reduced N-Acetyl C-Amide Hexpeptide Sets)

| Reduced Peptide[1] | IC$_{50}$ Value ($\mu$g/ml) | TC$_{50}$ Value ($\mu$g/ml)[2] | T.I.[3] |
|---|---|---|---|
| Ac-LLVXXX-NH$_2$ | 6 | 0.78 | 0.13 |
| Ac-LLAXXX-NH$_2$ | 6.1 | 0.62 | 0.10 |
| Ac-LLDXXX-NH$_2$ | 6.1 | 0.69 | 0.11 |
| Ac-LLKXXX-NH$_2$ | 6.2 | 0.72 | 0.12 |
| Ac-LLWXXX-NH$_2$ | 6.3 | 1.13 | 0.18 |
| Ac-LLQXXX-NH$_2$ | 6.8 | 1.03 | 0.15 |
| Ac-LLHXXX-NH$_2$ | 6.9 | 0.73 | 0.11 |
| Control | | | |
| Ac-LLXXXX-NH$_2$ | 11.4 | | |

[1]Each oligoethyleneimine library is shown as its precursor corresponding N-acetyl (Ac-) C-amide (-NH$_2$) oligopeptide set. The prefix RED- usually used for libraries is omitted for better clarity in the table, and all tryptophan residues are present as N-methyl derivatives.
[2]TC = The quantity of linear substituted oligoethyleneimine required to kill one-half of McCoy cells (ATCC CRL 1696).
[3]TI = Therapeutic index, TC$_{50}$/IC$_{50}$.

The data of the above tables indicate that several of the diethyleneimines and oligoethyleneimine libraries are quite active against this drug-resistant strain of S. aureus.

IC$_{50}$ Values were obtained using an assay based on 3-(4,5-dimethylthiazol-2-yl)-2,5-diphenyl-2H-tetrazolium bromide (MTT) as follows. Reduced peptides or mixtures were diluted in Dulbecco's Modified Eagle's Medium (DMEM) containing 2 percent fetal bovine serum (FBS) and added in a volume of 200 $\mu$l to appropriate wells of 96-well plates containing a confluent monolayer of either Vero or McCoy cells. Controls were included that contained medium only. The plates were incubated at 37° C. in 5 percent CO$_2$ for 20 to 24 hours. A solution was prepared containing 0.5 mg/ml MTT diluted in DMEM containing 2 percent FBS (the NTT solution was centrifuged prior to use at 3800 rpm for three minutes and carefully decanted into a 50 ml tube). The reduced peptide samples and controls were aspirated from the 96-well plates and replaced with 200 $\mu$l of the MTT solution, a blank well was included that contained just the MTT solution and no cells.

The plates were incubated for two hours at 37° C. in an atmosphere containing 5 percent CO$_2$. The MTT solution was removed, taking care to disturb the cells as little as possible. The remaining cells were then washed with 200 $\mu$l of PBS for one minute at room temperature. The PBS was then removed.

Isopropanol (100 $\mu$l) was then added to the cells of each well, and those isopropanol-contacted cells were maintained at room temperature for 20 minutes. The plates were kept covered during this time to retard evaporation.

The plates were then tapped to evenly distribute the blue color and the optical densities (O.D.) at 595 nm were read for each well. Where the O.D. readings were much greater than 1.0, another 100 $\mu$l of isopropanol were added to each well of the plate, and each well was re-read.

EXAMPLE 8

Comparative Toxicity Studies with Methicillin-Resistant S. aureus Using Oligoethyeleneimine Libraries and Corresponding oligopeptide Sets Comparative studies were carried out to measure the inhibition (IC$_{50}$) values of several oligoethyleneimine libraries and their precursor corresponding N-acetyl C-amide oligopeptide sets toward the MRSA of Example 7. The libraries and sets used in these studies contained three, four, five or six repeating units or amino acid residues, respectively, and were prepared as in Example 1. Several of the libraries of Example 7 were included in these studies.

The bacterial cells were cultured as discussed before, with inhibition determinations being determined as discussed in Example 7. Libraries or sets were screened at concentrations of 250–1.95 $\mu$g/ml or 125–0.98 $\mu$g/ml. The results for several of these studies are shown below in Table 13.

TABLE 13

Inhibition of S. aureus (ATCC 33591) by
Oliogethyleneimine Libraries and
Precursor Corresponding Oligopeptide Sets

| Reduced Library Amino Acid Side Chains at Positions 1 or 1 and 2[1] | IC$_{50}$ Value for Libraries ($\mu$g/ml) | IC$_{50}$ Value for Sets ($\mu$g/ml) |
|---|---|---|
| WNXXXX | 4.58 | >250 |
| LLXXXX | 11.4 | >250 |
| KKXXXX | 11.9 | >250 |
| WXX | 12.3 | >125 |
| RXXX | 13 | NT[2] |
| WXXXXX | 15.5 | >250 |
| HHXXXX | 16.3 | >250 |

TABLE 13-continued

Inhibition of *S. aureus* (ATCC 33591) by
Oliogethyleneimine Libraries and
Precursor Corresponding Oligopeptide Sets

| Reduced Library Amino Acid Side Chains at Positions 1 or 1 and 2[1] | IC$_{50}$ Value for Libraries (µg/ml) | IC$_{50}$ Value for Sets (µg/ml) |
|---|---|---|
| VVXXXX | 17.1 | >250 |
| QQXXXX | 17.6 | >250 |
| FFXXXX | 18.4 | >250 |
| YYXXXX | 18.5 | >250 |
| EEXXXX | 18.9 | >250 |
| IIXXXX | 20.2 | >250 |
| NNXXXX | 20.3 | >250 |
| EXXXXX | 22.7 | >250 |
| CCXXXX | 26.7 | >250 |
| RXXXXX | 28.7 | >250 |
| TXXXXX | 29.3 | >250 |
| KXXXXX | 29.9 | >250 |
| MXXXXX | 31.9 | >250 |
| RRXXXX | 34.8 | >250 |
| YXXXXX | 36.3 | >250 |
| MMXXXX | 36.4 | >250 |
| PPXXXX | 38.9 | >250 |
| KXXX | 40.6 | >125 |
| QXXXXX | 48 | >250 |
| WXXXX | 52.3 | >125 |
| GGXXXX | 54.5 | >250 |
| VXXXXX | 56.5 | >250 |
| FXXXXX | 62.4 | >250 |
| PXXXXX | 63.9 | >250 |
| CXXXXX | 64.5 | >250 |
| LXXXXX | 72.7 | >250 |
| SXXXXX | 74.1 | >250 |
| DXXX | 91.2 | >125 |
| IXXXXX | 98.2 | >250 |

[1]Terminal reduced N-acetyl and C-amide groups are not shown for greater clarity, all tryptophan residues are present as N-methyl derivatives, and "X" indicates a position occupied by equimolar amounts of reduced amino acid side chains or residues.
[2]NT = not tested The data of Table 13 again illustrate the enhanced inhibition of oligoethyleneimine libraries as compared to their precursor corresponding oligopeptide sets.

EXAMPLE 9

Hemolytic Assays of Diethyleneimine Libraries and Individual Diethyleneimine Molecules The toxicity of several exemplary oligoethyleneimine molecules and libraries toward another relevant type of cells was evaluated in a hemolytic assay using human red blood cells with some of the more active diethyleneimine molecules and libraries prepared from N-acetyl C-amide dipepetides and dipeptide sets. Assays were carried out in 96-well culture tissue plates. Four wells per plate contained 125 µl of a non-peptide positive control of the surfactant Triton X-100 [(poly)oxyethanol (9) octyl phenyl ether; 1 percent in deionized water], and four wells per plate contained 115 µl of a control blank of phosphate-buffered saline (PBS). The hemolytic peptide melittin was used as comparative control in an amount of its IC$_{50}$ value of 4.0 µg/ml. The controls served to detect possible contamination and to calculate the percent hemolysis of each peptide.

Heparinized human red blood cells (RBC's) were washed with PBS and centrifuged to separate them from the plasma. The cells are then resuspended in PBS to a final suspension of 0.5 percent RBC. This suspension (125 µl) was added to library or set solutions and also to control solutions. The plates were incubated at 37° C. for one hour and centrifuged at 2800 rpm for five minutes. The release of hemoglobin resulting from the cell lysis was determined by measuring the OD at 414 nm of 100 µl of the supernatant.

At the highest concentration of oligoethyleneimine or oligoethyleneimine library used for the antimicrobial assay (500 µg/ml), each individual molecule or library exhibited a hemolytic effect. Percentages of hemolysis of from about 3.5 through 50 percents were observed.

At concentrations of 250 µg/ml and 125 µg/ml only the diethyleneimine library RED-Ac-MX-NH$_2$ exhibited hemolysis, and the percentage at both concentrations was 0.3. No hemolysis for any of these libraries was observed at 62.5 µg/ml.

The twenty diethyleneimines based on N-methyl tryptophan (RED-Ac-WO-NH$_2$) exhibited hemolysis at 500 Ag/ml ranging from about 3 to about 45 percent that of millitin. The two most active diethyleneimines of Tables 4 and 5 (RED-Ac-WW-NH$_2$ and RED-Ac-WF-NH$_2$) were among the most hemolytic at 500 µg/ml, and were substantially non-hemolytic after each of three two-fold dilutions; i.e., RED-Ac-WW-NH$_2$:2.3 percent (250 µg,;), 9.8 percent (125 µg/ml) and 0.2 percent (62.5 µg/ml), and RED-Ac-WF-NH$_2$:1.6 percent (250 µg/ml) and 0.0 percent (125 and 62.5 µg/ml).

EXAMPLE 10

Inhibition of the Growth of Herpes Simplex Virus with Oligoethyleneimine Libraries The activity of 120 oligoethyleneimine libraries and diethyleneimines was examined for inhibiting the growth of herpes Simplex virus type-1, strain KOS, (HSV-1) in a preliminary screening. Vero cells (ATCC CCL 81) were used to grow this virus.

The 120 libraries and diethyleneimines used for this screening, prepared as in Example 1, were as follows, using the nomenclature described before:

RED-Ac-WO$_{1-20}$-NH$_2$;
RED-Ac-O$_{1-20}$XX-NH$_2$;
RED-Ac-O$_{1-20}$XXX-NH$_2$;
RED-Ac-O$_{1-20}$XXXX-NH$_2$;
RED-Ac-O$_{1-20}$XXXXX-NH$_2$; and
RED-Ac-O$_{1-20}$O$_{1-20}$XXXX-NH$_2$ wherein each of the subscripted O$_{1-20}$ are the reduced twenty naturally occurring amino acids, and the O$_{1-20}$O$_{1-20}$ of the last library are pairs of the same twenty reduced side chains. Thus, 100 libraries and 20 diethyleneimines were used in this screening.

Of the 120 libraries and diamines examined, only the library RED-Ac-WXXX-NH$_2$ prepared from a set made using N-formyl tryptophan exhibited significant activity in these screenings. Using triplicate determinations, that library was found to be 100 percent active at each of the three concentrations-used: 100, 50 and 25 µg/ml. No toxicity to the Vero cells was observed at the two lower concentrations, whereas the 100 µg/ml concentration was lightly toxic (27 percent).

These assays were carried out using the following protocol. Vero cells were seeded for 24 hours prior to the assay in 96-well flat-bottomed tissue culture plates at a density of 150,000 cells/ml in a volume of 0.1 ml per well in DMEM medium with 5 percent fetal bovine serum (FBS).

Libraries were diluted to appropriate concentrations in DMEM with 2 percent FBS and 50 µl were added to appropriate wells of the sterile plates that contained Vero cell monolayers. Plates were incubated at 37° C. in 5 percent $CO_2$. This incubation lasted about 1–2 hours.

Libraries were diluted to appropriate concentrations in DMEM with 2 percent FBS, and 75 µl were added to appropriate wells of other sterile 96-well plates. Stock virus was diluted in DMEM with 2 percent FBS to contain 100 $TCID_{50}$ (tissue culture infectious dose) and 75 µl were added to the library-containing wells. Medium containing no virus was similarly added to the toxicity control wells containing libraries only. A virus titration was included with each assay as a control of the input virus concentration. The plates were tapped to mix the solutions and the library/virus mixtures were incubated for one hour at 37° C. in a 5 percent $CO_2$ atmosphere.

The Vero cell-containing plates were removed from the incubator and the fluid was aspirated a few rows at a time, taking care that the cells did not become dry. One hundred microliters of the library/virus mixture were added to appropriate wells, and the plates were incubated for 48 hours, as before.

After controls had reached a state in which 80–90 percent of the cell monlayers were affected by virus, the medium was aspirated from all of the wells, and the cells were fixed using 50 µl of methanol per well. After maintaining the methanol contact for 10 minutes, the methanol was aspirated and the cells were air dried.

Non-specific binding sites on the wells were then blocked using 200 µl of a buffer containing one percent casein. The buffer used was PBS that contained 0.05 percent Tween-20 (PBS-T). The wells were incubated for one hour at 37° C. and the liquid was aspirated from the wells.

A solution (50 µl) of mouse monoclonal antibodies to HSV-1 (Chemicon, Temecula Calif.) at a dilution of 1:1,000 in PBS-T with 0.1 percent casein (diluting buffer) was added to the wells, and the plates were incubated at 37° C. in a humidified chamber for one hour. The plates were then washed three times with PBS-T.

One hundred microliters of a solution prepared by mixing o-phenylenediamine (Sigma Chemical Co., St. Louis Mo.) at 10 mg in 6 ml of distilled water plus 25 µl of 3 percent $H_2O_2$ were added to the wells. The plates were incubated in the dark for 15 minutes. The reaction was stopped by the addition of 50 µl of 3M $H_2SO_4$.

Optical densities at 492 nm were read on a plate reader. Positive samples were determined as those libraries that inhibited growth by more than 50 percent as compared to the positive control.

This assay procedure provides both a toxicity screen by contacting libraries with the cells, and two types of screens against the virus. Contacting of a library with the cells permits binding of library molecules to cell surface and other cellular receptors that can inhibit subsequent viral infection. Contacting of the virus and library prior to inoculating the cells permits the libary molecules to bind to viral ligands that can prevent infection by the virus or be directly viricidal.

The foregoing is intended as illustrative of the present invention but not limiting. Numerous variations and modifications may be effected without departing from the true spirit and scope of the novel concepts of the invention.

What is claimed is:

1. A library of linear substituted oligoalkyleneimine chains comprising a mixture of equimolar amounts of linear oligoalkyleneimine chain members containing the same number of about two to about ten alkyleneimine repeating units in each chain, each of said alkyleneimine repeating units having a length of two to about six carbon atoms and having a reduced amino acid side chain bonded to the carbon atom alpha to the nitrogen atom in which the carboxamide groups of said reduced amino acid side chains are replaced by aminomethyl groups, carboxyl groups of said reduced amino acid side chains are replaced by hydroxymethyl groups, and guanidino groups of said reduced amino acid side chains are replaced by amino groups, the members of said library having one or more of said repeating units containing a predetermined reduced amino acid side chain at the same one or more predetermined positions of the oligoalkyleneimine chain, and the library having equimolar amounts of repeating units that contain at least six different of said reduced amino acid side chains at one or more of the same other positions of the oligoalkyleneimine chain, a first terminus of each of said oligoalkyleneimines in the library having a hydrogen, benzyl or $C_1$–$C_{18}$ hydrocarbyl group bonded to an amino group, and the second terminus being a hydroxyl or methylamino group.

2. The library of oligoalkyleneimine chains according to claim 1 wherein said one or more repeating units containing said reduced amino acid side chains at the same one or more predetermined positions of the oligoalkyleneimine chain are at a predetermined position that is adjacent to one terminus.

3. The library of oligoalkyleneimine chains according to claim 2 wherein said one terminus is said first terminus.

4. The library of oligoalkyleneimine chains according to claim 3 wherein the first two repeating units containing said reduced amino acid side chains at the same one or more predetermined positions are adjacent said first terminus.

5. The library of oligoalkyleneimine chains according to claim 1 wherein said equimolar amounts of repeating units that contain at least six different of said reduced amino acid side chains are at one or more positions that are adjacent to one terminus.

6. The library of oligoalkyleneimine chains according to claim 5 wherein said one terminus is said second terminus.

7. The library of oligoalkyleneimine chains according to claim 1 wherein each chain contains five to about eight repeating units.

8. The library of oligoalkyleneimine chains according to claim 1 that is an acid addition salt.

9. A library of linear substituted oligoethyleneimine chains comprising a mixture of equimolar amounts of linear oligoethyleneimine chain members containing the same number of about two to about ten ethyleneimine repeating units in each chain, each of said ethyleneimine repeating units having a reduced amino acid side chain bonded to the carbon atom alpha to the nitrogen atom in which the carboxamide groups of said reduced amino acid side chains are replaced by aminomethyl groups, carboxyl groups of said reduced amino acid side chains are replaced by hydroxymethyl groups, and guanidino groups of said reduced amino acid side chains are replaced by amino groups, the members of said library having one or more of said repeating units containing a predetermined reduced amino acid side chain at the same one or more predetermined positions of the oligoethyleneimine chain, and the library having equimolar amounts of repeating units that contain at least six different of said reduced amino acid side chains at one or more of the same other positions of the oliogethyleneimine chain, a first terminus of each of said oligoethyleneimines in the library having a hydrogen, benzyl or $C_1$–$C_{18}$ hydrocarbyl group bonded to an amino group, and the second terminus being a hydroxyl or methylamino group.

10. The library of oligoethyleneimine chains according to claim 9 wherein said one or more repeating units containing said reduced amino acid side chains at the same one or more predetermined positions of the oligoethyleneimine chain are at a predetermined position that is adjacent to one terminus.

11. The library of oligoethyleneimine chains according to claim 10 wherein said one terminus is said first terminus.

12. The library of oliogethyleneimine chains according to claim 10 wherein the first two repeating units containing said reduced amino acid side chains at the same one or more predetermined positions are adjacent said first terminus.

13. The library of oligoethyleneimine chains according to claim 9 wherein said equimolar amounts of repeating units that contain at least six different of said reduced amino acid side chains are at one or more positions that are adjacent to one terminus.

14. The library of oligoethyleneimine chains according to claim 13 wherein said one terminus is said second terminus.

15. The library of oligoethyleneimine chains according to claim 9 wherein each chain contains five to about eight repeating units.

16. The library of oliogethyleneimine chains that is an acid addition salt accoring to claim 9.

* * * * *